US010947503B2

(12) United States Patent
Sugiyama et al.

(10) Patent No.: US 10,947,503 B2
(45) Date of Patent: Mar. 16, 2021

(54) METHOD FOR MODIFYING T CELL POPULATION

(71) Applicant: International Institute of Cancer Immunology, Inc., Suita (JP)

(72) Inventors: Haruo Sugiyama, Minoo (JP); Fumihiro Fujiki, Kawabe-gun (JP)

(73) Assignee: International Institute of Cancer Immunology, Inc., Suita (JP)

( * ) Notice: Subject to any disclaimer, the term of this patent is extended or adjusted under 35 U.S.C. 154(b) by 0 days.

(21) Appl. No.: 15/537,927

(22) PCT Filed: Dec. 22, 2015

(86) PCT No.: PCT/JP2015/085793
§ 371 (c)(1),
(2) Date: Jul. 26, 2017

(87) PCT Pub. No.: WO2016/104486
PCT Pub. Date: Jun. 30, 2016

(65) Prior Publication Data
US 2017/0369841 A1    Dec. 28, 2017

(30) Foreign Application Priority Data

Dec. 25, 2014 (JP) .............................. JP2014-263398

(51) Int. Cl.
| C12N 15/113 | (2010.01) |
| C12N 5/0783 | (2010.01) |
| A61K 31/713 | (2006.01) |
| A61K 31/7105 | (2006.01) |
| A61K 45/00 | (2006.01) |
| A61K 45/06 | (2006.01) |
| A61K 48/00 | (2006.01) |
| A61K 38/55 | (2006.01) |
| A61K 39/00 | (2006.01) |
| A61K 39/39 | (2006.01) |

(52) U.S. Cl.
CPC .......... *C12N 5/0637* (2013.01); *A61K 31/713* (2013.01); *A61K 31/7105* (2013.01); *A61K 38/55* (2013.01); *A61K 39/0011* (2013.01); *A61K 39/39* (2013.01); *A61K 45/00* (2013.01); *A61K 45/06* (2013.01); *A61K 48/00* (2013.01); *C12N 5/0638* (2013.01); *C12N 15/113* (2013.01); *C12N 15/1137* (2013.01); *A61K 2039/55511* (2013.01); *A61K 2039/572* (2013.01); *C12N 2310/14* (2013.01); *C12N 2501/71* (2013.01); *C12N 2501/999* (2013.01)

(58) Field of Classification Search
CPC ............. C12N 15/113; C12N 2310/14; C12N 2310/315; C12N 2310/351; C12N 2310/31; A61P 43/00; A61P 35/00; A61P 1/16

See application file for complete search history.

(56) References Cited

U.S. PATENT DOCUMENTS

| 7,420,034 | B2 | 9/2008 | Sugiyama et al. |
| 7,622,119 | B2 | 11/2009 | Sugiyama |
| 7,666,985 | B2 | 2/2010 | Sugiyama et al. |
| 8,388,975 | B2 | 3/2013 | Sugiyama |
| 8,759,483 | B2 | 6/2014 | Sugiyama |
| 8,778,350 | B2 | 7/2014 | Sugiyama |
| 8,933,038 | B2 | 1/2015 | Sugiyama |
| 8,945,578 | B2 | 2/2015 | Sugiyama |
| 8,968,745 | B2 | 3/2015 | Sugiyama |
| 2003/0032078 | A1* | 2/2003 | Travis .................... A61K 45/06 435/26 |
| 2003/0119715 | A1 | 6/2003 | Ward et al. |
| 2009/0076032 | A1 | 3/2009 | Ward et al. |
| 2009/0136470 | A1 | 5/2009 | Cheroutre et al. |
| 2010/0113610 | A1 | 5/2010 | Kim et al. |
| 2012/0142109 | A1 | 6/2012 | Katayama et al. |
| 2013/0196427 | A1 | 8/2013 | Suguiyama |
| 2013/0266958 | A1 | 10/2013 | Sugiyama |

FOREIGN PATENT DOCUMENTS

| CN | 102656263 A | 9/2012 |
| EP | 2 471 901 A1 | 7/2012 |
| JP | 2004-506691 | 3/2004 |
| JP | 2009-529572 | 8/2009 |
| JP | 2010-531138 | 9/2010 |
| WO | WO 02/15920 | 2/2002 |
| WO | WO 03/106682 | 12/2003 |
| WO | WO 2005/095598 | 10/2005 |
| WO | WO 2007/097358 | 8/2007 |
| WO | WO 2007/105015 | 9/2007 |
| WO | WO 2008/137488 A1 | 11/2008 |
| WO | WO 2008/157394 | 12/2008 |
| WO | WO 2011/024791 | 3/2011 |

(Continued)

OTHER PUBLICATIONS

Wu et al. (Hepatology (2008) 47:1905-1915), (Year: 2008).*
Extended European Search Report dated Aug. 23, 2018 in Patent Application No. 15873054.9, 9 pages.
International Search Report dated Feb. 16, 2016, in PCT/JP2015/085793.
International Preliminary Report on Patentability and Written Opinion dated Jul. 6, 2017, in PCT/JP2015/085793.
X. Tan et al., "Retinoic Acid as a Vaccine Adjuvant Enhances CD8+ T Cell Response and Mucosal Protection from Viral Challenge," *Journal of Virology*, Aug. 2011, vol. 85, No. 16, pp. 8316-8327.

(Continued)

*Primary Examiner* — J. E. Angell
(74) *Attorney, Agent, or Firm* — Oblon, McClelland, Maier & Neustadt, L.L.P.

(57) ABSTRACT

Provided is a method for increasing the proportion of memory T cells in a T cell population, said method comprising a step of adding a modulator for the retinoid metabolic pathway and/or a modulator for the retinoic acid signaling system to the T cell population.

11 Claims, 44 Drawing Sheets
Specification includes a Sequence Listing.

(56) References Cited

FOREIGN PATENT DOCUMENTS

WO  WO 2012/046730  4/2012

OTHER PUBLICATIONS

K. Furugaki et al., "DNA Vaccination with all-trans Retinoic Acid Treatment Induces Long-Term Survival and Elicits Specific Immune Responses Requiring CD4+ and CD8+ T-Cell Activation in an Acute Promyelocytic Leukemia Mouse Model," Blood, Jan. 2010, vol. 115, No. 3, pp. 653-656.

K.C. Galvin et al., "Blocking Retinoic Acid Receptor-α Enhances the Efficacy of a Dendritic Cell Vaccine Against Tumours by Suppressing the Induction of Regulatory T Cells", *Cancer Immunol Immunother*, 2013, vol. 62, pp. 1273-1282.

S.R. Allie, et al., "Critical Role for All-trans Retinoic Acid for Optimal Effector and Effector Memory CD8 T Cell Differentiation," *The Journal of Immunology*, 2013, vol. 190, pp. 2178-2187.

J.L. Napoli, "Physiological Insights Into All-Trans-Retinoic Acid Biosynthesis," *Biochimica et Biophysics Acta*, 2012, vol. 1821, pp. 152-156.

Y. Oka et al., "Human Cytotoxic T-Lymphocyte Responses Specific for Peptides of the Wild-Type Wilms' Tumor Gene (WT1) Product", *Immunogenetics*, Feb. 2000, 51(2), pp. 99-107.

J.L. Napoli, "Physiological Insights Into All-Trans-Retinoic Acid Biosynthesis," *Biochimica et Biophysica Acta*, 2012, vol. 1821, pp. 152-167.

Japanese Office Action dated Nov. 12, 2019, in Japanese Patent Application No. 2016-566379 (with English Translation).

Jinming, et al., Aldehyde dehydrogenase 1 activity in the developing human pancreas modulates retinoic acid signaling in mediating islet differentiation and survival, Diabetologia, 2014, vol. 57, p. 754-764.

The U.S. Office Action dated Jan. 21, 2020, issued in the related U.S. Appl. No. 16/347,337.

Abe et al., Interferon induction by glycyrrhizin and glycyrrhetinic acid in mice, Microbiology and Immunology, 26(6), 535-539 (Year: 1982).

The Chinese Office Action dated Jan. 10, 2020, issued in the corresponding Chinese application No. 201580070889.3 and English translation thereof.

Laura Cammas, Expression of the murine retinol dehydrogenase 10 (Rdh10) gene correlates with many sites of retinoid signaling during embryogenesis and organ differentiation, Developmental Dynamics, 236:2899-2908, 2007.

He Yifeng, Cancer-associated CD8+memory T cells in the application of adoptive immunotherapy, Chinese Journal of Cancer Biotherapy, vol. 19, No. 2 (including English abstract).

The Indian Office Action dated Feb. 26, 2020, issued in the corresponding Indian Patent application No. 201747025434.

European Office Action dated Aug. 14, 2019, in European Patent Application No. 15873054.9 (5 pages).

Allie, S.R. et al.: "Critical Role for All-trans Retinoic Acid for Optimal Effector and Effector Memory CD8 T Cell Differentiation", The Journal of Immunology, vol. 190, No. 5, 2013, pp. 2178-2187, XP055459748.

Office Action dated Sep. 4, 2020 in corresponding Chinese Patent Application No. 201580070889.3 (with English Translation), 11 pages.

European Office Action dated Apr. 15, 2020 in Patent Application No. 15 873 054.9, 6 pages.

Miller H. Wilson Jr., "The Emerging Role of Retinoids and Retinoic Acid Metabolism Blocking Agents in the Treatment of Cancer" Cancer, American Cancer Society, vol. 83, No. 8, XP002213936, Oct. 15, 1998, pp. 1471-1482.

\* cited by examiner

[Fig. 1]
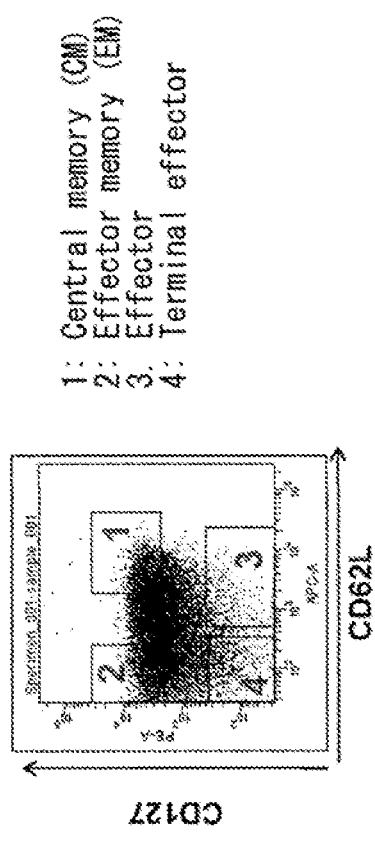
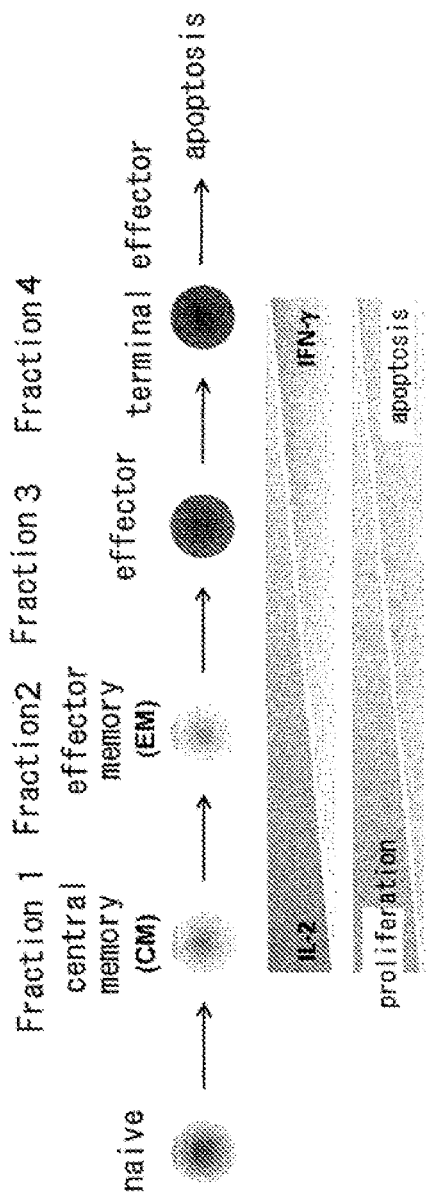

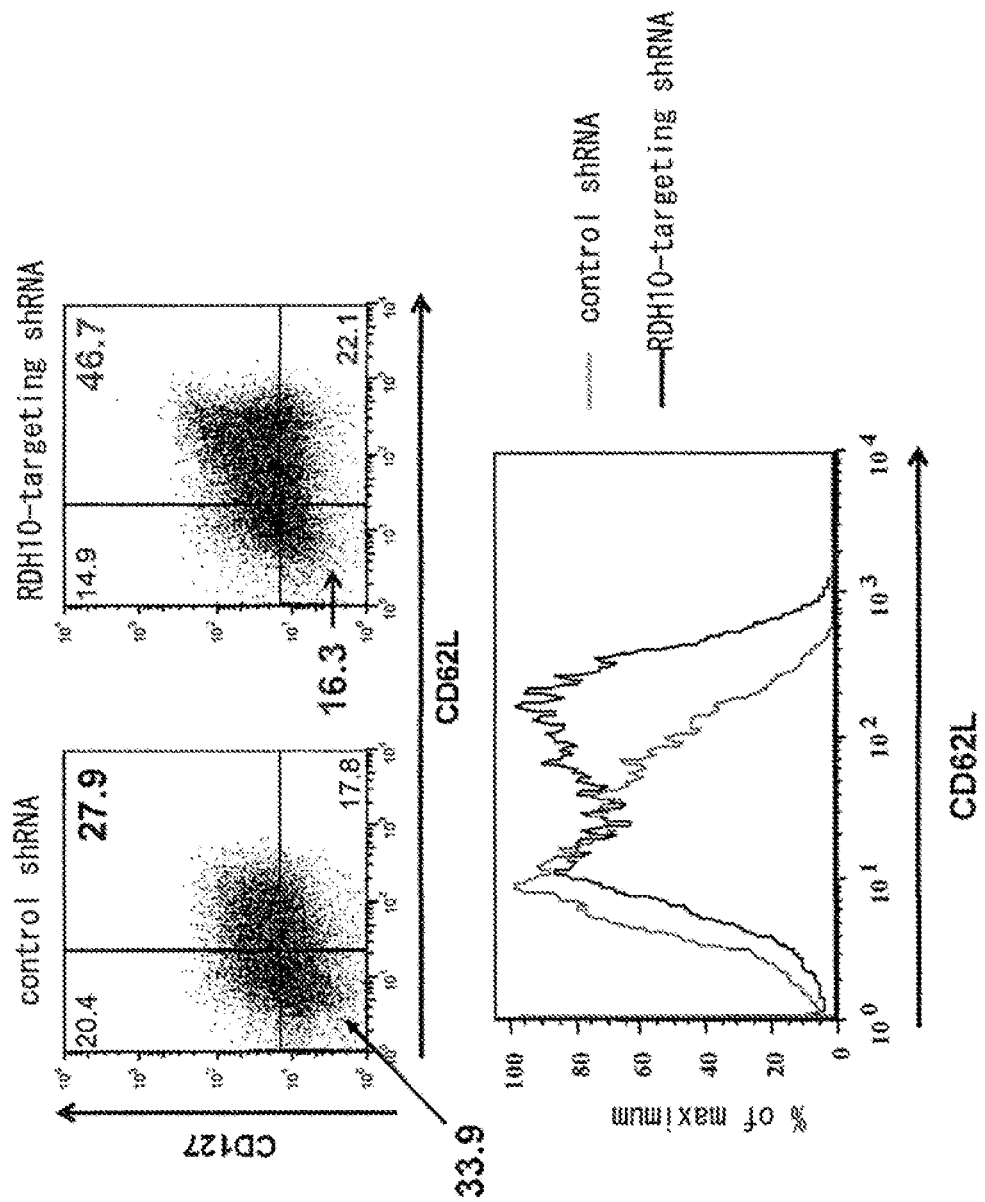
[Fig. 2]

[Fig. 3]
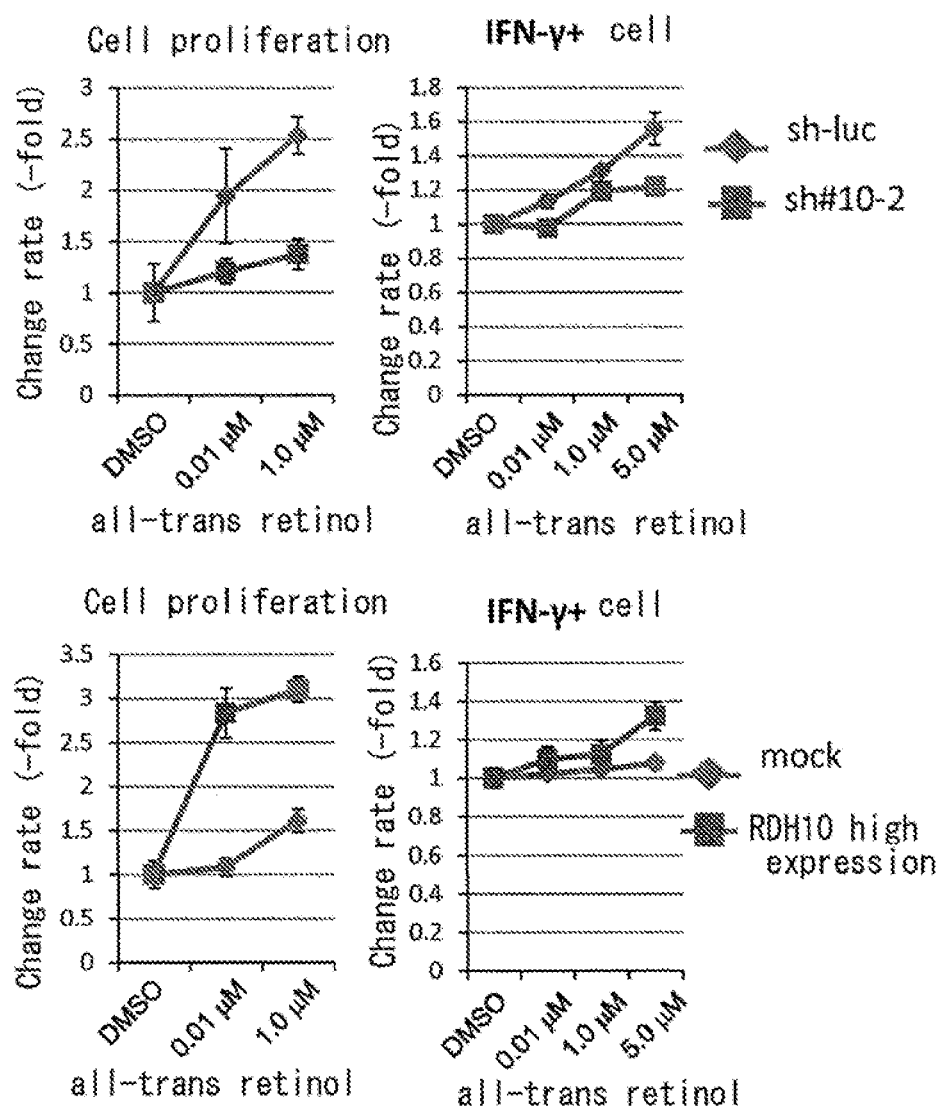

[Fig. 4]
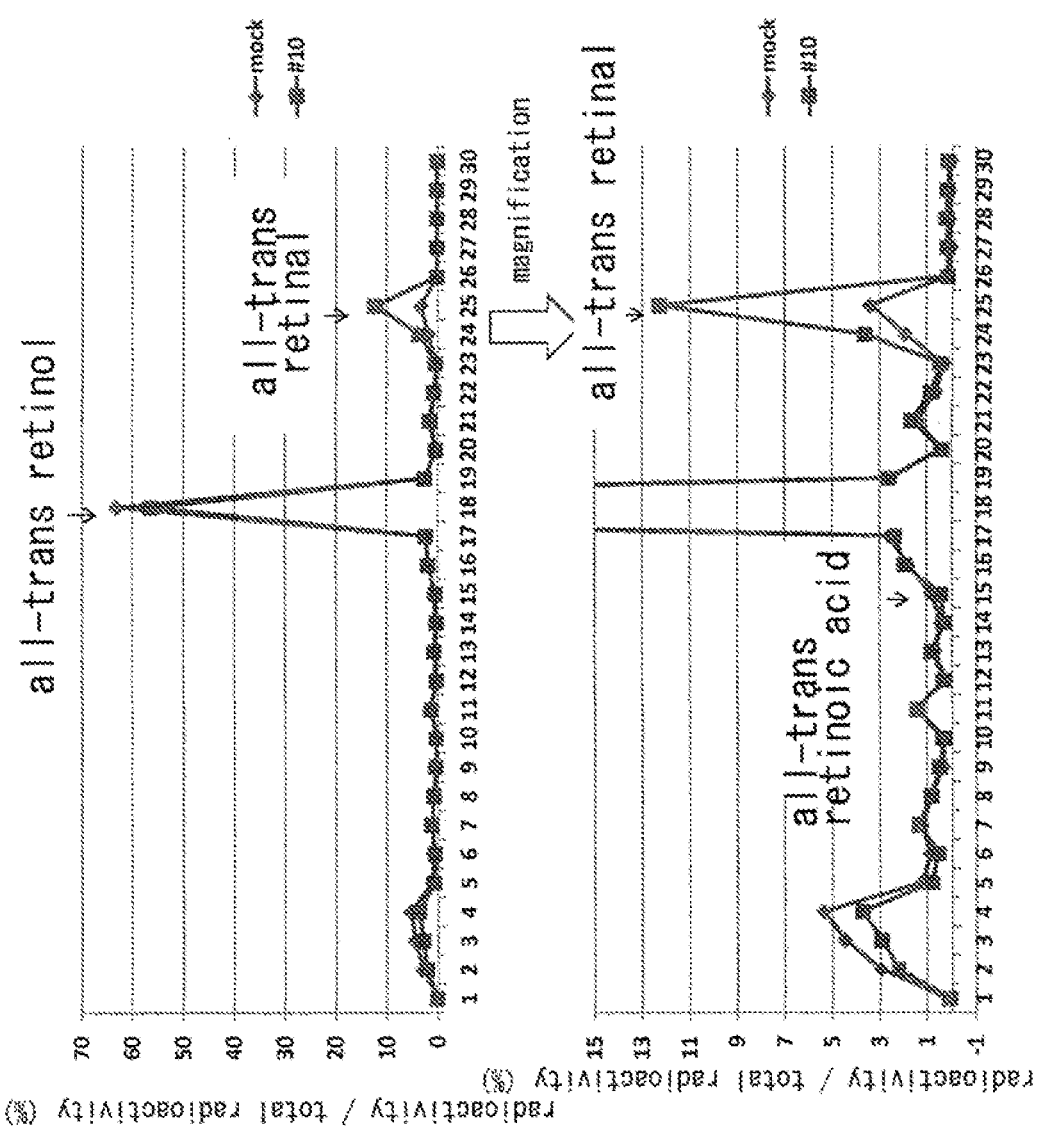

[Fig.5]
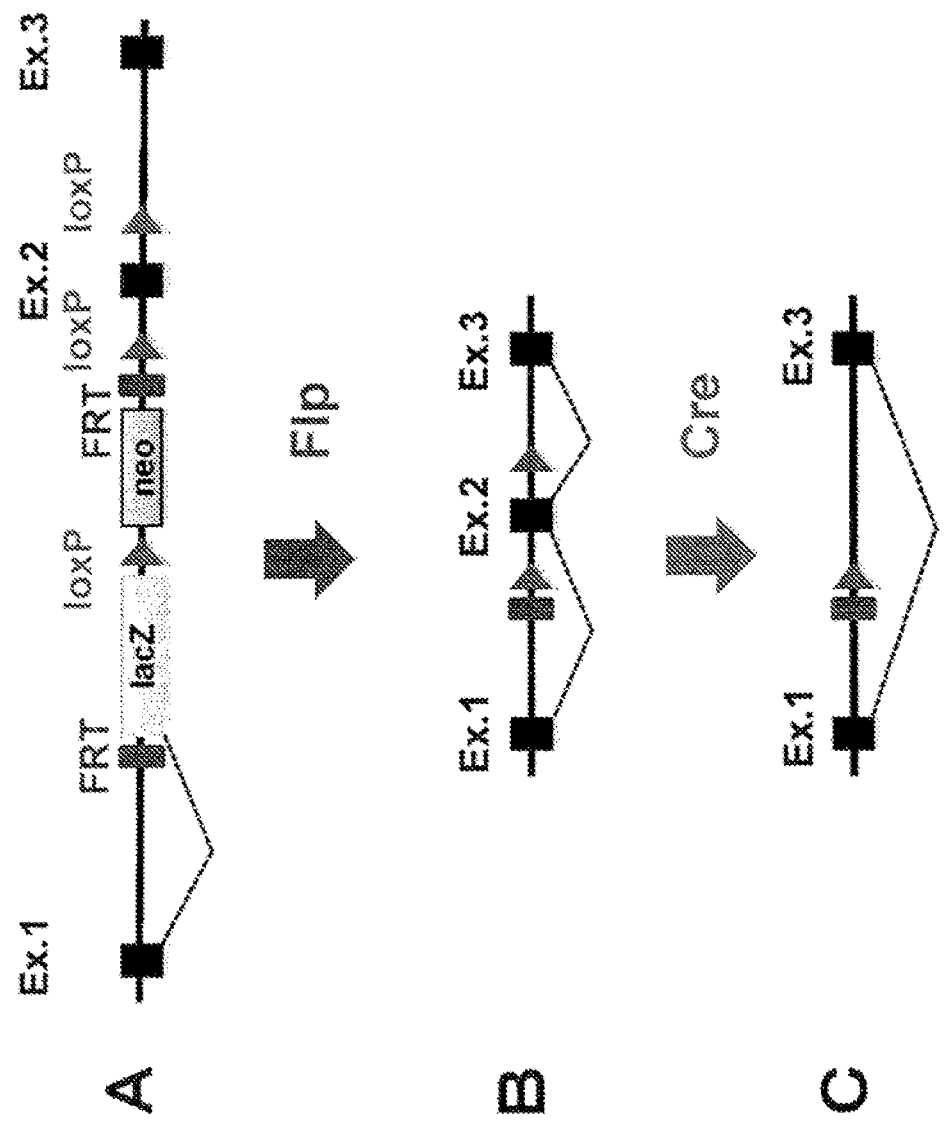

[Fig. 6]
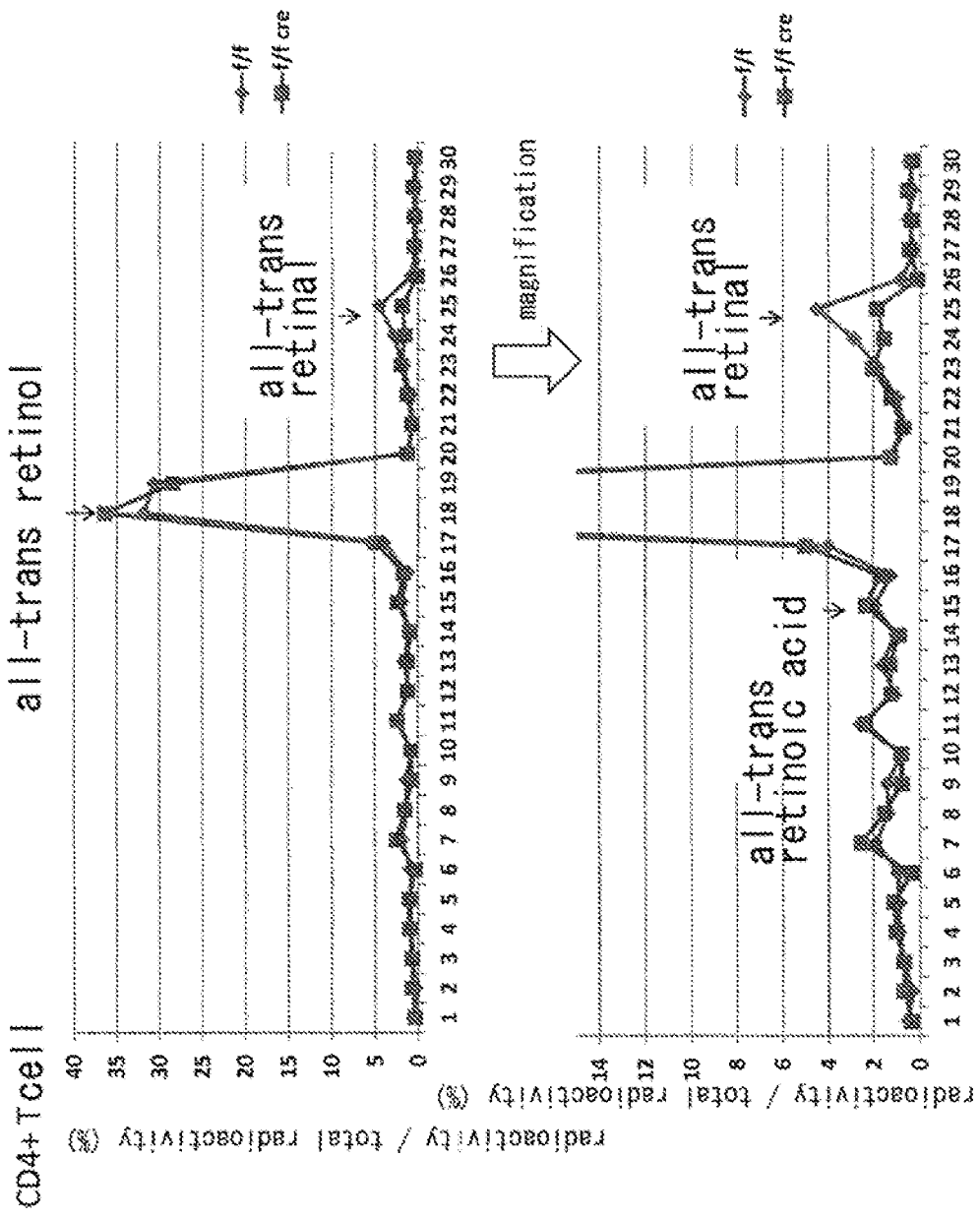

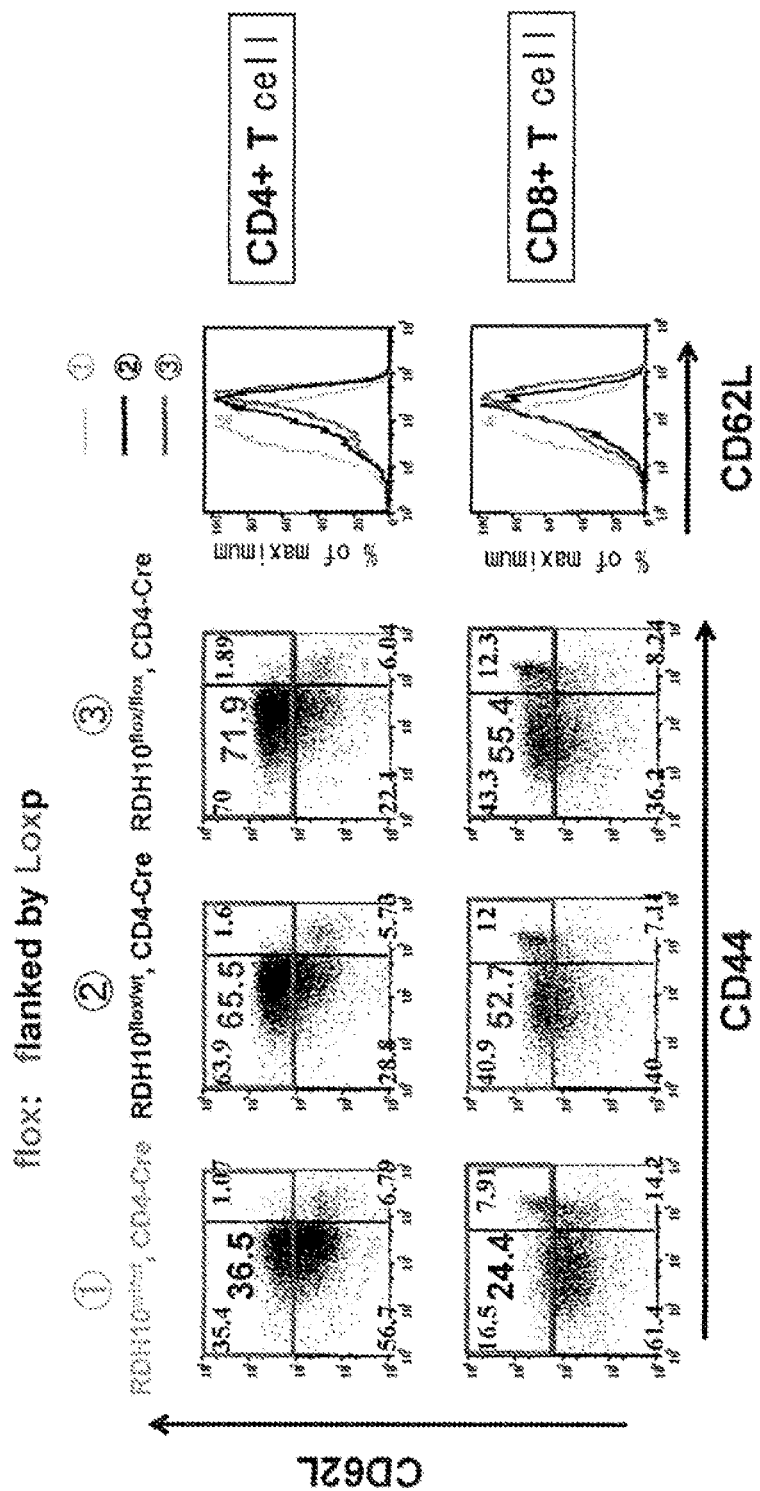
[Fig. 7]

[Fig. 8]
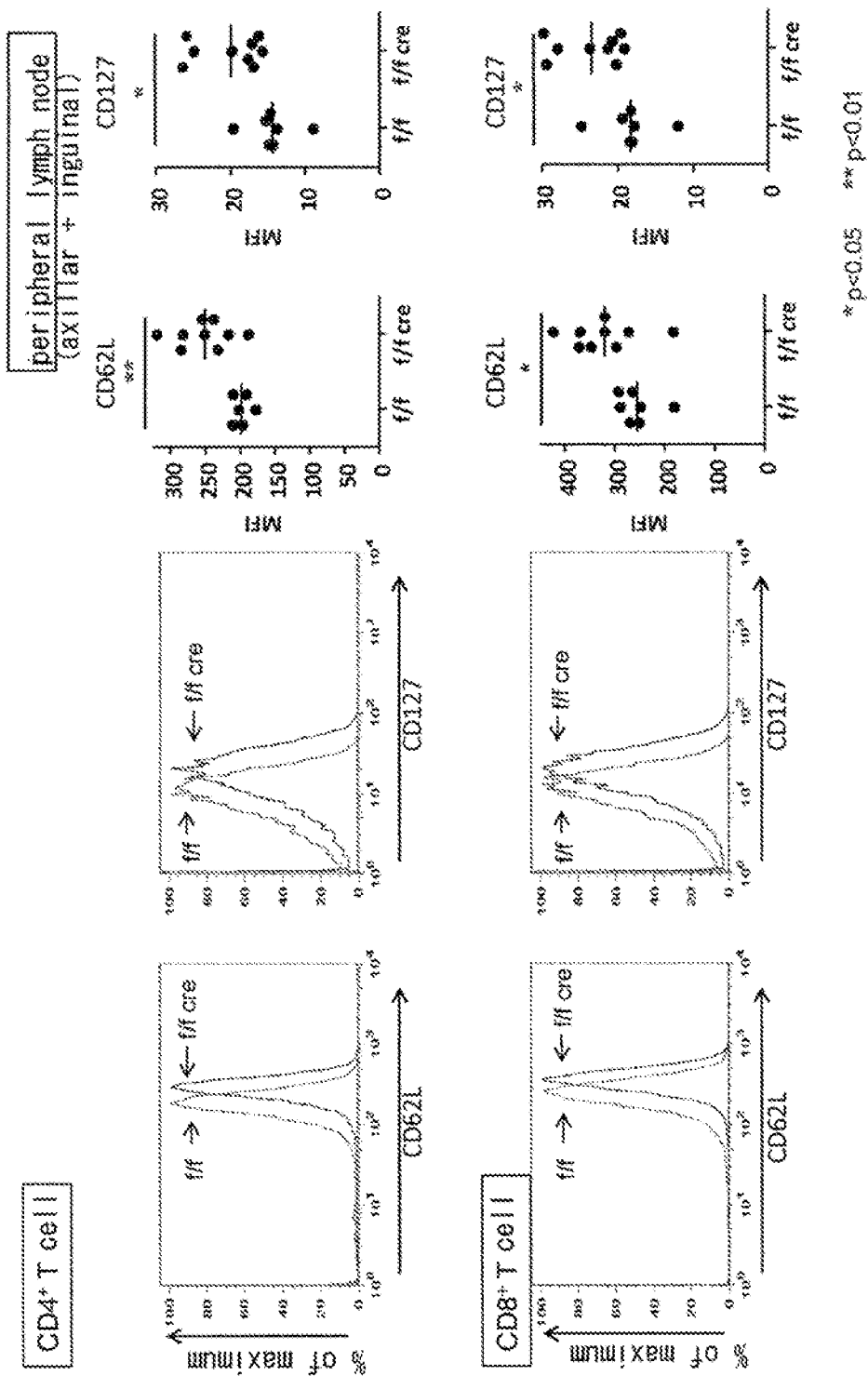

[Fig. 9]
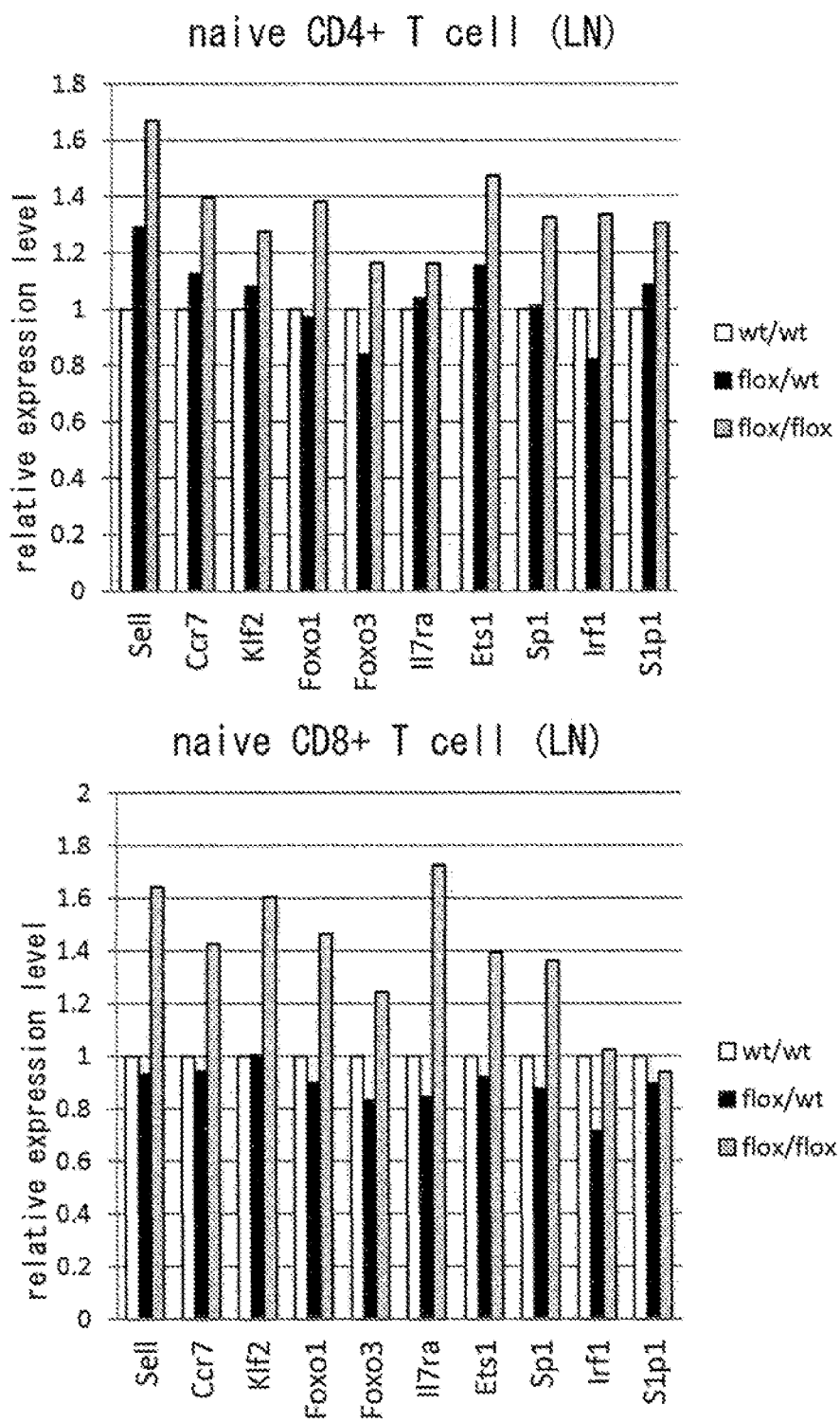

[Fig. 10]
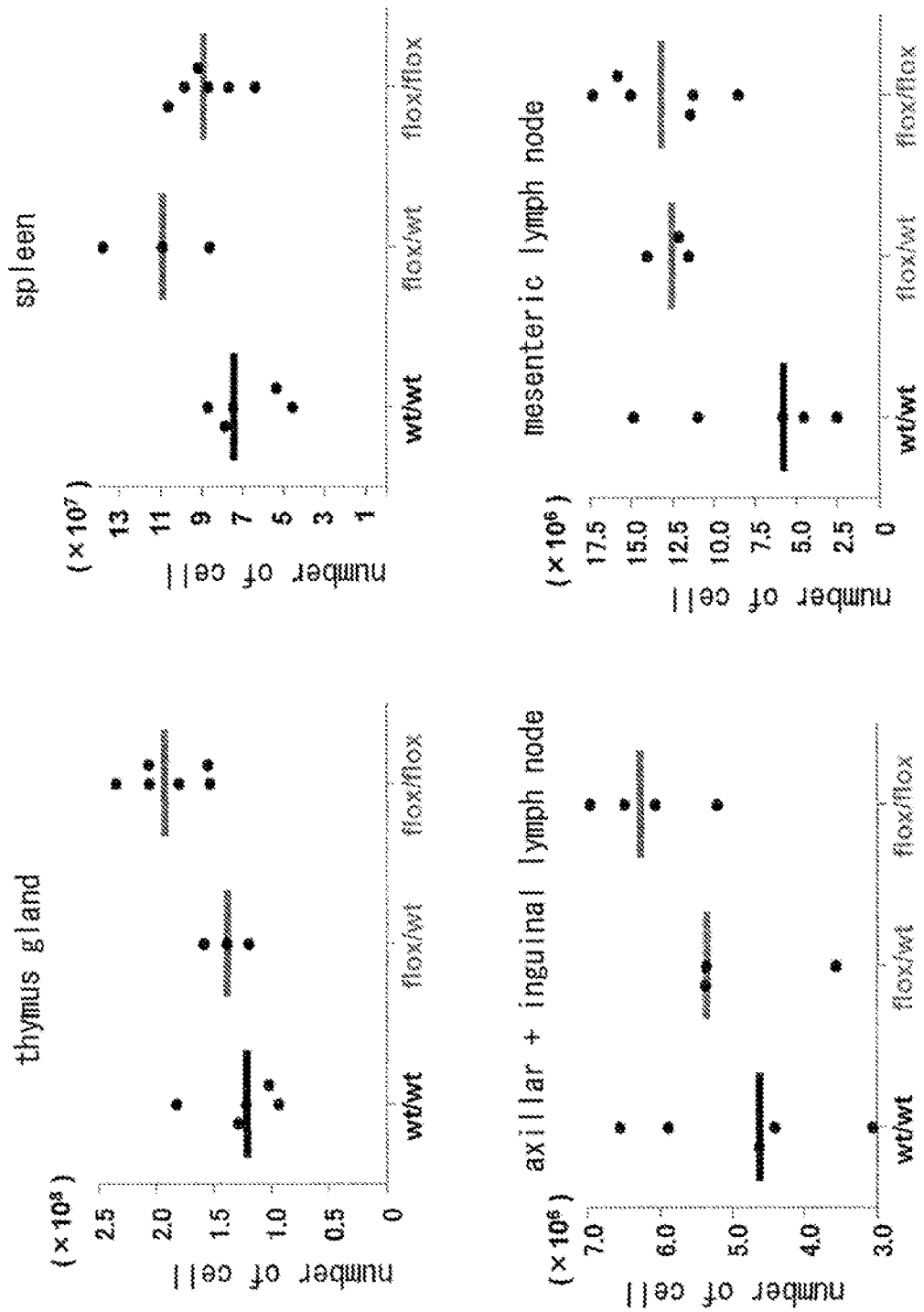

[Fig. 11]
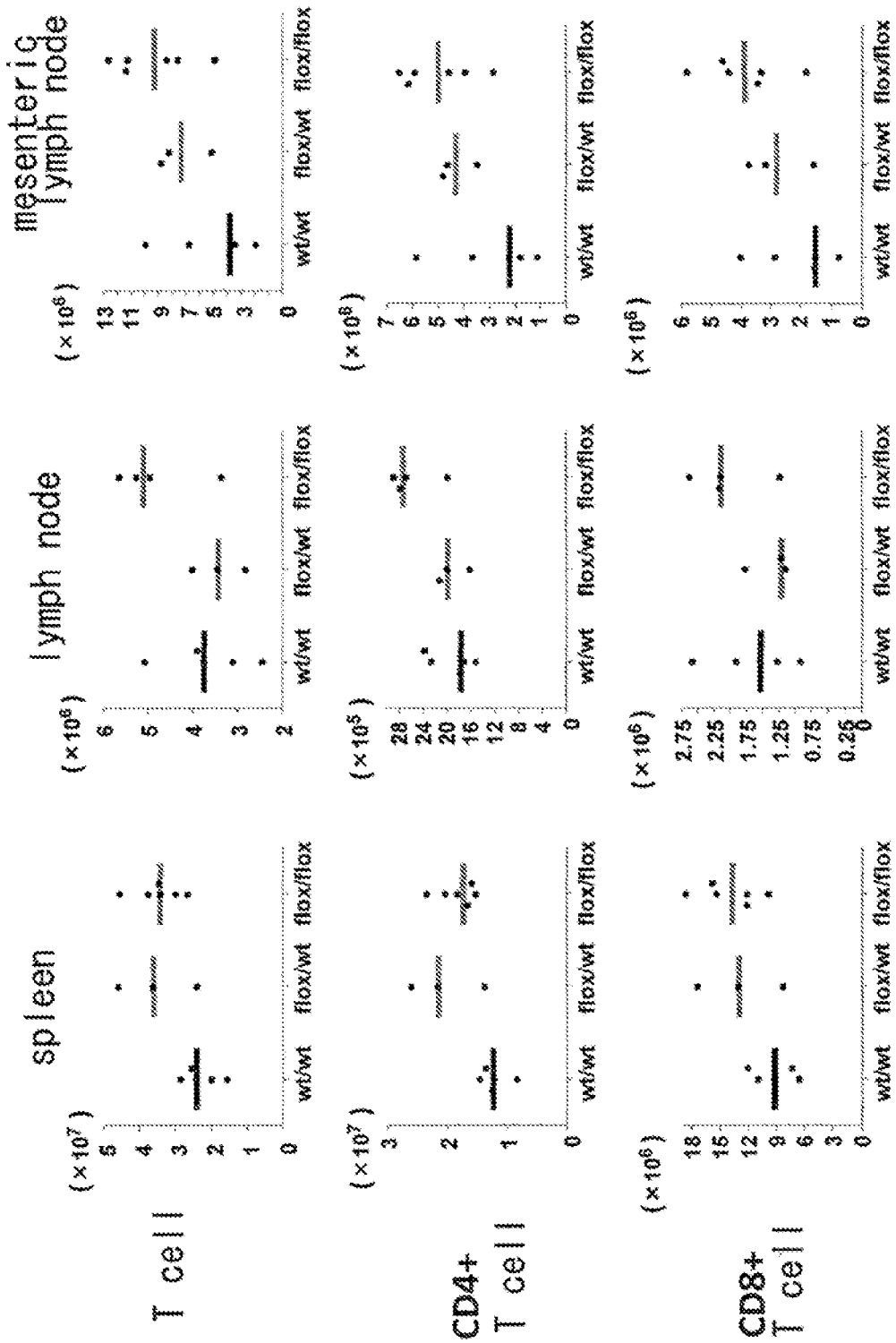

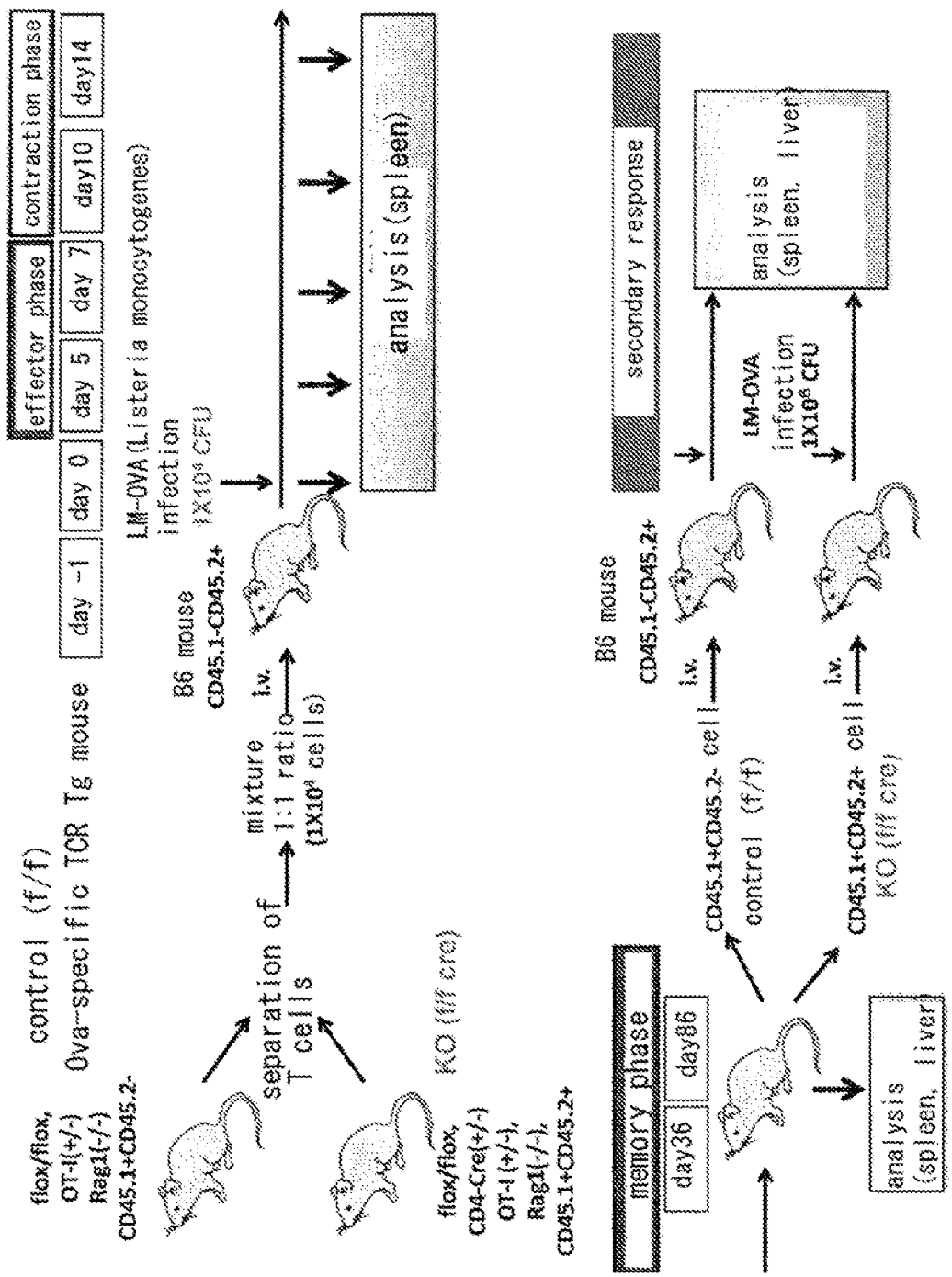
[Fig. 12]

[Fig. 13]
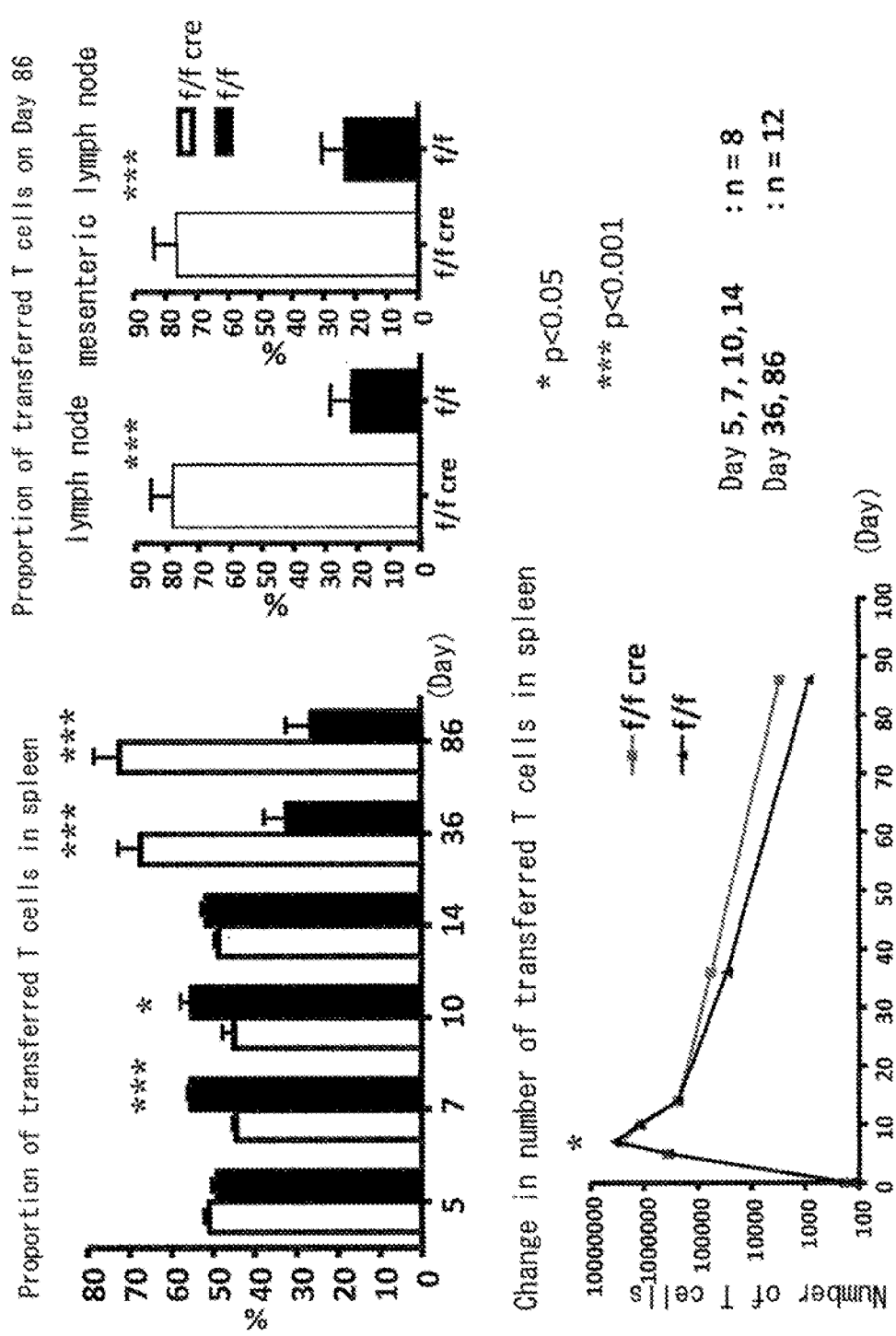

[Fig. 14]
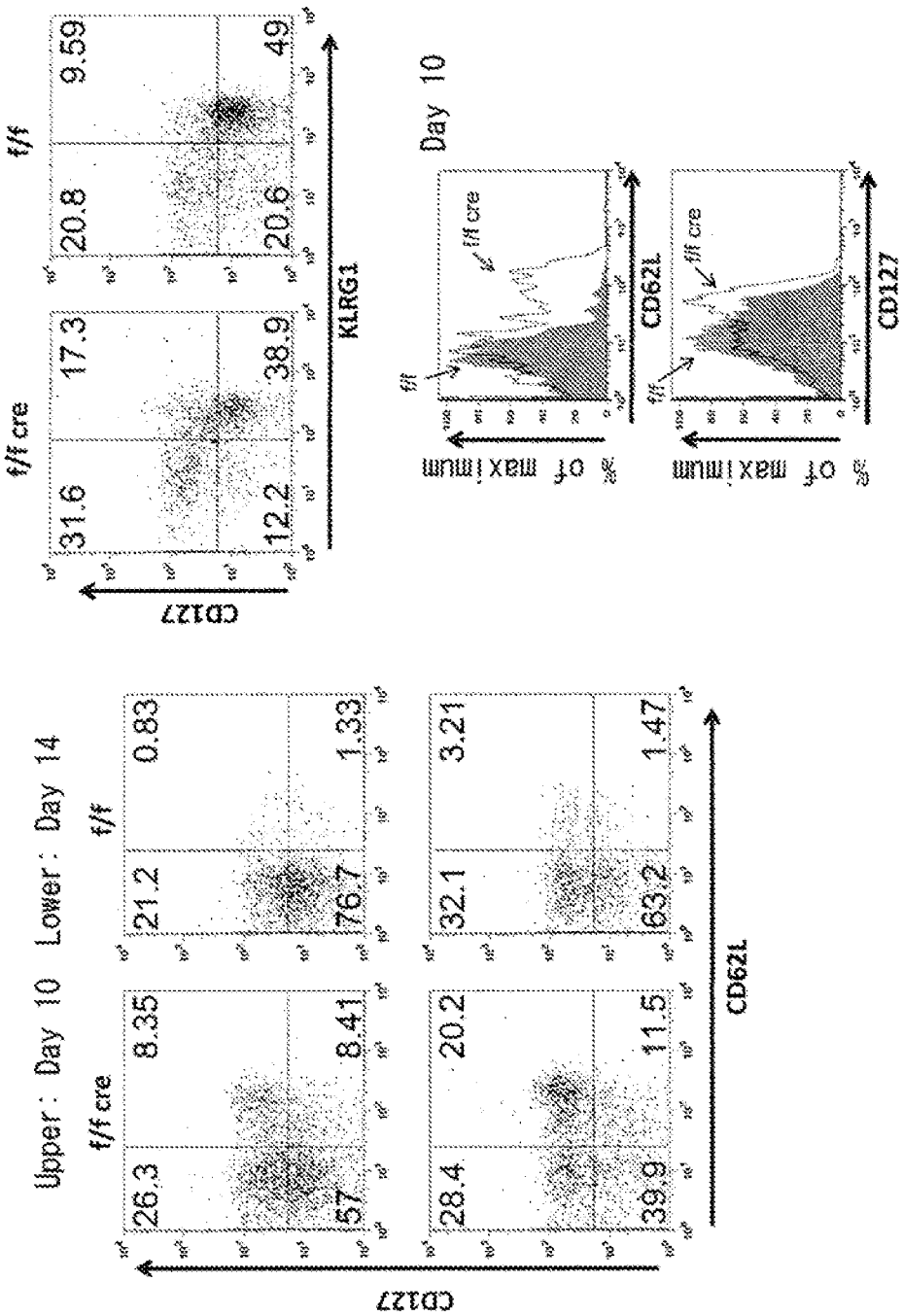

[Fig. 15]
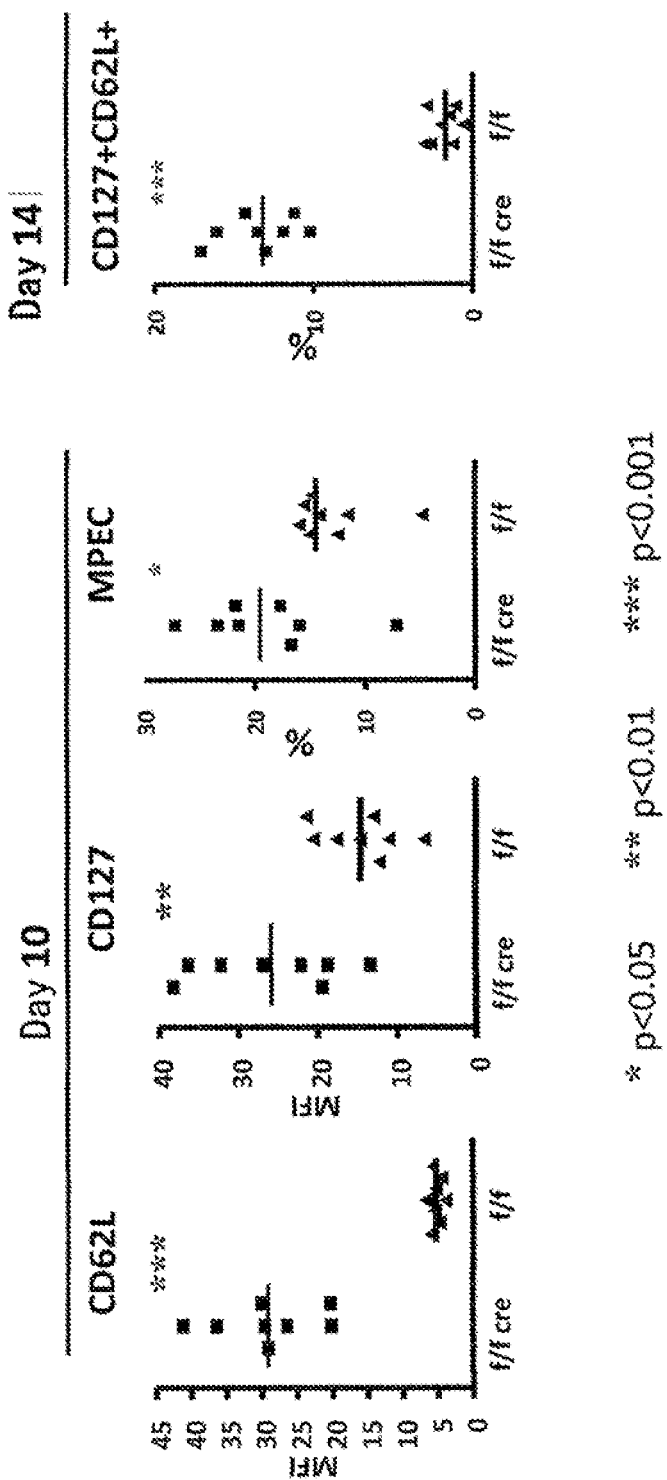

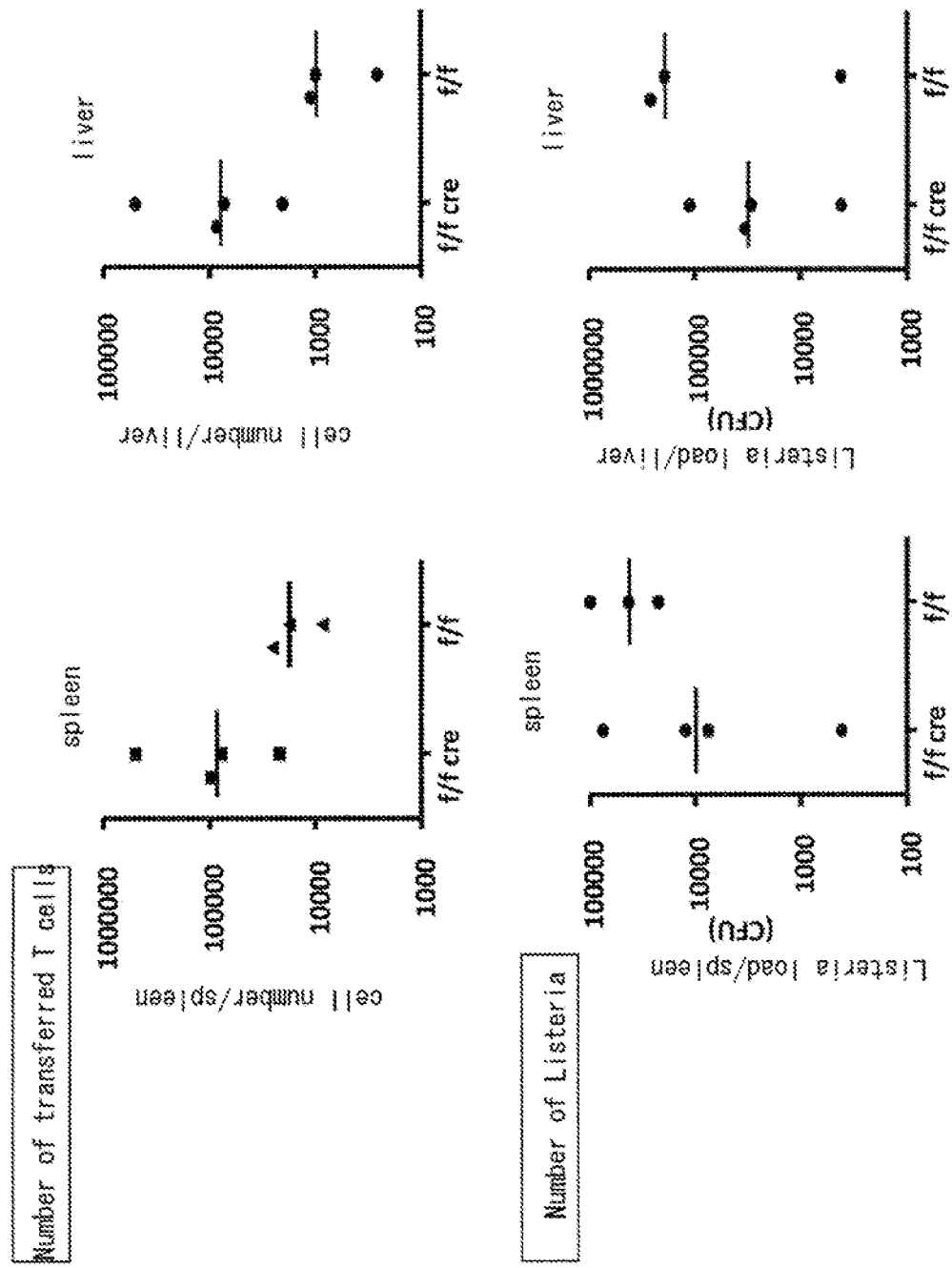
[Fig. 16]

[Fig. 17]
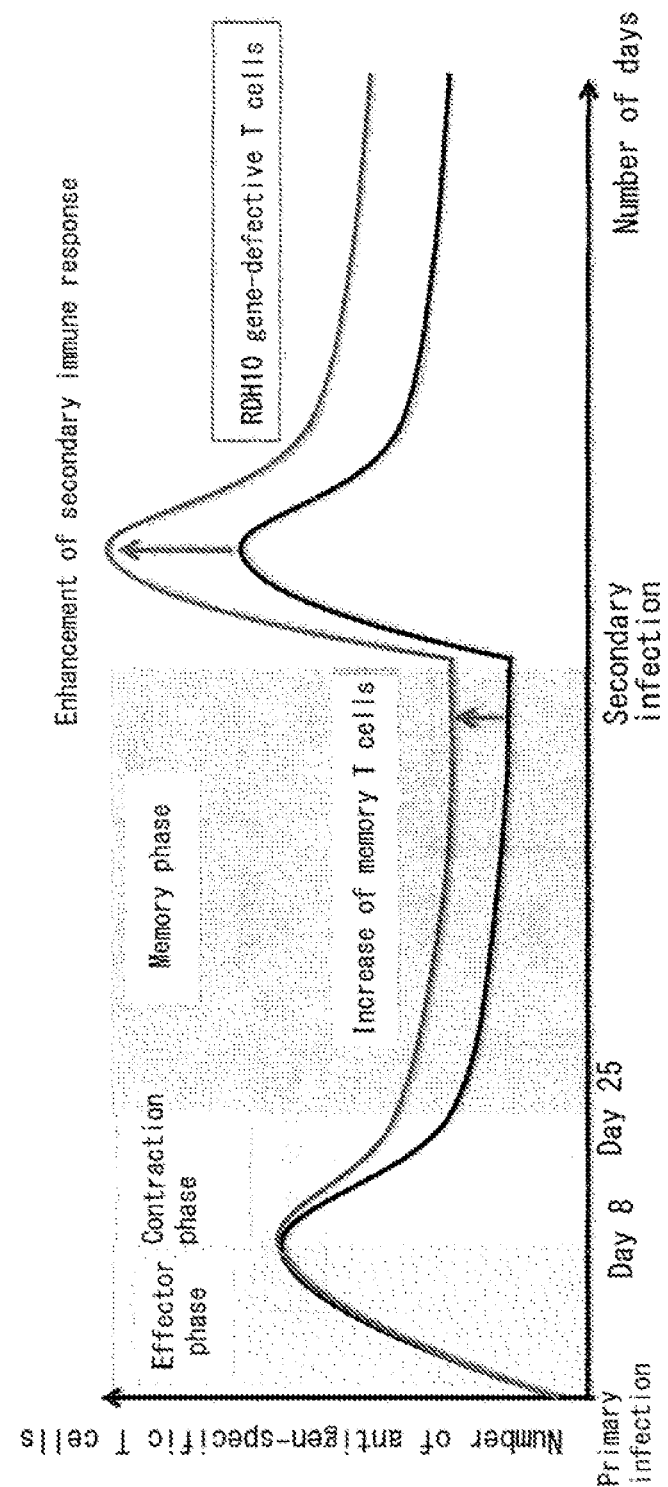

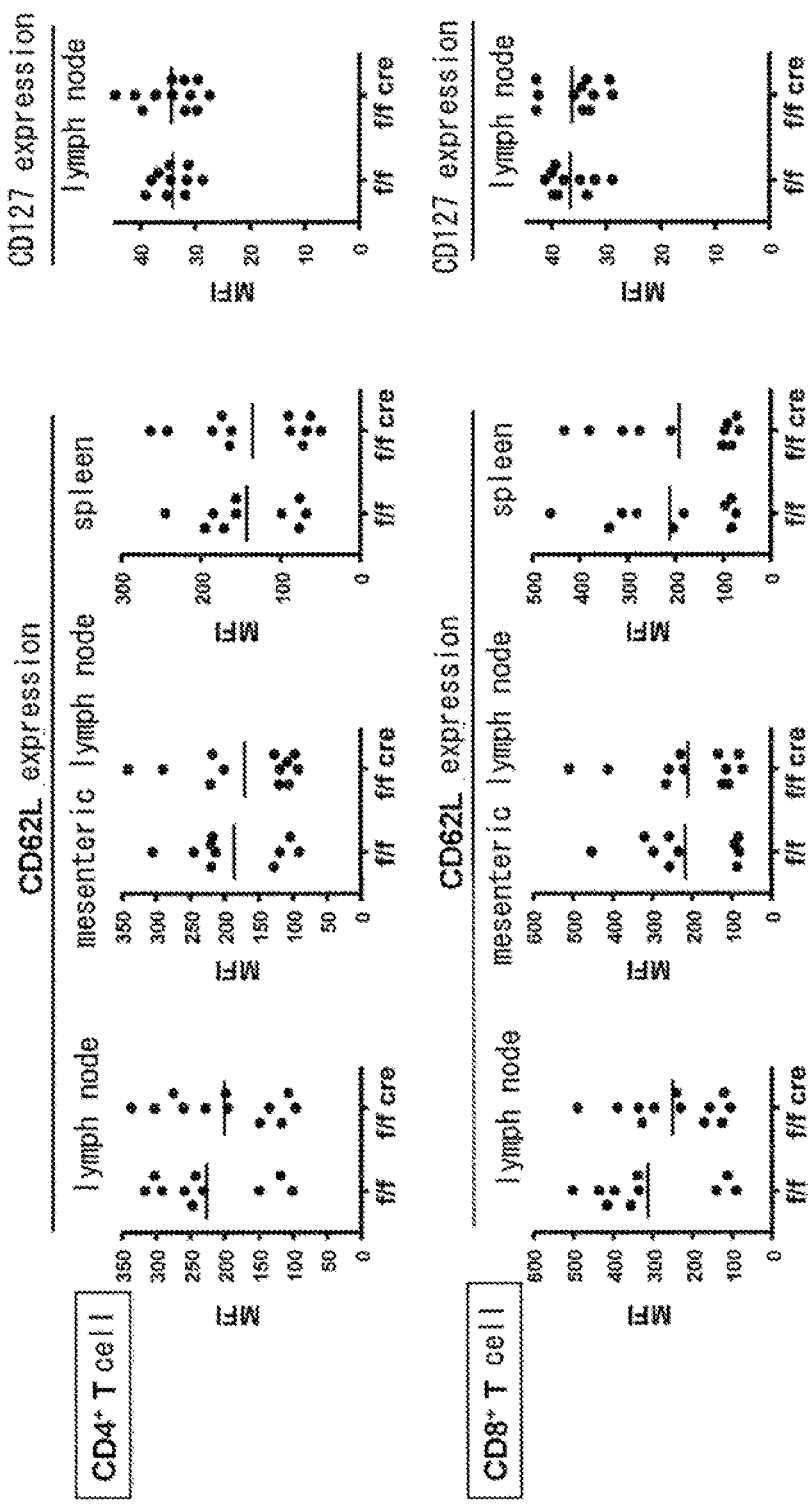
[Fig. 18]

[Fig. 19]
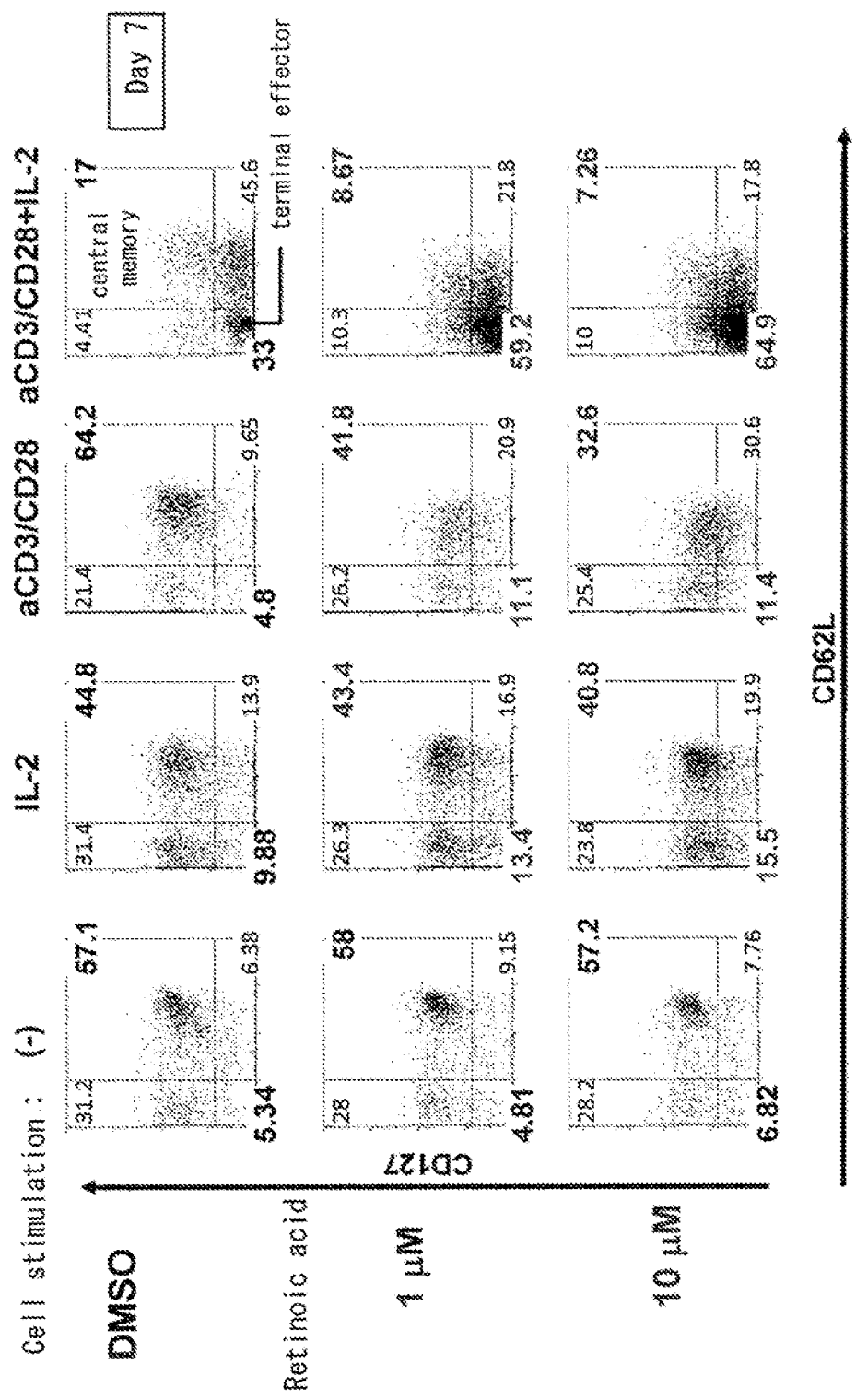

[Fig. 20]
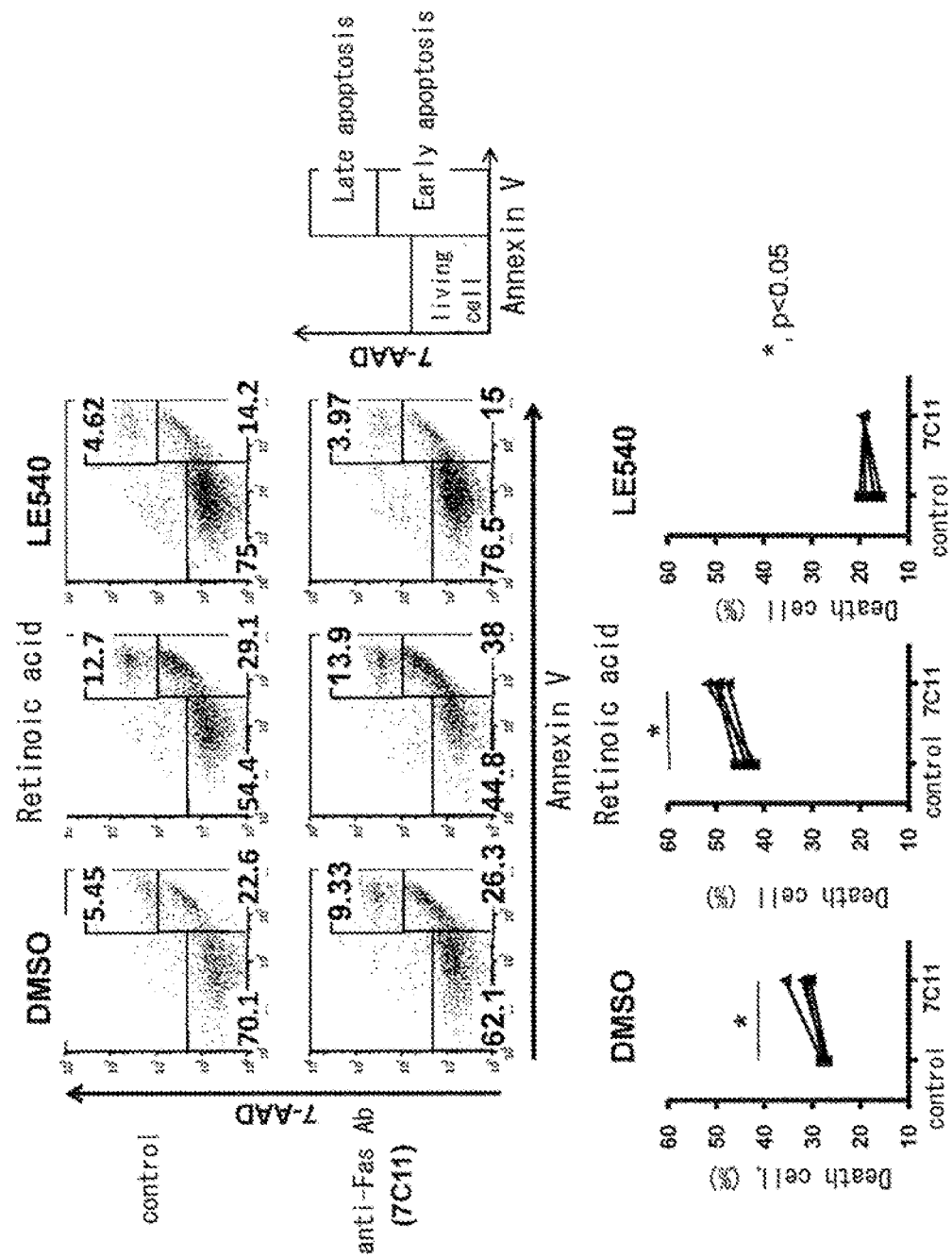

[Fig. 21]
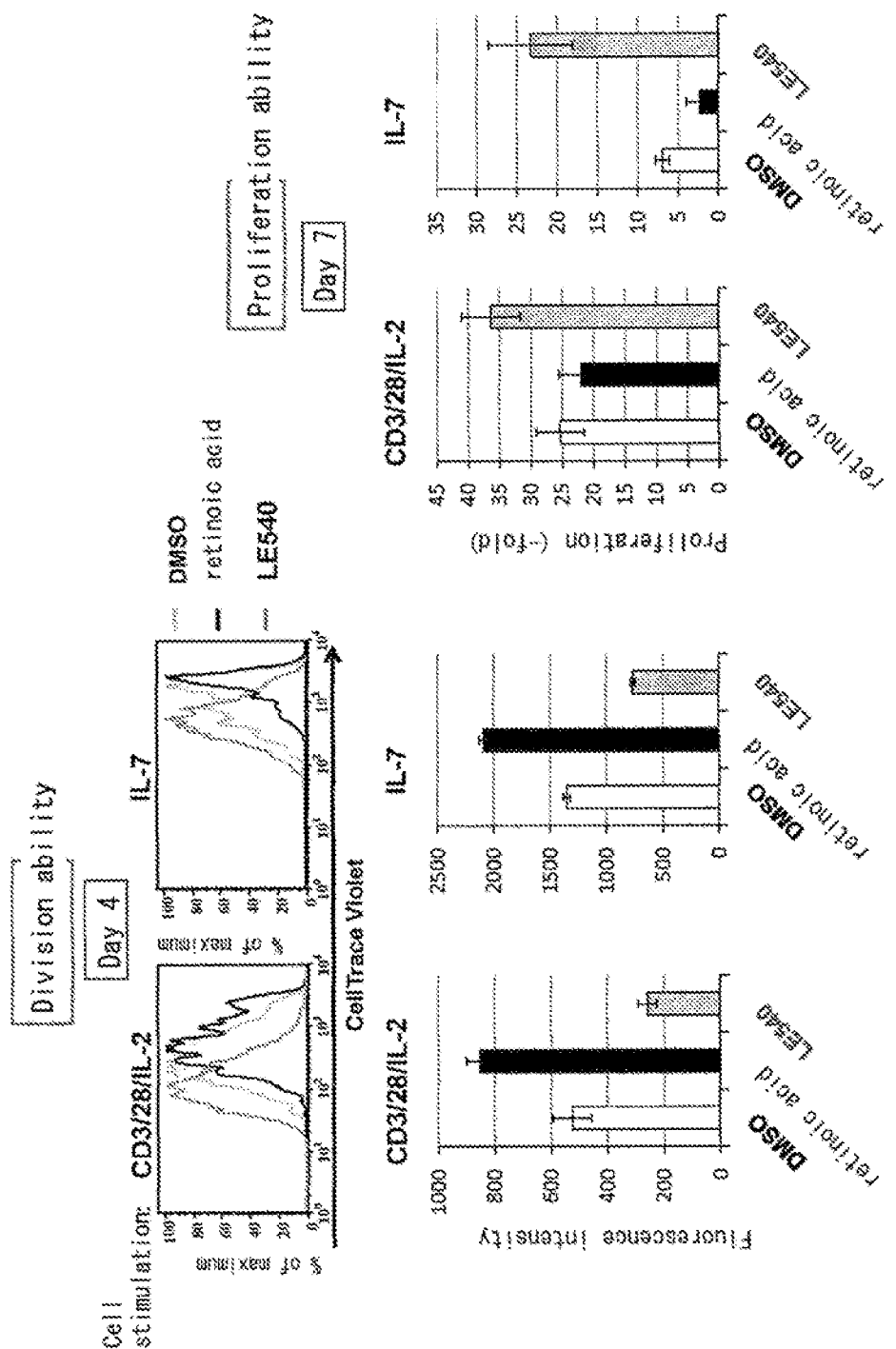

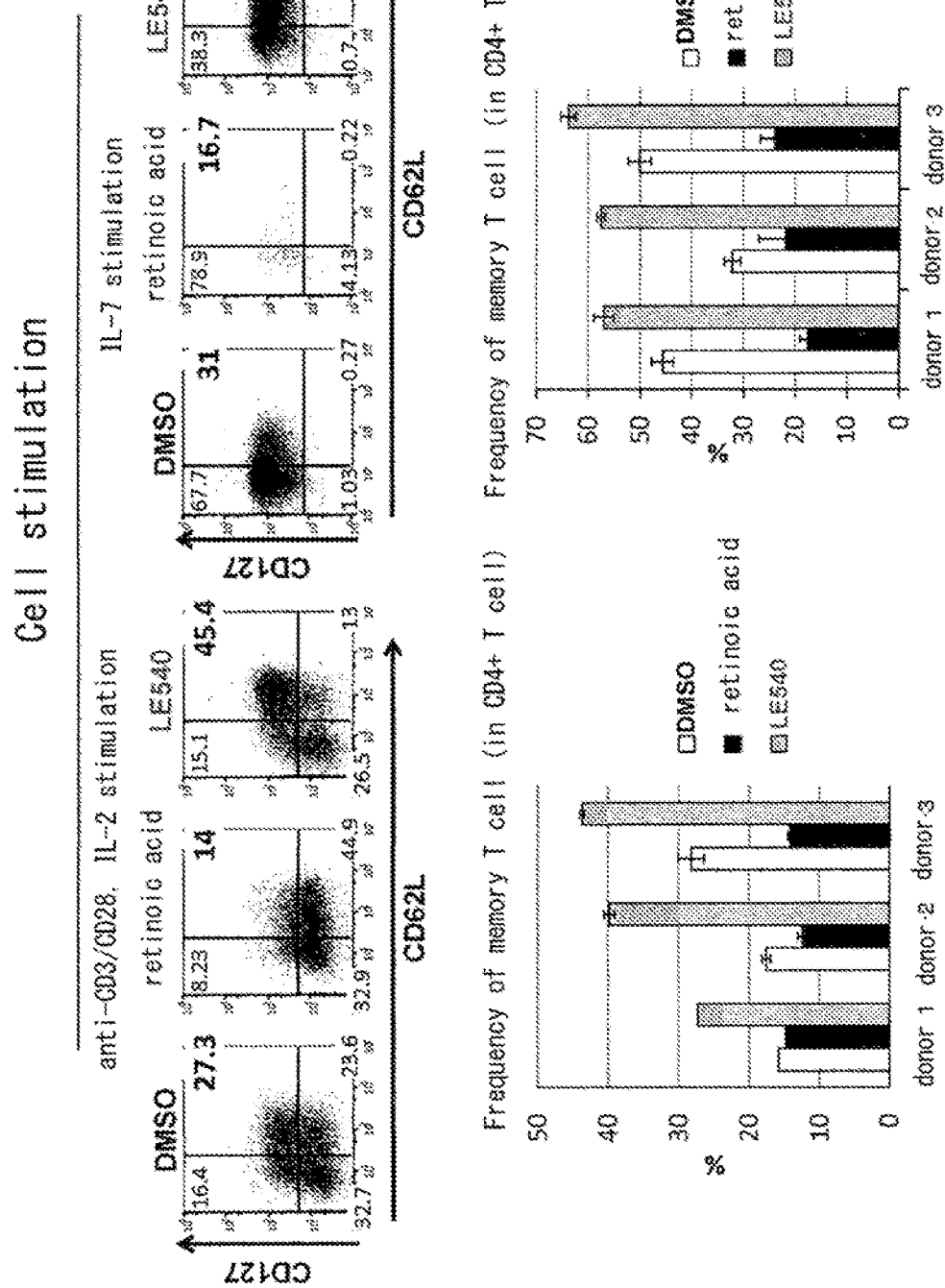
[Fig. 22]

[Fig. 23]
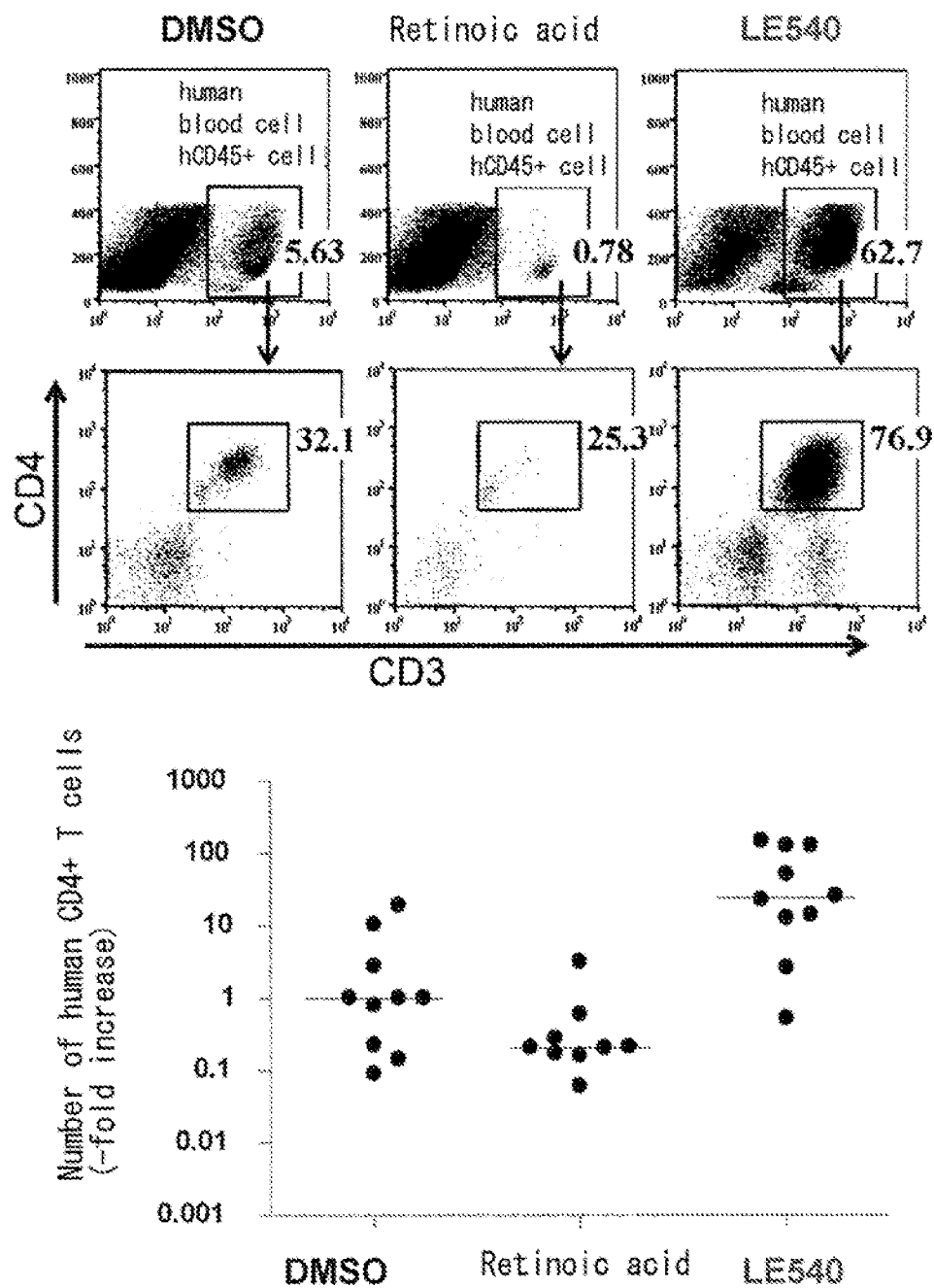

[Fig. 24]
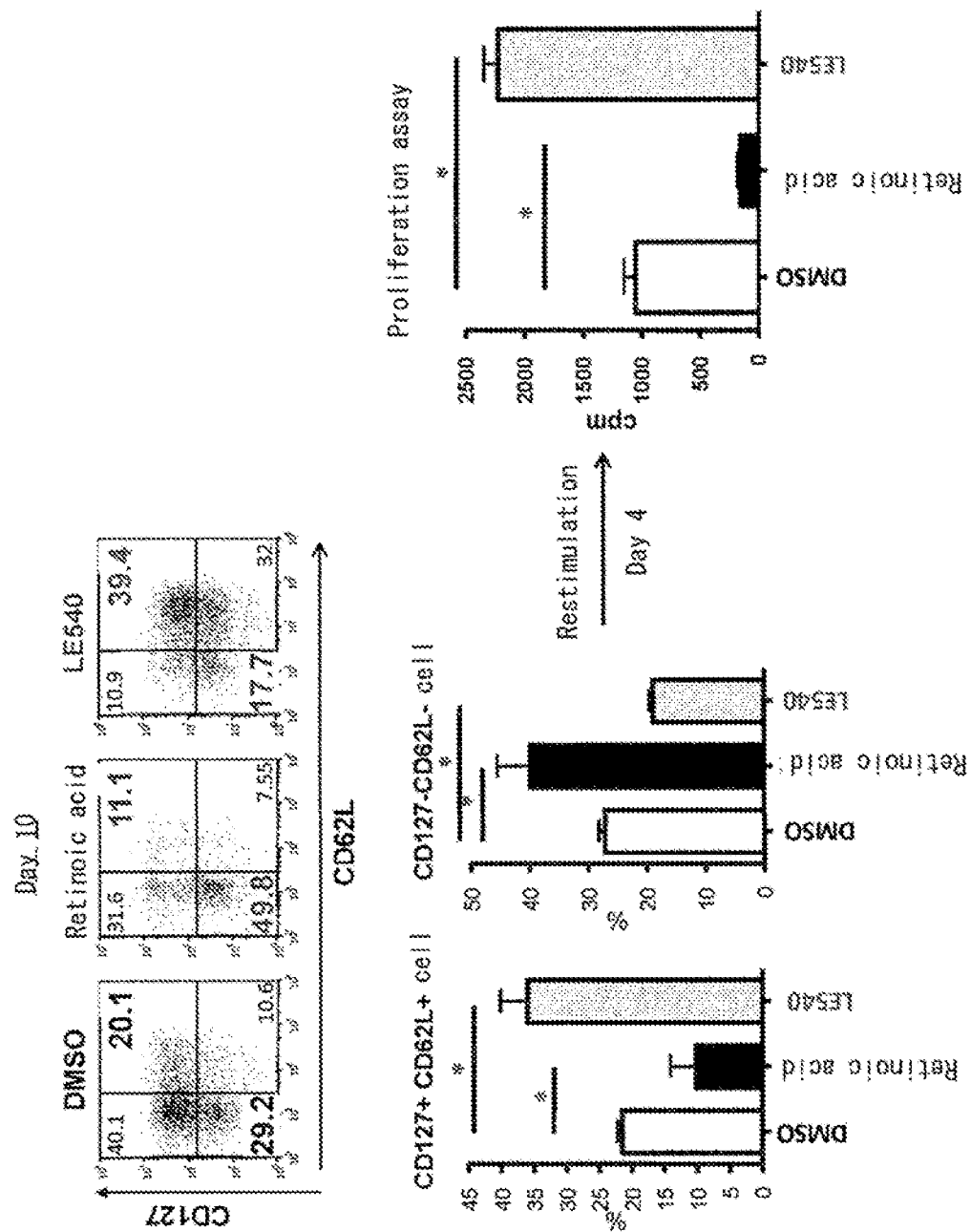

[Fig. 25]
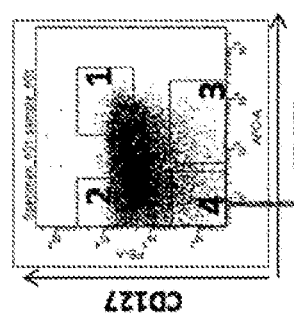
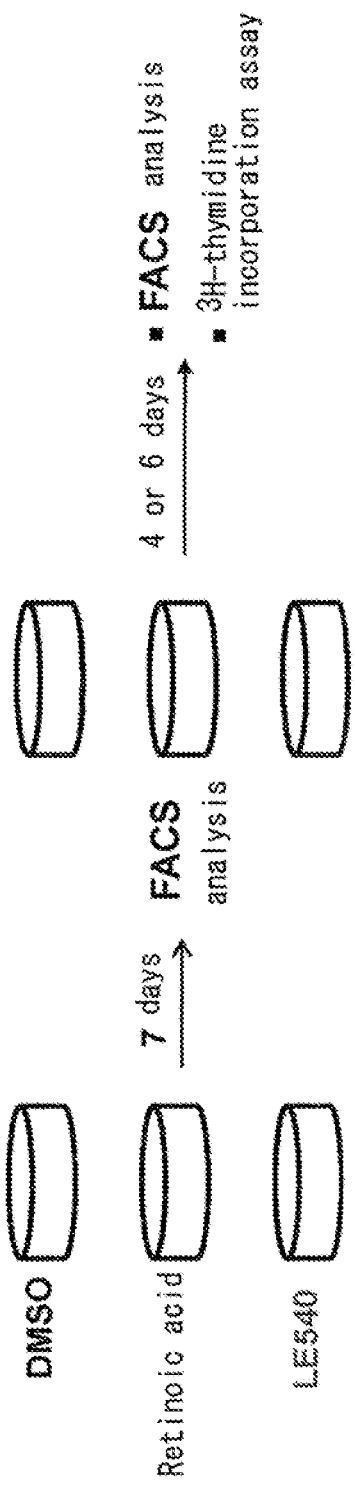

[Fig. 26]
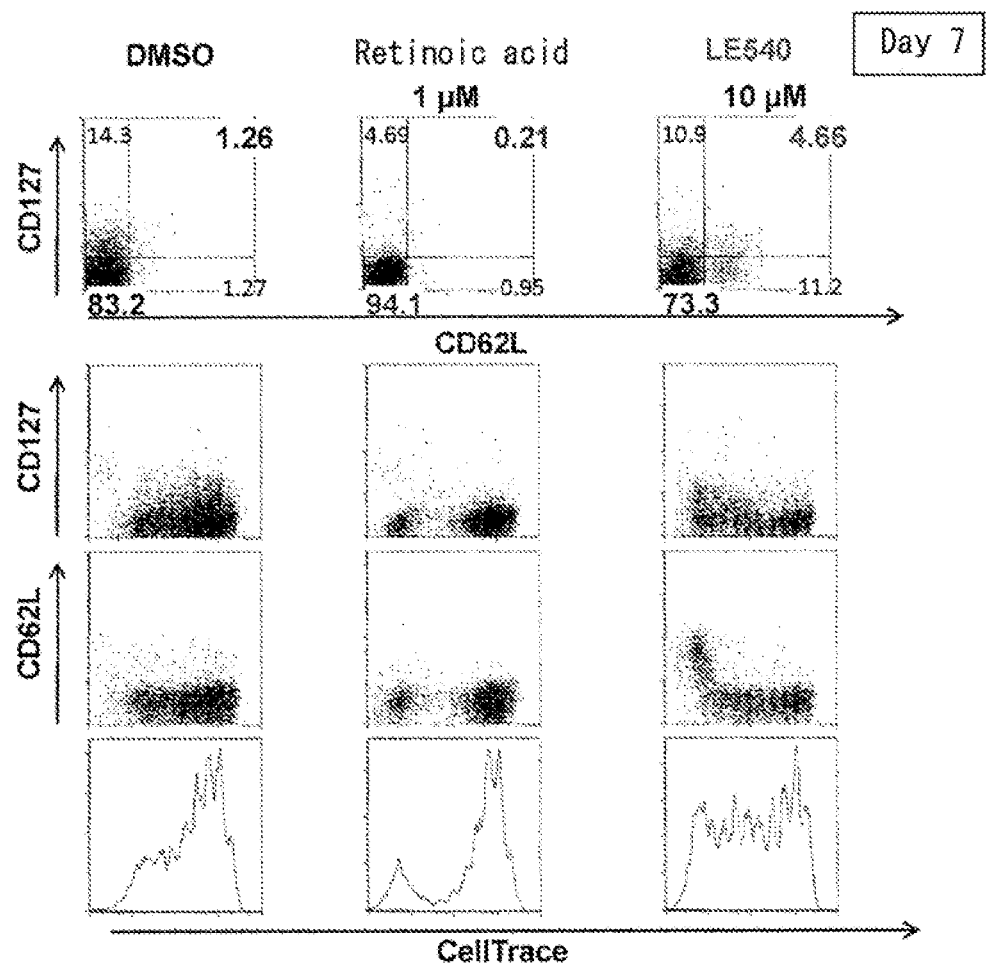

[Fig. 27]
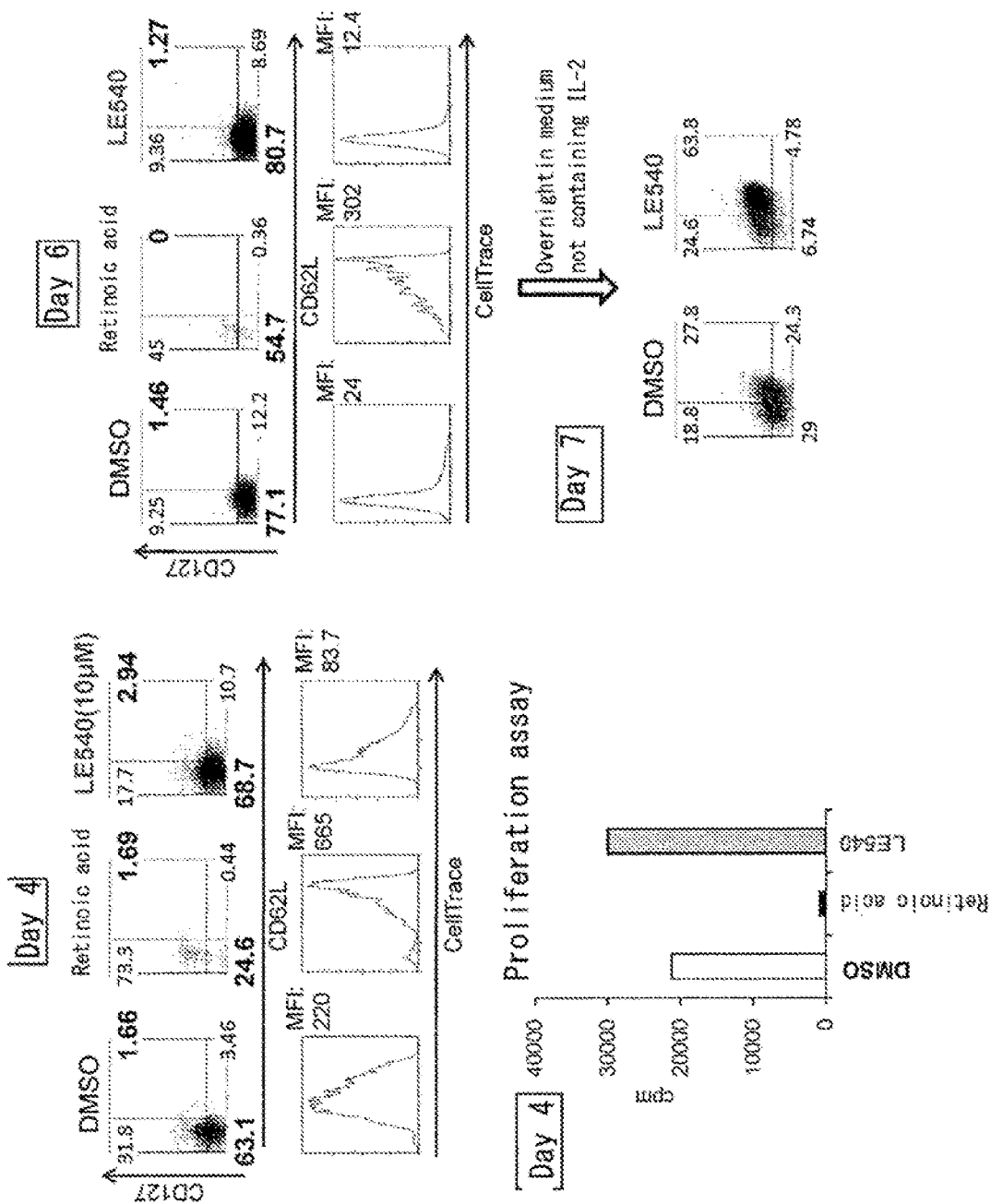

[Fig. 28]
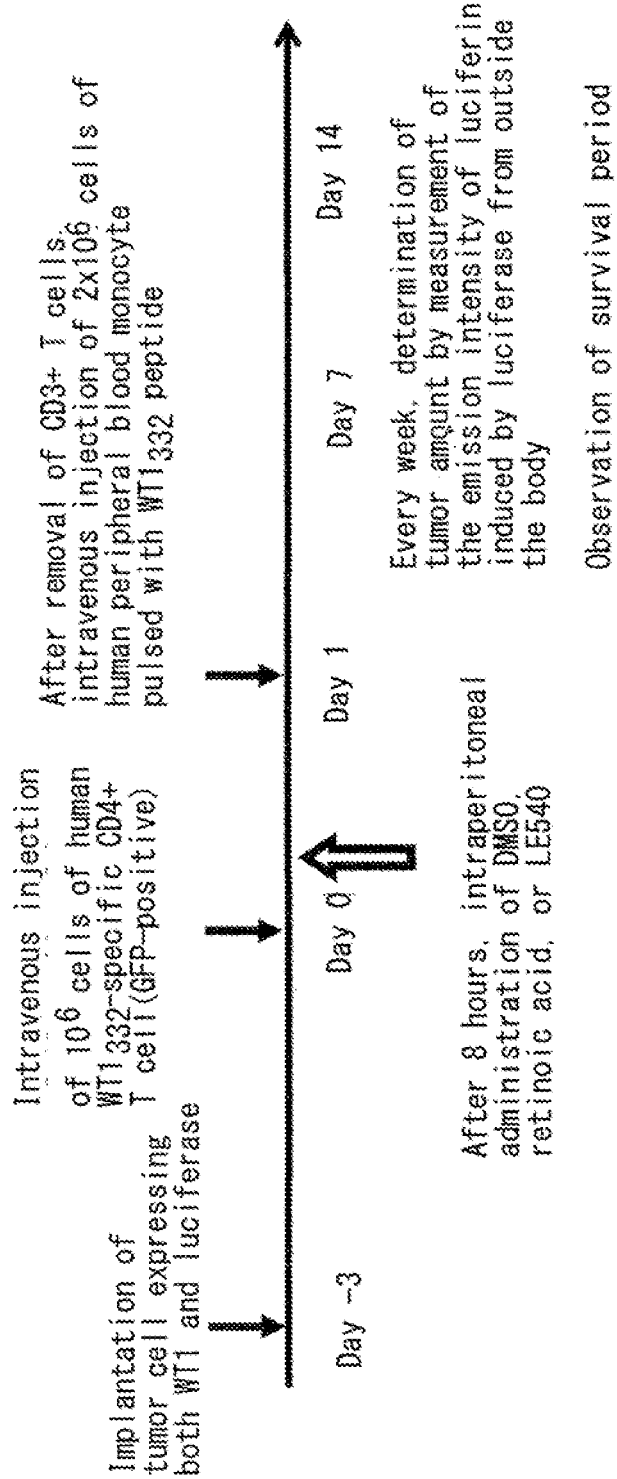

[Fig. 29]
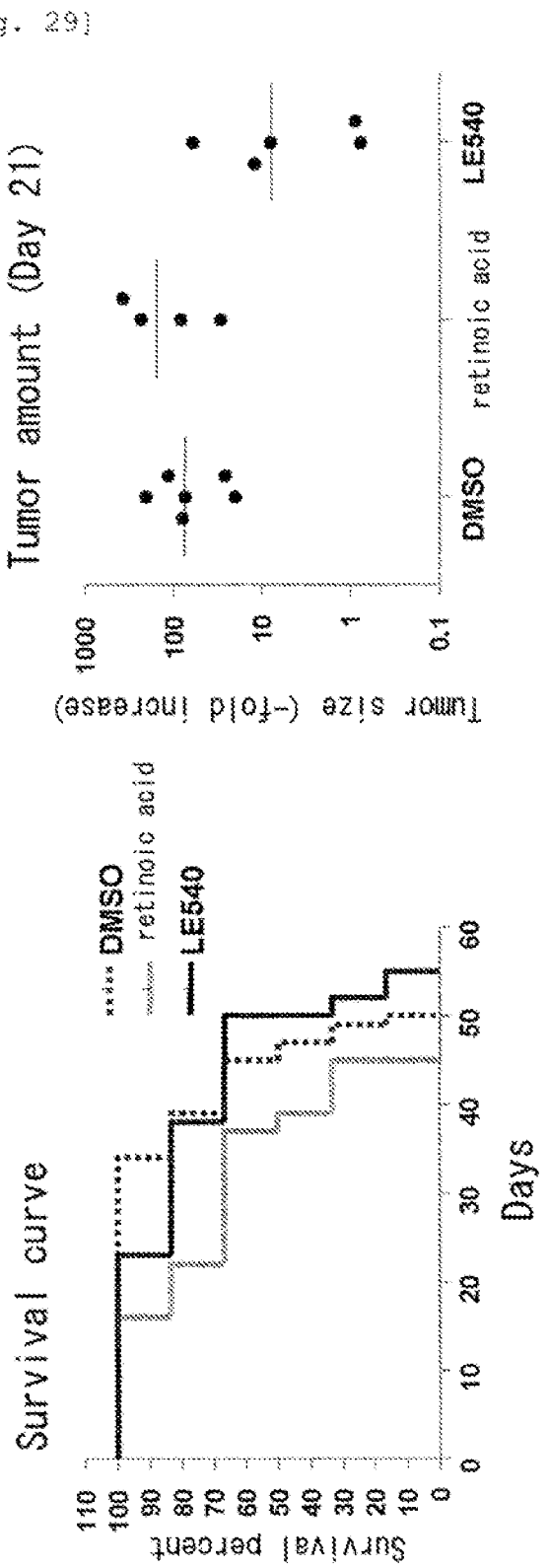

[Fig. 30]
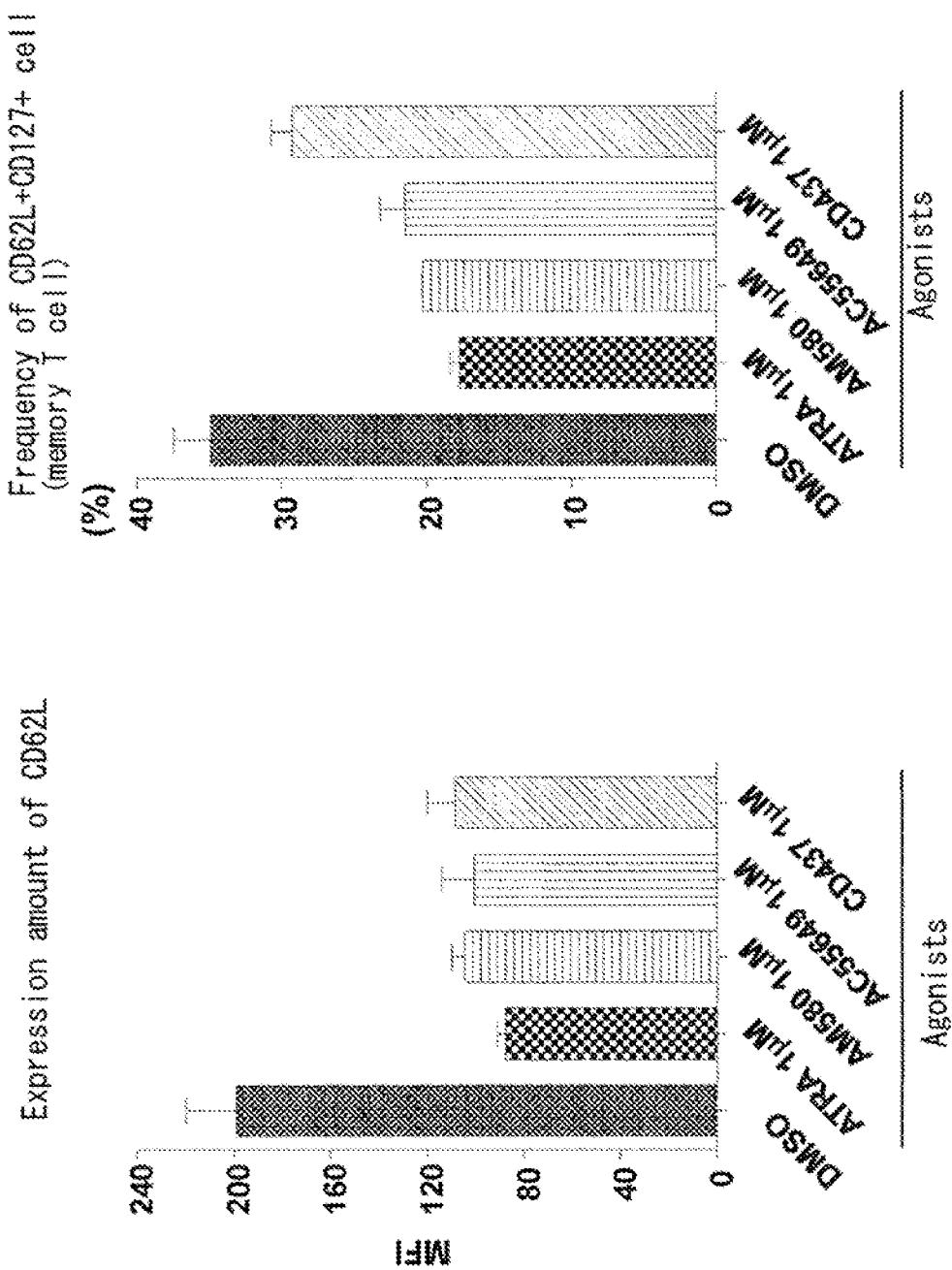

[Fig. 31]
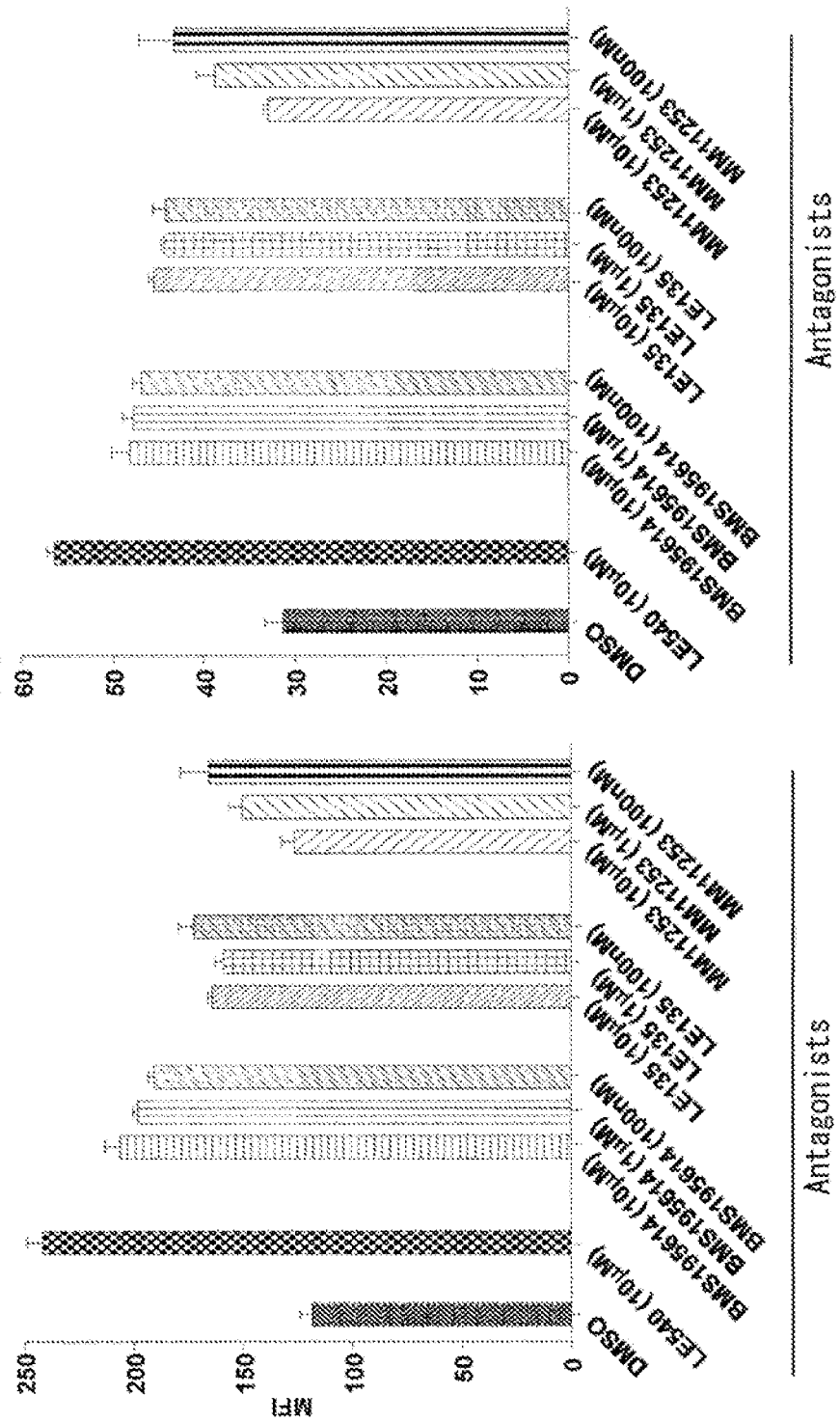

[Fig. 32]
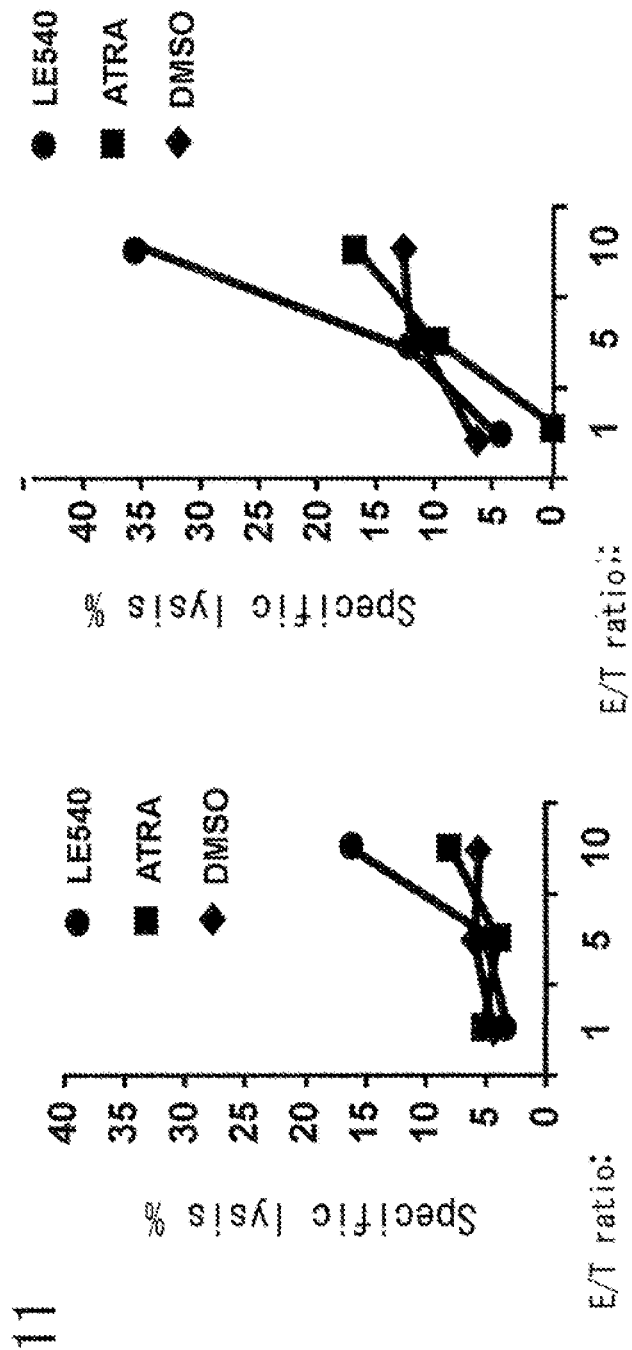

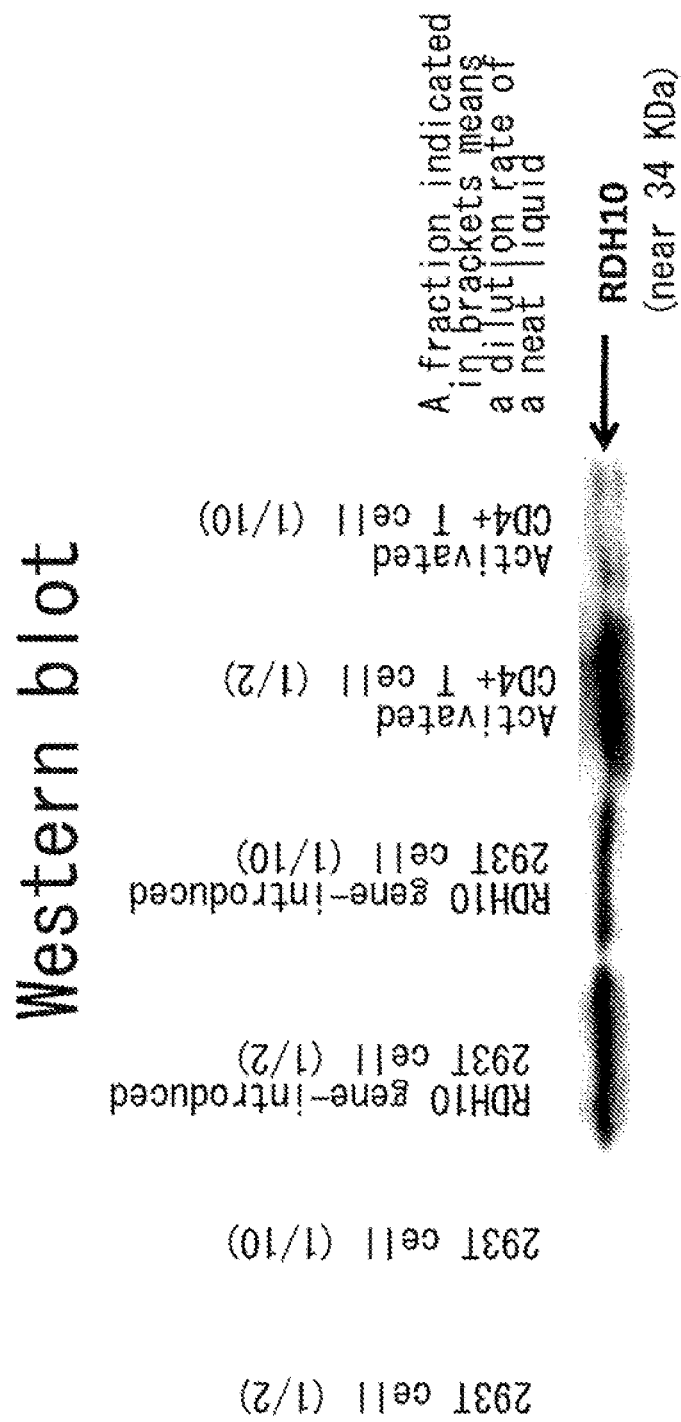
[Fig. 33]

[Fig. 34]
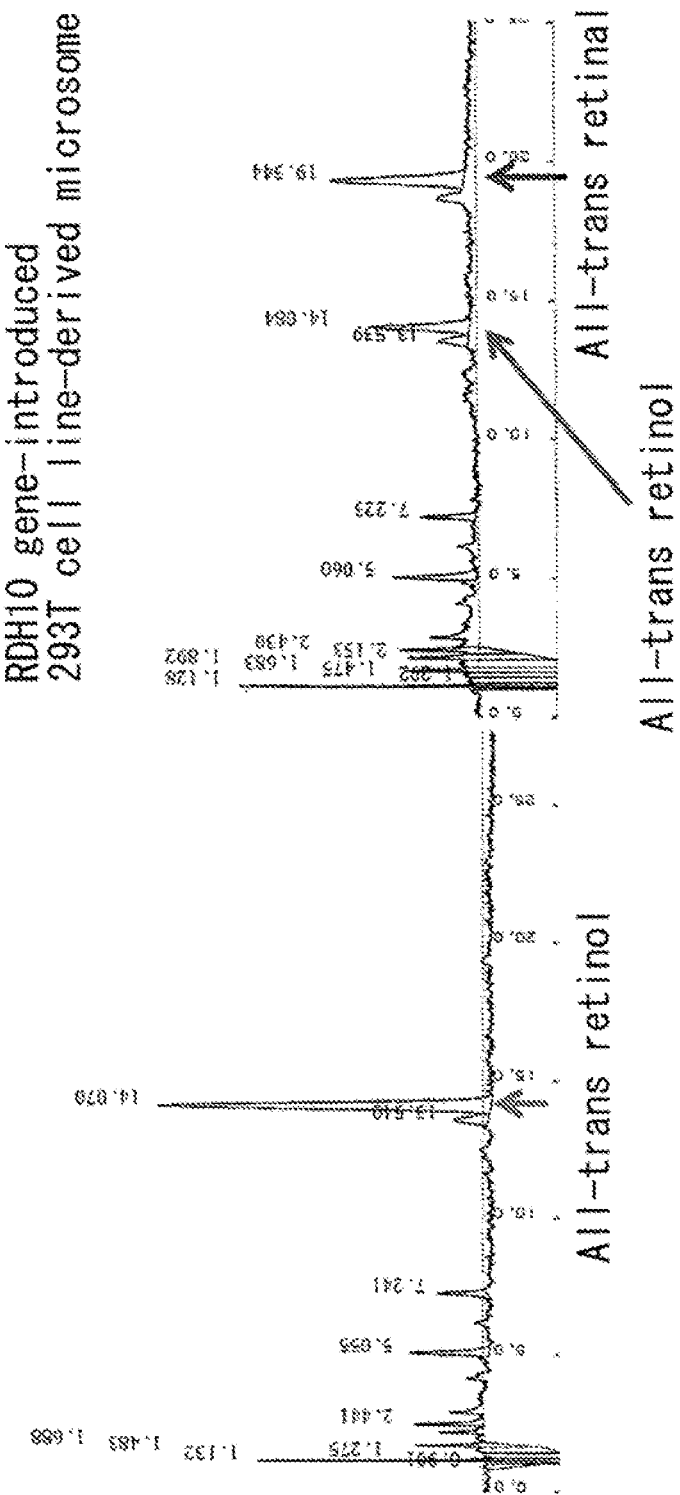

[Fig. 35]
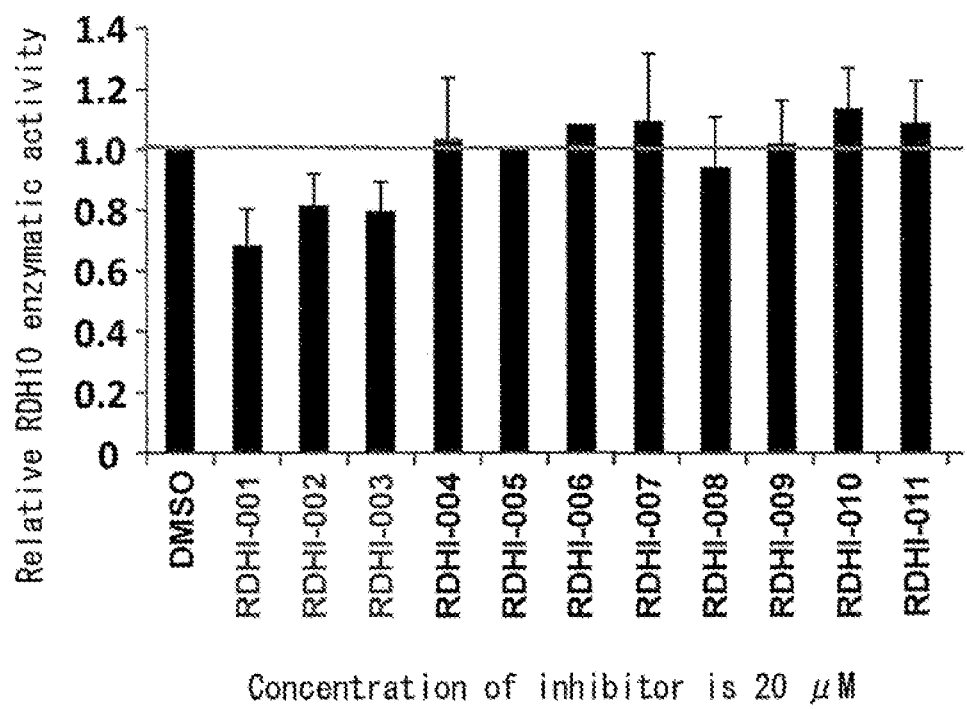

[Fig. 36]
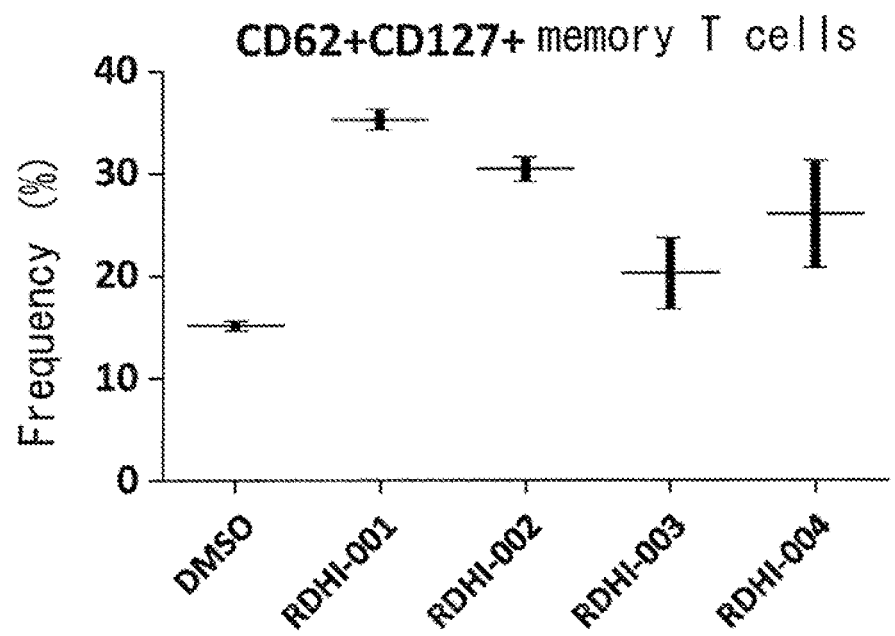

[Fig. 37]
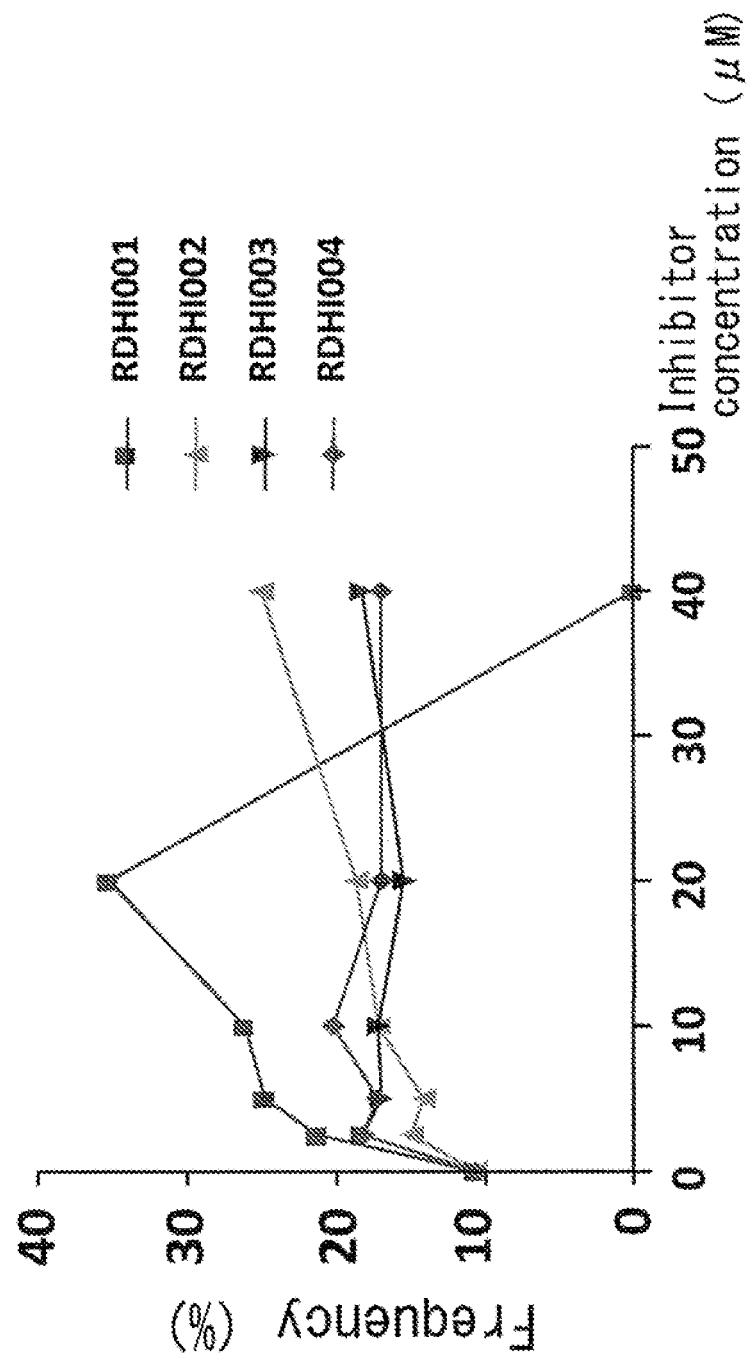

[Fig. 38]
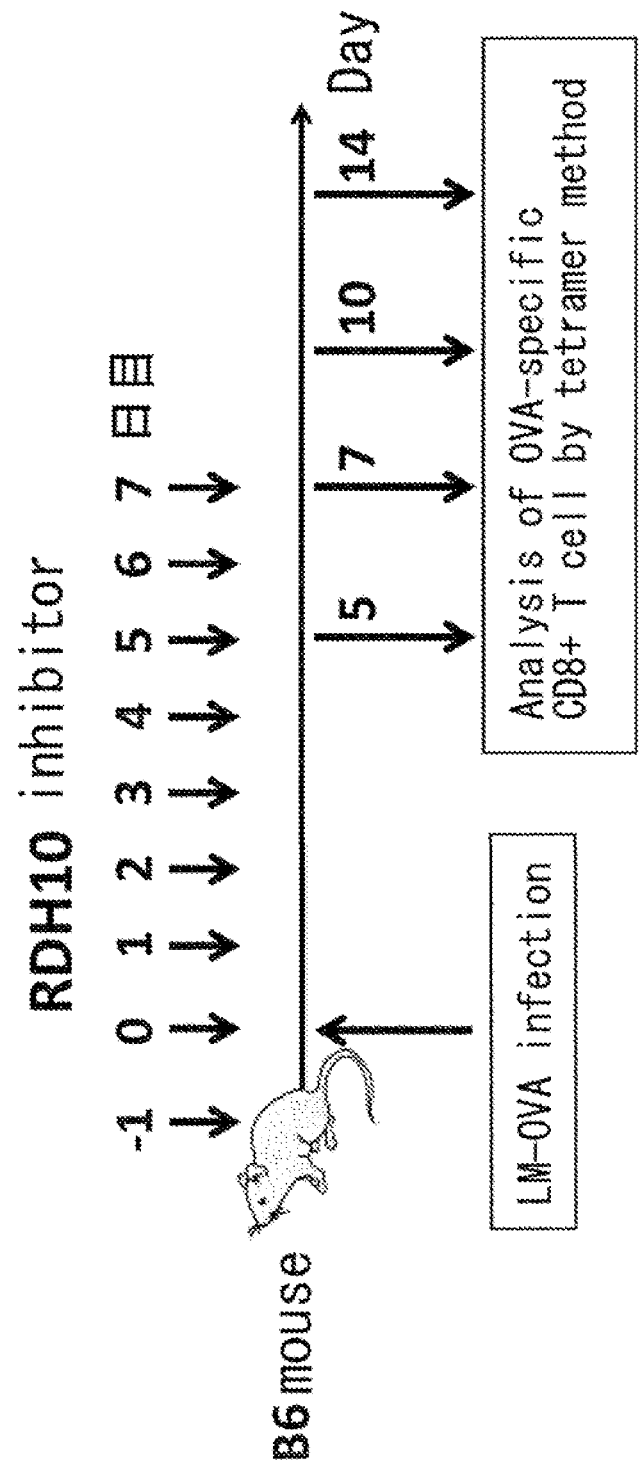

[Fig. 39]
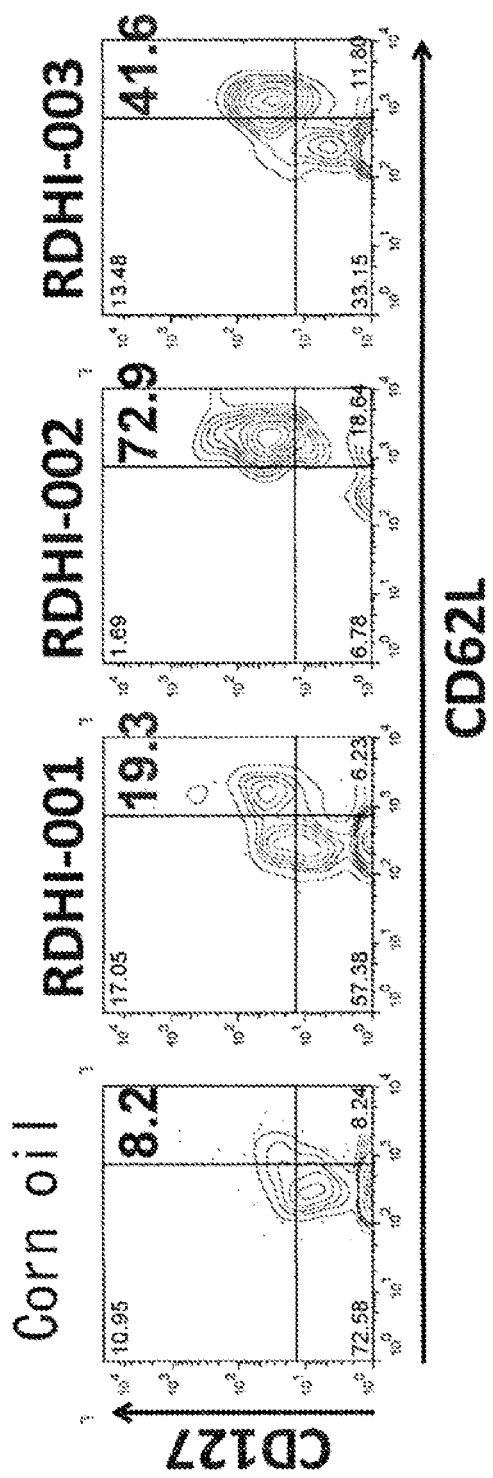

[Fig. 40]
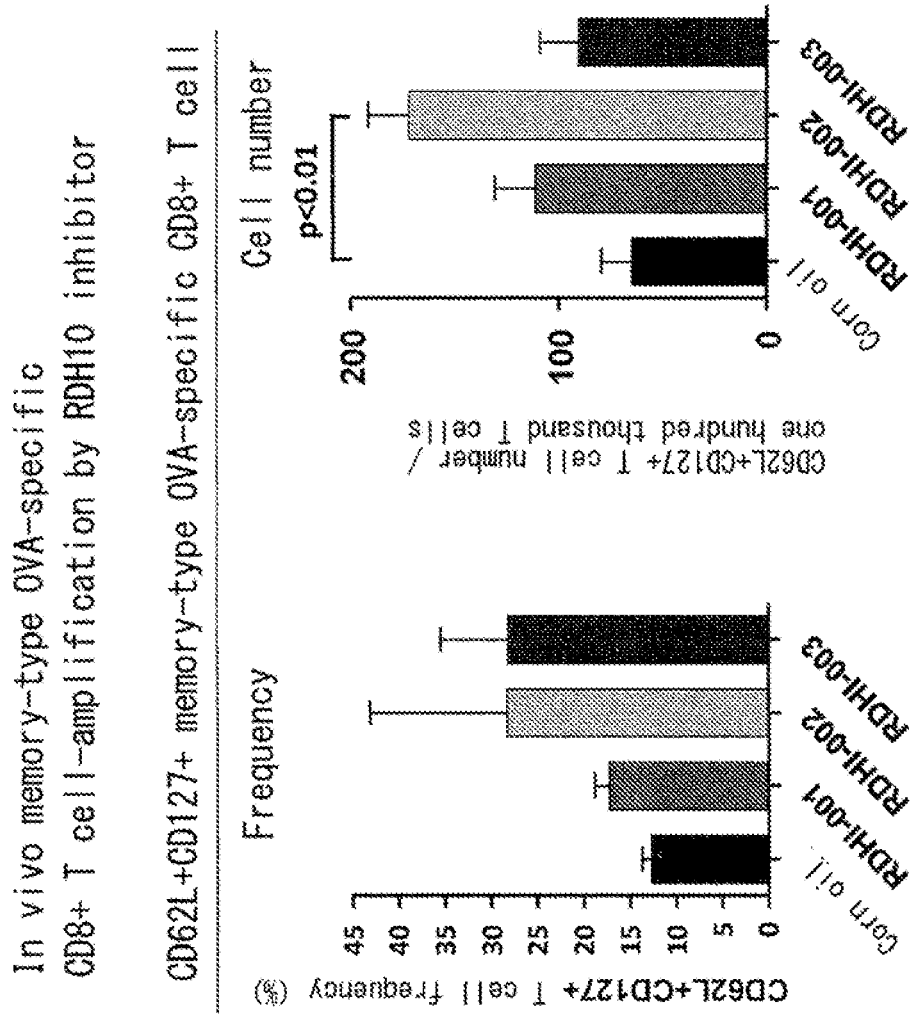

[Fig. 41]
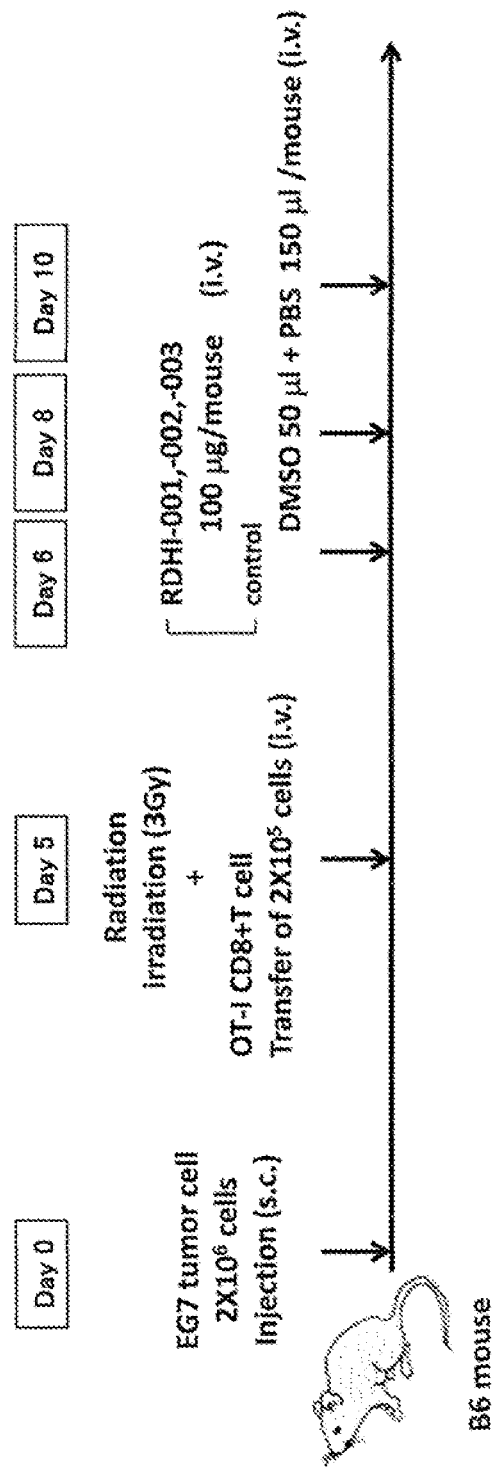

[Fig. 42]
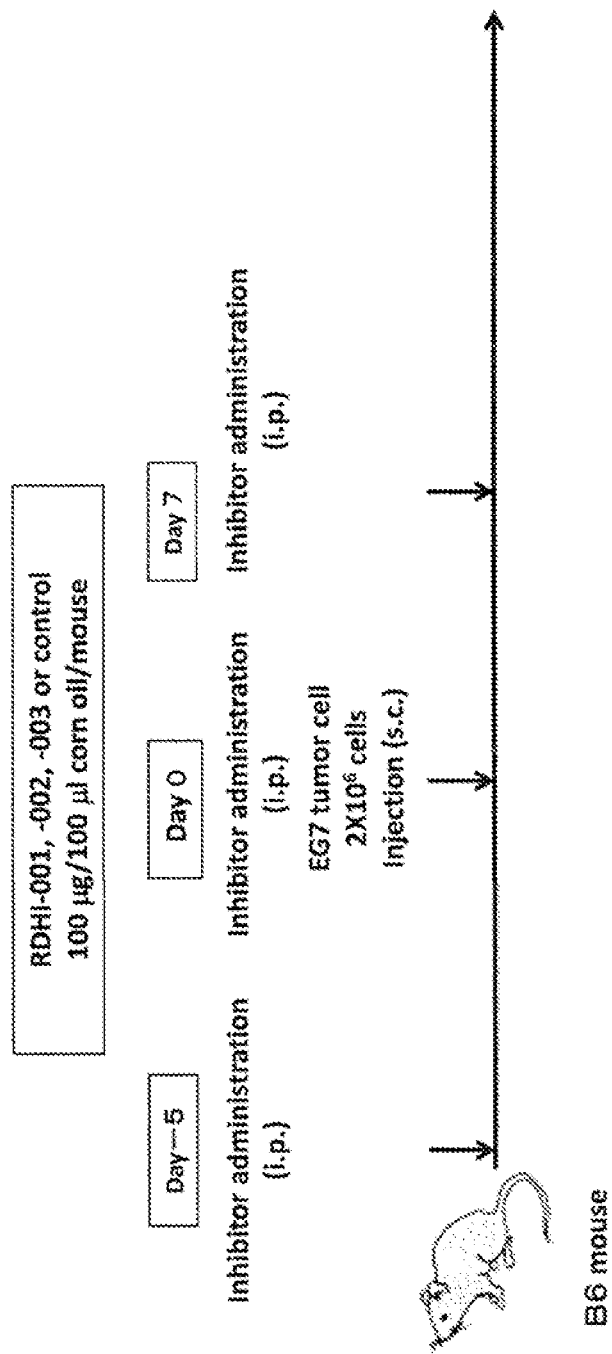

[Fig. 43]
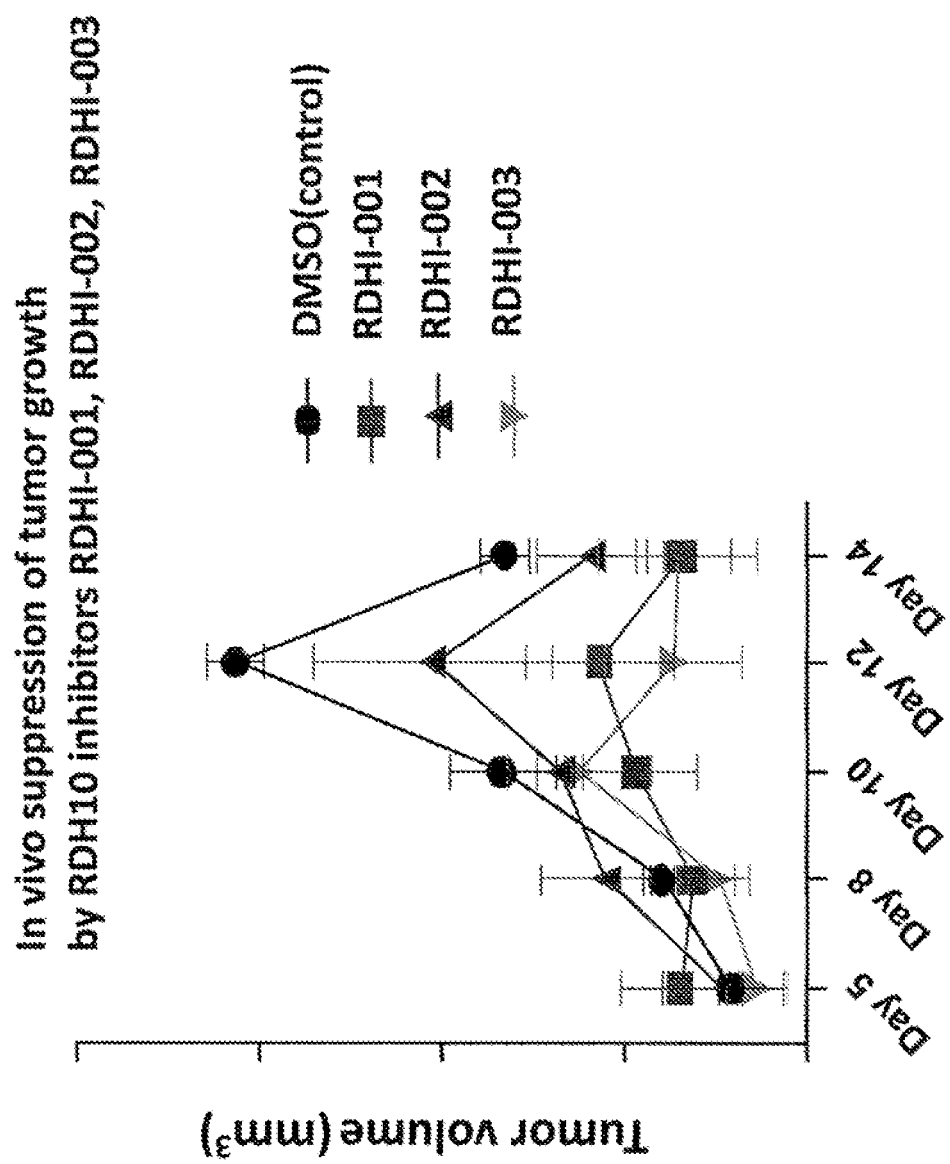

[Fig. 44]
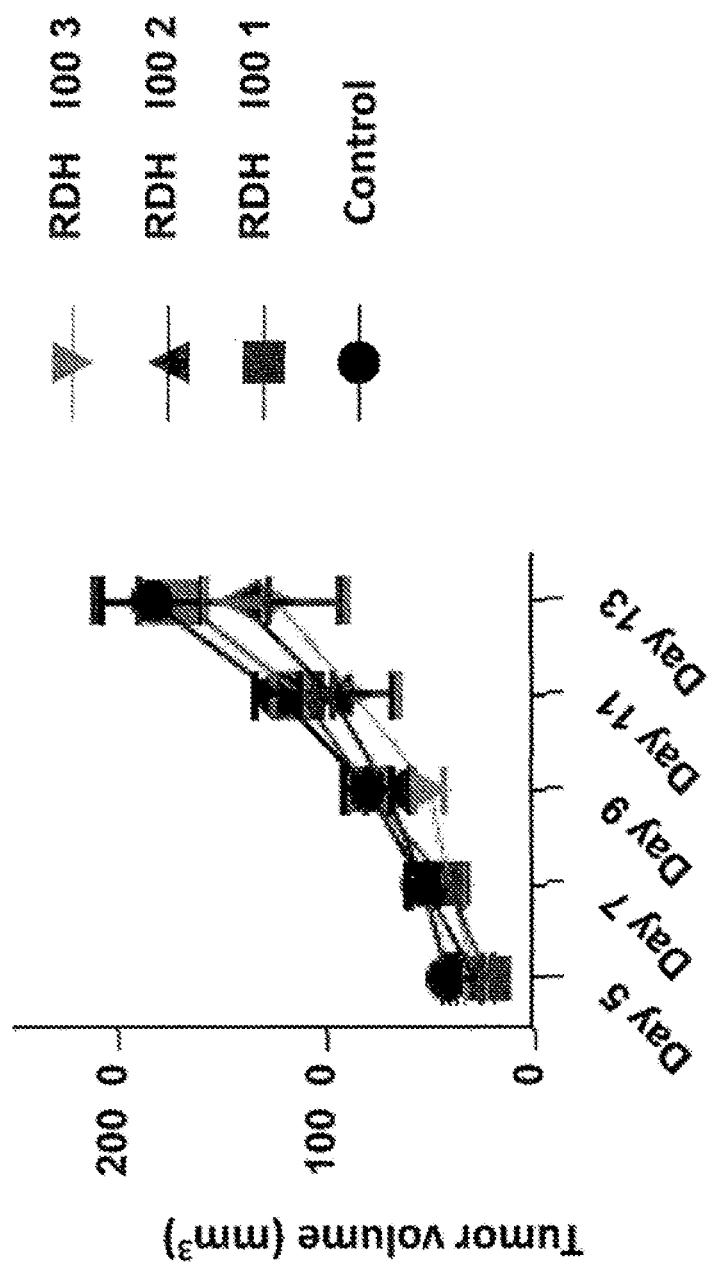

METHOD FOR MODIFYING T CELL POPULATION

TECHNICAL FIELD

The present invention relates to a method for modulating differentiation of an immune cell, in particular a T cell, to modify a T cell population.

BACKGROUND ART

Immunotherapy is generally a method of treating diseases which comprises activating the immune system of a patient by various means or introducing immune cells activated outside the body of a patient into the body of the patient. Different types of immunotherapy including an immune cell therapy, a peptide vaccine therapy, a cytokine therapy, and an antibody therapy have been developed.

In recent years, it has been found that stimulation of immune cells (in particular, antigen-presenting cells or T cells) with a partial peptide derived from WT1 which is a cancer gene product (WT1 peptide) may lead to induction of tumor-specific cytotoxic T cells (CTL) or activation of helper T cells (Patent Literature 1-4 and Non-patent Literature 1), and immunotherapy using WT1 peptide vaccine has been studied toward practical use.

However, only a few types of immunotherapy including the WT1 peptide vaccine are shown to have efficacy in clinical trials. Immunotherapy may not produce adequate effect depending on status of patient's immunity (immune suppression, differentiation stage and activity of immune cells). Thus there is a need to develop a method for enhancing the effect of immunotherapy.

CITATION LIST

Patent Literature

Patent Literature 1: WO2003/106632
Patent Literature 2: WO2005/095598
Patent Literature 3: WO2007/097358
Patent Literature 4: WO2012/046730

Non-Patent Literature

Non-patent Literature 1: Oka Y et al., Immunogenetics. 2000 February; 51(2): 99-107

SUMMARY OF INVENTION

Problem to be Solved by the Invention

An objective of the present invention is to provide a substance and a method that can modify the status of immunity in a subject to enhance the effect of immunotherapy.

Solutions to the Problems

Inventors of the present invention found that the proportion of memory T cells in a T cell population was increased by modulating a retinoid metabolic pathway or a retinoic acid signaling system, and thereby an immune response in a subject may be enhanced. Thus the present invention was completed.

The present invention provides:

(1) A method of increasing the proportion of memory T cells in a T cell population, the method comprising a step of adding a modulator of a retinoid metabolic pathway and/or a modulator of a retinoic acid signaling system to the T cell population (hereinafter, also referred to as "the memory T cell proportion-increasing method of the present invention");

(2) the method according to (1), wherein the modulator is an inhibitor of the retinoid metabolic pathway and/or an inhibitor of the retinoic acid signaling system;

(3) the method according to (2), wherein the inhibitor inhibits conversion of retinol to retinal, conversion of retinal to retinoic acid, conversion of β-carotene to retinal, conversion of β-carotene to β-apocarotenal, or conversion of β-apocarotenal to retinal and retinoic acid;

(4) the method according to (2) or (3), wherein the inhibitor is an RNA molecule that suppresses expression of a gene encoding an enzyme selected from the group consisting of retinol dehydrogenase, retinal oxidase, retinal, dehydrogenase, β-carotene-15,15'-monooxygenase 1, and β-carotene oxygenase 2; a nucleic acid molecule that produces the RNA molecule; a vector comprising the nucleic acid molecule; a compound that inhibits the action of the enzyme; or a dominant negative mutant protein of the enzyme;

(5) the method according to (4), wherein the inhibitor is an RNA molecule that suppresses expression of a gene encoding retinol dehydrogenase, and the RNA molecule is selected from the group consisting of siRNA, shRNA, miRNA, stRNA and antisense RNA;

(6) the method according to (4), wherein the inhibitor is a compound that inhibits the action of retinol dehydrogenase;

(7) the method according to (2), wherein the inhibitor is a retinoic acid receptor antagonist, a dominant negative mutant protein of a retinoic acid receptor, an RNA molecule that suppresses expression of a gene encoding a retinoic acid receptor, a nucleic acid molecule that produces the RNA molecule, or a vector comprising the nucleic acid molecule;

(8) the method according to (1), wherein the modulator is an enhancer of the retinoic acid signaling system;

(9) the method according to (8), the enhancer is a retinoic acid receptor agonist;

(10) an adjuvant for prevention and/or therapy of cancer or infection, comprising a modulator of a retinoid metabolic pathway and/or a modulator of a retinoic acid signaling system (hereinafter, also referred to as "the prevention/therapy adjuvant for cancer/infection of the present invention");

(11) an adjuvant for immunotherapy of cancer, comprising a modulator of a retinoid metabolic pathway and/or a modulator of a retinoic acid signaling system (hereinafter, also referred to as "the cancer immunotherapy adjuvant of the present invention");

(12) an immunopotentiating agent comprising a modulator of a retinoid metabolic pathway and/or a modulator of a retinoic acid signaling system (hereinafter, also referred to as "the immunopotentiating agent of the present invention");

(13) a method of producing a T cell population, the method comprising a step of increasing the proportion of memory T cells in the T cell population by adding a modulator of a retinoid metabolic pathway and/or a modulator of a retinoic acid signaling system to the T cell population (hereinafter, also referred to as "the T cell population production method of the present invention");

(14) a T cell population produced by the method according to (13) (hereinafter, also referred to as "the T cell population of the present invention");

(15) a kit for prevention and/or therapy of cancer or infection, comprising:

(a) a cancer antigen, a pathogen of infection or an antigen of the pathogen, or an immune cell stimulated or activated by the antigen or the pathogen, and (b) a modulator of a retinoid metabolic pathway and/or a modulator of a retinoic acid signaling system (hereinafter, also referred to as "the kit for prevent ion/therapy of cancer/infection of the present invention");

(16) a modulator of a retinoid metabolic pathway and/or a modulator of a retinoic acid signaling system for increasing the proportion of memory T cells in a T cell population;

(17) a modulator of a retinoid metabolic pathway and/or a modulator of a retinoic acid signaling system for use in prevention and/or therapy of cancer or infection;

(18) the modulator according to (17) for use in immunotherapy of cancer;

(19) a combination for use in prevention and/or therapy of cancer or infection, comprising:

(a) a cancer antigen, a pathogen of infection or an antigen of the pathogen, or an immune cell stimulated or activated by the antigen or the pathogen, and (b) a modulator of a retinoid metabolic pathway and/or a modulator of a retinoic acid signaling system;

(20) a method of preventing and/or treating cancer or infection which comprises administering an effective amount of a cancer antigen, a pathogen of infection or an antigen of the pathogen, or an immune cell stimulated or activated by the antigen or the pathogen, and an effective amount of a modulator of a retinoid metabolic pathway and/or a modulator of a retinoic acid signaling system to a subject (hereinafter, also referred to as "the prophylactic/therapeutic method of cancer/infection of the present invention");

(21) a method of preventing and/or treating infection which comprises administering an effective amount of a modulator of a retinoid metabolic pathway and/or a modulator of a retinoic acid signaling system to a subject (hereinafter, also referred to as "the prophylactic/therapeutic method of infection of the present invention");

(22) a method of potentiating immunity of a subject which comprises administering an effective amount of a modulator of a retinoid metabolic pathway and/or a modulator of a retinoic acid signaling system to the subject (hereinafter, also referred to as "the immunopotentiating method of the present invention");

(23) use of a modulator of a retinoid metabolic pathway and/or a modulator of a retinoic acid signaling system in manufacture of a pharmaceutical composition for preventing and/or treating cancer or infection; and

(24) combined use of (a) a cancer antigen, a pathogen of infection or an antigen of the pathogen, or an immune cell stimulated or activated by the antigen or the pathogen, and (b) a modulator of a retinoid metabolic pathway and/or a modulator of a retinoic acid signaling system, in manufacture of a pharmaceutical composition for preventing and/or treating cancer or infection.

Effects of the Invention

As used herein, the modulator of a retinoid metabolic pathway and/or the modulator of a retinoic acid signaling system may enhance an immune response to an antigen in a subject via an increase in the proportion of memory T cells in a T cell population. Thus, the memory T cell proportion-increasing method of the present invention, the prevention/therapy adjuvant of cancer/infection of the present invention, the cancer immunotherapy adjuvant of the present invention, the immunopotentiating agent of the present invention, the T cell population production method of the present invention and the T cell population produced by the method, and the kit for prevention/therapy of cancer/infection of the present invention can be used for prevention/therapy of various diseases including cancer and infection. In addition, these can be used in combination with immunotherapy for various diseases including cancer and infection to increase the effect of the immunotherapy.

BRIEF DESCRIPTION OF DRAWINGS

FIG. 1 shows an outline of differentiation of T cells.

FIG. 2 shows effects of suppression of retinol dehydrogenase 10 expression by shRNA on the composition of a T cell population.

FIG. 3 shows effects of suppressed expression or high expression of retinol dehydrogenase 10 on proliferation and effector function of T cells. Graphs show a change rate (-fold) relative to a control (DMSO). The term "mock" means a control vector.

FIG. 4 shows effects of RDH10-high expression on retinoid metabolism. A horizontal axis shows fraction numbers of HPLC fractions.

FIG. 5 shows constructs used for preparation of RDH10-knockout mice.

FIG. 6 shows effects of RDH10 gene-knockout on retinoid metabolism. A horizontal axis shows fraction numbers of HPLC fractions. The term "f/f" means a control mouse, and the term "f/f cre" means a RDH10-conditional knockout mouse.

FIG. 7 shows increases of memory T cells in RDH10-knockout mice.

FIG. 8 shows increases of memory T cells in RDH10-knockout mice.

FIG. 9 shows expression of T cell surface molecules and their transcriptional factors in RDH10-knockout mice.

FIG. 10 shows cell numbers of lymphatic organs in RDH10-knockout mice.

FIG. 11 shows f cell numbers in RDH10-knockout mice.

FIG. 12 shows an outline of function analysis of RDH10-defective T cells and an evaluation test of memory T cell formation using *Listeria* infection models. The term "f/f cre" means a RDH10-conditional knockout mouse, and the term "f/f" means a control mouse.

FIG. 13 shows a rate of transferred T cells in *Listeria* infection models. The term "f/f cre" means T cells from a RDH10-conditional knockout mouse, and the term "f/f" means T cells from a control mouse.

FIG. 14 shows phenotypes of transferred T cells in *Listeria* infection models. The term "f/f cre" means T cells from a RDH10-conditional knockout mouse, and the term "f/f" means T cells from a control mouse. In graphs shown at the lower right, a curve under which the area is not filled shows T cells from a RDH10-knockout mouse, and a curve under, which the area is filled shows T cells from a control mouse.

FIG. 15 shows phenotypes of transferred T cells in *Listeria* infection models. The term "f/f cre" means T cells from a RDH10-conditional knockout mouse, and the term "f/f" means T cells from a control mouse.

FIG. 16 shows proliferation ability and *Listeria*-clearance ability of transferred T cells in *Listeria* infection models.

The term, "f/f cre" means a mouse into which T cells from a RDH10-conditional knockout mouse are transferred, and the term "f/f" means a mouse into which T cells from a control mouse are transferred.

FIG. 17 schematically shows effects of RDH10 gene-knockout as evaluated in *Listeria* infection models.

FIG. 18 shows effects of RDH10 defect in a vitamin A deficiency state. The term "f/f cre" means a RDH10-conditional knockout mouse, and the term "f/f" means a control mouse.

FIG. 19 shows enhanced differentiation of T cells by retinoic acid.

FIG. 20 shows effects of retinoic acid and an RAR antagonist on sensitivity of T cells to apoptosis.

FIG. 21 shows effects of retinoic acid and an RAR antagonist on division ability and proliferation ability of T cells.

FIG. 22 shows effects of retinoic acid and an RAR antagonist on the proportion of memory T cells.

FIG. 23 shows effects of retinoic acid and an RAR antagonist on reformation of a T cell population in mice.

FIG. 24 shows effects of retinoic acid and an RAR antagonist on the proportion and proliferation ability of $WT1_{332}$-specific memory T cells.

FIG. 25 shows an outline of an experiment for induction of memory T cells from effector T cells.

FIG. 26 shows effects of retinoic acid and an RAR antagonist on effector T cells.

FIG. 27 shows effects of retinoic acid and an RAR antagonist on the proportion of memory T cells in a T cell population reformed from effector T cells and the proliferation ability of T cells.

FIG. 28 shows an outline of an experiment for anti-tumor immunity induction using a human mi peptide and an RAR antagonist.

FIG. 29 shows results of an anti-tumor immunity induction experiment using a human WT1 peptide and an RAR antagonist.

FIG. 30 shows decreases in frequency of memory T cells by different RAR agonists. In the graph for CD62L expression amounts, a vertical axis shows mean fluorescence intensity (MFI).

FIG. 31 shows increases in frequency of memory T cells by different RAR antagonists. In the graph for CD62L expression amounts, a vertical axis shows mean fluorescence intensity (MFI).

FIG. 32 shows increases in cytotoxic activity of $CD4^+$ T cells by an RAR antagonist. An E/T ratio shows a ratio of the number of $CD4^+$ T cells to the number of target cells.

FIG. 33 shows results of western blotting analysis for detection of RDH10 protein contained in microsomal fractions of cells.

FIG. 34 shows measurement results of RDH10 enzymatic activity.

FIG. 35 shows effects of low-molecular inhibitors on RDH10 enzymatic activity.

FIG. 36 shows effects of RDH10 inhibitors on frequency of memory T cells in vitro.

FIG. 37 shows effects of RDH10 inhibitors on frequency of memory T cells in vitro.

FIG. 38 shows an outline of an experiment for administration of RDH10 inhibitors to recombinant *Listeria* infection mice.

FIG. 39 shows effects of RDH10 inhibitors on frequency of memory T cells in vivo.

FIG. 40 shows effects of RDH10 inhibitors on frequency of memory T cells in vivo.

FIG. 41 shows an outline of an experiment for anti-tumor immunity induction using RDH10 inhibitors.

FIG. 42 shows an outline of a tumor growth-suppression experiment using only RDH10 inhibitors.

FIG. 43 shows results of an anti-tumor immunity induction experiment using RDH10 inhibitors.

FIG. 44 shows results of a tumor growth-suppression experiment using only RDH10 inhibitors.

MODE FOR CARRYING OUT THE INVENTION

T cells differentiate from naive T cells in an undifferentiated state to T cell subsets having various functions. Among differentiated T cells, CD4 positive T cells (helper T cells) and CD8 positive T cells (killer T cells) play great roles in immune responses. Both the CD4 positive T cells and the CD8 positive T cells can be classified into memory T cells (central memory cells and effector memory cells) and effector cells (effector cells and terminal effector cells) depending on stages of differentiation. As used herein, positive and negative for CD antigen expression are expressed as symbol "+" and symbol "−" respectively. For example, a CD4 positive T cell is expressed as a $CD4^+$ T cell.

The T cell subsets can be determined by identifying surface antigens expressed on the cells, or cytokines, interferon, etc. produced by the cells. For example, $CD4^+$ T cells and CD8 T cells can toe classified into central memory cells ($CD127^+$, $CD62L^+$), effector memory cells ($CD127^+$, $CD62L^-$), effector cells ($CD127^-$, $CD62L^+$), or terminal effector cells ($CD127^-$, $CD62L^-$) based on the expression of surface antigens CD127 and CD62L. Stimulated T cells differentiate into central memory cells, effector memory cells, effector cells, and then terminal effector cells in this order (FIG. 1). Among these cells, the central memory cells have the highest proliferation ability and produce the most amount of IL-2. As the differentiation proceeds toward the terminal effector cell, production of IL-2 is decreased, production of IFN-γ is increased, and apoptosis tends to occur. The memory T cells are characterized in that apoptosis hardly occurs and they have strong proliferation ability. Thus, an increase of the proportion of memory T cells in a T cell population by the method of the present invention contributes to acquisition of strong immunity.

The modulator of a retinoid metabolic pathway and/or the modulator of a retinoic acid signaling system which is used in the memory T cell proportion-increasing method of the present invention may be an inhibitor of the retinoid metabolic pathway or an inhibitor of the retinoic acid signaling system, or an enhancer of the metabolic pathway or an enhancer of the signaling system. In a preferred aspect, the modulator is an inhibitor of the retinoid metabolic pathway or an inhibitor of the retinoic acid signaling system. In another preferred aspect, the modulator is an enhancer of the retinoic acid signaling system. Two or more kinds of these modulators may be used in combination.

The addition of the modulator of a retinoid metabolic pathway and/or the modulator of a retinoic acid signaling system to a T cell population may be performed in vitro or in vivo. An example of the in vitro addition is addition of the modulator to a medium in which the T cell population is cultured. An example of the in vivo addition is injection of the modulator into the body of a subject.

Inhibitor of Retinoid Metabolic Pathway

The memory T cell proportion-increasing method of the present invention may increase the proportion of memory T cells in a T cell population via suppression of differentiation from naive T cells or memory T cells to effector T cells and/or induction of memory T cells (in particular, central memory T cells) from effector (or terminal effector) T cells.

In one aspect, the memory T cell proportion-increasing method of the present invention increases the proportion of memory T cells, in particular central memory T cells, in a T cell population by inhibiting a retinoid metabolic pathway. As used herein, the inhibition of a retinoid metabolic pathway means inhibiting any reaction in a metabolic pathway in which retinoic acid is produced from vitamin A (retinoid) or provitamin A (retinoid precursor). In one aspect of the present invention, the inhibitor of the retinoid metabolic pathway inhibits one or more selected from a reaction converting retinol to retinal, a reaction converting retinal to retinoic acid, a reaction converting β-carotene to retinal, a reaction converting carotene to β-apocarotenal, and a reaction converting apocarotenal to retinal and retinoic acid.

In one aspect of the present invention, the inhibitor of the retinoid metabolic pathway inhibits the expression or action of an enzyme catalyzing any reaction in the retinoid metabolic pathway (hereinafter, referred to as a "retinoid metabolic enzyme"), for example, retinol dehydrogenase, retinal oxidase, retinal dehydrogenase, β-carotene-15,15'-monooxygenase 1 (BCMO1), or β-carotene oxygenase 2 (BCO2). In a preferred aspect, the inhibitor of the retinoid metabolic pathway is an inhibitor of retinol dehydrogenase, more preferably an inhibitor of retinol dehydrogenase 10 consisting of an amino acid sequence set forth by SEQ ID NO:1 (a DNA sequence encoding the enzyme is shown as SEQ ID NO:2) or a homolog thereof. As used herein, the homolog of retinol dehydrogenase 10 includes a protein consisting of an amino acid sequence having at least 80%, at least 85%, at least 90%, at least 95%, at least 98%, or at least 99% sequence identity with the amino acid sequence of SEQ ID NO:1, or a protein consisting of an amino acid sequence which differs tocom SEQ ID NO:1 by substitution, deletion, insertion and/or addition of one or several, for example 1, 2, 3, 4, 5, 6, 7, 8 or 9 amino acids.

In one aspect of the present invention, the inhibitor of the retinoid metabolic pathway is an RNA molecule that suppresses expression of a gene encoding the retinoid metabolic enzyme, a nucleic acid molecule that produces the RNA molecule, or a vector comprising the nucleic acid molecule.

The RNA molecule that suppresses expression of a gene encoding the retinoid metabolic enzyme usually targets mRNA encoding the retinoid metabolic enzyme, and suppresses production of the retinoid metabolic enzyme by inducing degradation of the mRNA, or inhibiting translation of the mRNA, or the like. Examples of the RNA molecule include siRNA, shRNA, miRNA, stRNA, and antisense RNA. Preferred examples of the RNA molecule include siRNA and shRNA. In one aspect, the retinoid metabolic enzyme whose gene expression is to be suppressed is retinol dehydrogenase, in particular retinol dehydrogenase 10. In a preferred aspect, the molecule that suppresses expression of a gene encoding retinol dehydrogenase targets mRNA transcribed from DNA consisting of a nucleotide sequence set forth by SEQ ID NO:2 or a nucleotide sequence having at least 80%, at least 85%, at least 90%, at least 95%, or at least 98% sequence identity with the nucleotide sequence of SEQ ID NO:2, and suppresses production of retinol dehydrogenase 10. In a preferred aspect, the RNA molecule is siRNA or shRNA, in particular shRNA, comprising a double-stranded part in which a sense strand of the double-stranded part consists of a nucleotide sequence set forth by SEQ ID NO:3 and an antisense strand of the double-stranded part consists of a nucleotide sequence set forth by SEQ ID NO:4.

The nucleic acid molecule that produces the RNA molecule means a nucleic acid molecule that directly or indirectly produces the RNA molecule. Examples of the nucleic acid molecule that produces the RNA molecule include a DNA construct and a recombinant retroviral RNA comprising a nucleotide sequence corresponding to the RNA molecule. As used herein, the term "directly" means, for example, to produce the desired RNA molecule by transcription from DNA or processing (splicing, editing, etc.) of precursor RNA, while the term "indirectly" means, for example, to produce DNA by reverse transcription from RNA and then produce the desired RNA molecule by transcription from the DNA.

The vector comprising the nucleic acid molecule may be an "expression vector" that leads to transient expression (production) of the desired RNA molecule, or a "transform vector" that leads to stable expression (production) of the desired RNA molecule by integration of a DNA sequence into a chromosome. The type of the vector used in the present invention is not limited as long as a vector that can be used in animal cells, for example human cells, and examples thereof include plasmid vectors, DNA viral vectors, and RNA viral vectors. For example, when a cell is infected with a retroviral vector including an RNA construct containing nucleotide sequences of the desired RNA molecule and a promoter, a DNA construct corresponding to the RNA construct is produced by reverse transcription, and the DNA construct is integrated into the cell's chromosome, and then, the desired RNA molecule is transcribed from the integrated DNA construct.

The compound that inhibits the action of the retinoid metabolic enzyme may be a low-molecular compound or a high-molecular compound. Examples of the high-molecular compound include antibodies binding to the retinoid metabolic enzyme and their antigen-binding fragments (Fab, $F(ab')_2$, etc.), and scFv. The low-molecular compound that inhibits the action of the retinoid metabolic enzyme can be obtained by known methods in the art, for example, by screening of a compound library for inhibitory action on the activity of the enzyme. The antibodies binding to the retinoid metabolic enzyme and their antigen-binding fragments, scFv, and the like can be also obtained by known methods in the art, for example, by immunization of animals using the enzyme as an antigen, or phage display.

In one aspect, the compound that inhibits the action of the retinoid metabolic enzyme is a compound that inhibits the action of retinol dehydrogenase, preferably a compound that inhibits the action of retinol dehydrogenase (SEQ ID NO: 1) (hereinafter, also referred to as an "RDH10 inhibitor"). In one aspect, the RDH10 inhibitor is a compound having a structure represented by the following formula (I):

[Chemical formula 1]

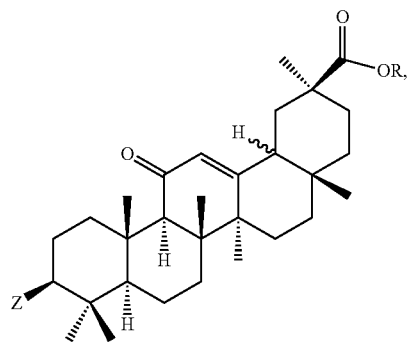

(I)

wherein R is H or CH$_3$,
Z is HO— or HOOC—Y—COO—, and
Y is —CH$_2$CH$_2$—, —CH=CH—, or a phenylene group;
or a salt thereof.

In a preferred aspect, in formula (I), Z is HOOC—Y—COO—. More preferably, Y is —CH=CH— or a phenylene group.

Examples of a salt of the compound represented by formula (I) include a sodium salt and a potassium salt, preferably a sodium salt.

The RDH10 inhibitor is preferably one or more compounds selected from the group consisting of RDHI-001, RDHI-002, RDHI-003, RDHI-004, RDHI-005, RDHI-006, RDHI-007, RDHI-008, RDHI-009, RDHI-0010, and RDHI-0011.

The RDH10 inhibitor is more preferably one or more compounds selected from the group consisting of RDHI-001, RDHI-002, RDHI-003, and RDHI-004.

The RDH10 inhibitor is further preferably one or more compounds selected from the group consisting of RDHI-001, RDHI-002, and RDHI-003.

The compounds from RDHI-001 to RDHI-011 are represented by the following formulae.

[Chemical formula 2]

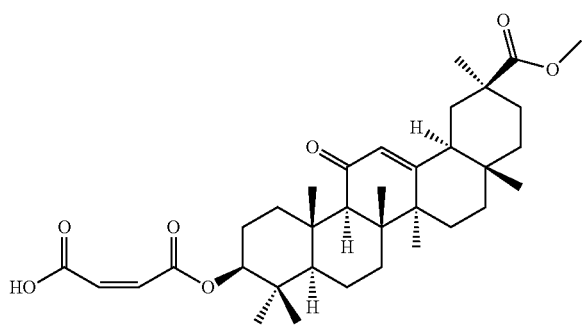

RDHI-001

[Chemical formula 3]

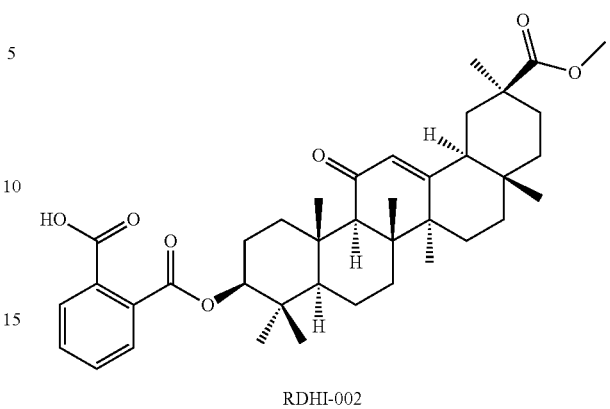

RDHI-002

[Chemical formula 4]

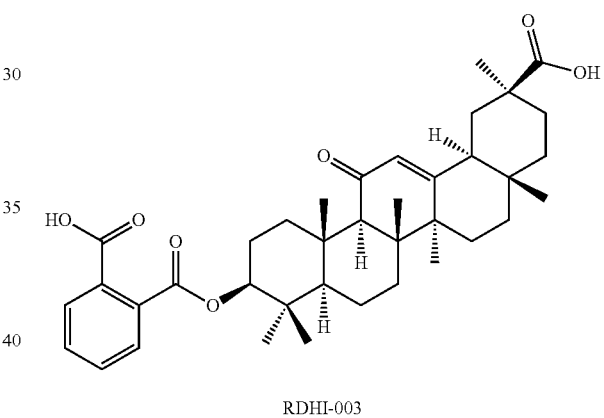

RDHI-003

[Chemical formula 5]

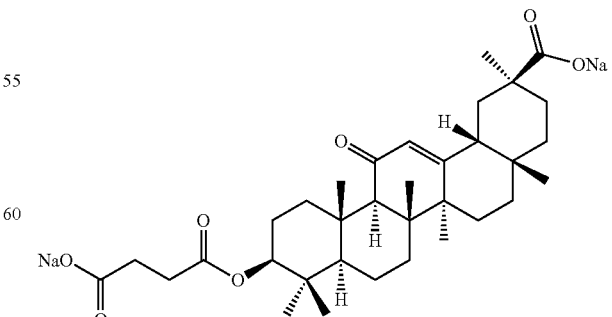

RDHI-004

-continued

[Chemical formula 6]

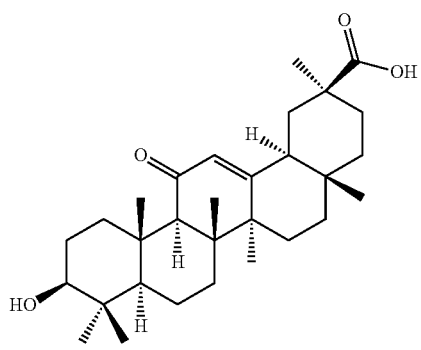

RDHI-005

[Chemical formula 7]

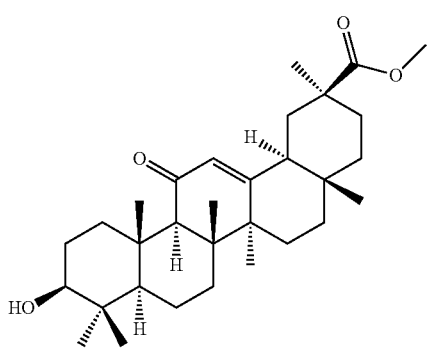

RDHI-006

[Chemical formula 8]

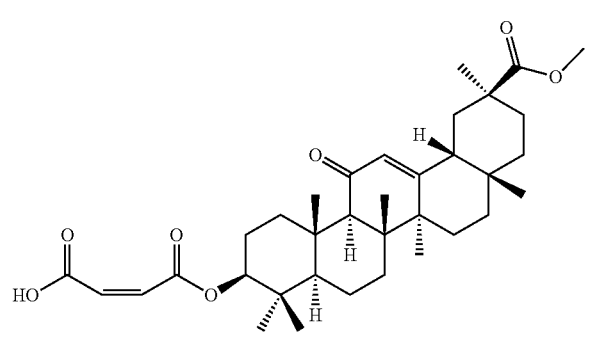

RDHI-007

[Chemical formula 9]

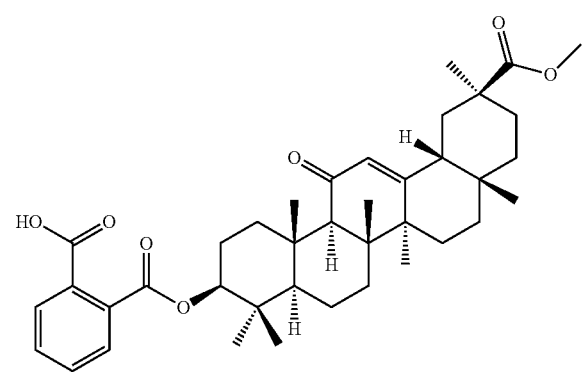

RDHI-008

-continued

[Chemical formula 10]

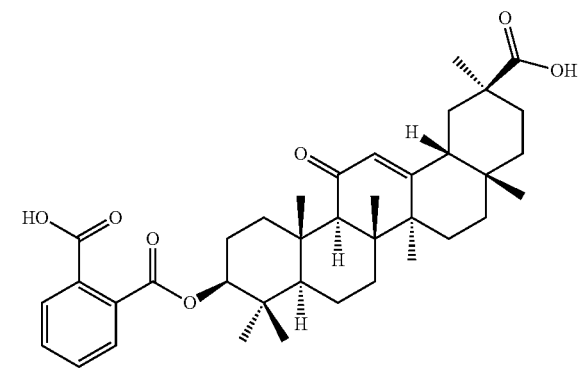

RDHI-009

[Chemical formula 11]

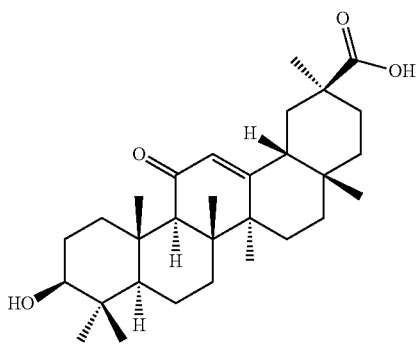

RDHI-010

[Chemical formula 12]

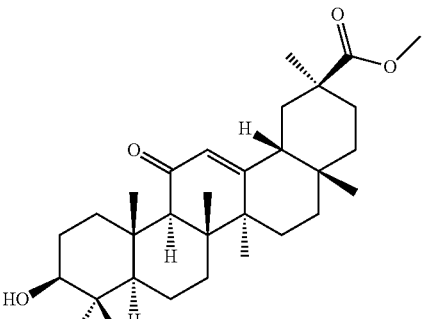

RDHI-011

In the present invention, a dominant negative mutant protein of the retinoid metabolic enzyme can be also used as the inhibitor of the retinoid metabolic pathway. The dominant negative mutant protein can be obtained, for example, by preparing mutant proteins of the retinoid metabolic enzyme and selecting the mutant protein that has binding ability to a substrate and does not have the original catalytic action. In addition, the preparation and selection steps of the desired mutant protein can be made more efficient by analysis of a functional site of the enzyme.

The enhancer or inhibitor of the retinoid metabolic pathway can be also obtained by means of so-called SBDD (Structure-Based Drug Design). For example, a retinoid metabolic enzyme such as retinol dehydrogenase 10 is purified, crystallized, and then subjected to X-ray analysis to determine its steric structure, a compound that binds to the retinoid metabolic enzyme is designed based on the steric structure, the compound is tested for activity to identify a compound that functions as the enhancer or inhibitor of the retinoid metabolic pathway.

Retinoic Acid Signaling System and Inhibitor Thereof

The retinoic acid signaling system means a transduction system of a signal (for example, transcriptional modulation of a gene having a retinoic acid-responsive element) produced by binding of retinoic acid (hereinafter, also referred to as "RA") to a retinoic acid receptor (hereinafter, also referred to as "RAR") in the nuclei of cells. In one aspect, the memory T cell proportion-increasing method of the present invention increases the proportion of memory T cells, in particular central memory T cells, in a T cell population by inhibiting the signaling system. In a preferred aspect, the memory T cell proportion-increasing method of the present invention increases the proportion of CD4 positive memory T cells in a T cell population by inhibiting the retinoic acid signaling system.

Examples of the inhibitor of the retinoic acid signaling system include a retinoic acid receptor antagonist, a dominant negative mutant protein of a retinoic acid receptor, an RNA molecule that suppresses expression of a gene encoding a retinoic acid receptor, a nucleic acid molecule that produces the RNA molecule, and a vector comprising the nucleic acid molecule. In a preferred aspect, the inhibitor is a retinoic acid receptor antagonist.

Examples of the retinoic acid receptor antagonist include compounds such as LE540, LE135, LE550, BMS195614, MM11253, AGN194310, Ro41-5253, AGN193109, CD2665, and BMS493, and their analogs or derivatives, and antibodies blocking the binding between retinoic acid and a retinoic acid receptor. In a preferred aspect, the retinoic acid receptor antagonist is one or more compounds selected from the group consisting of LE540, LE135, BMS195614 and MM11253, and their analogs and derivatives. LE540, LE135, LE550, BMS195614, MM11253, AGN194310, Ro41-5253, AGN193109, CD2665, and BMS493 are represented by the following formulae.

[Chemical formula 13]

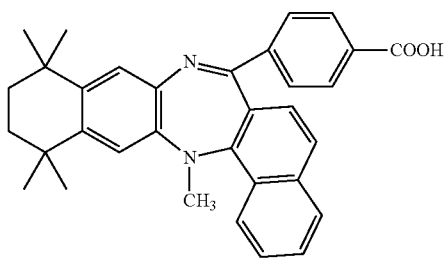

LE540

[Chemical formula 14]

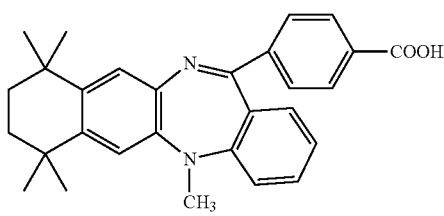

LE135

[Chemical formula 15]

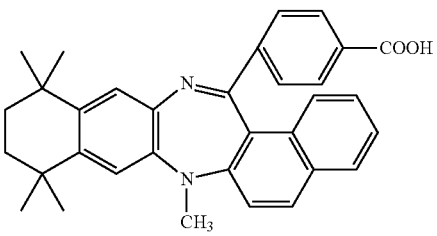

LE550

[Chemical formula 16]

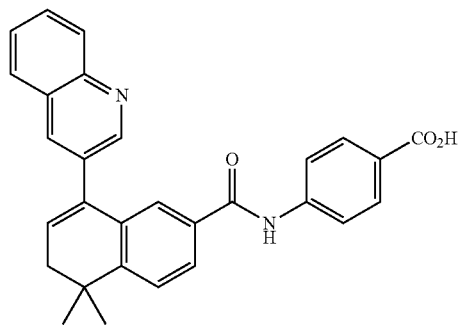

BMS195614

[Chemical formula 17]

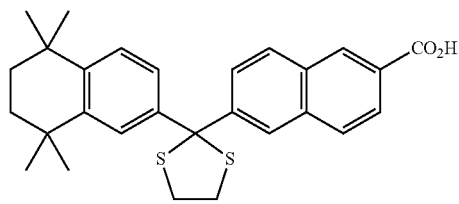

MM11253

[Chemical formula 18]

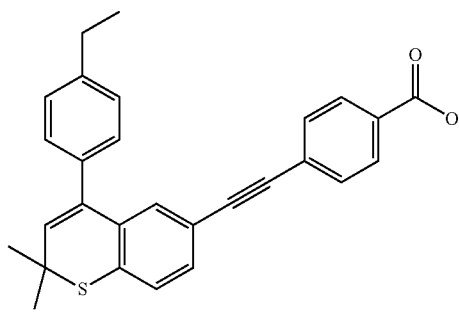

AGN194310

[Chemical formula 19]

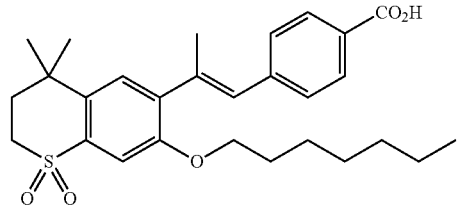

Ro41-5253

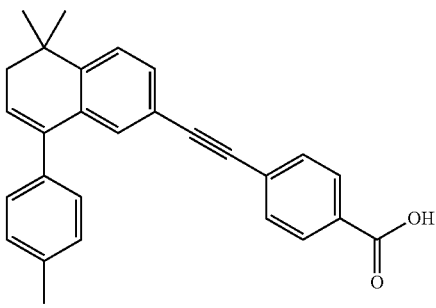

AGN193109

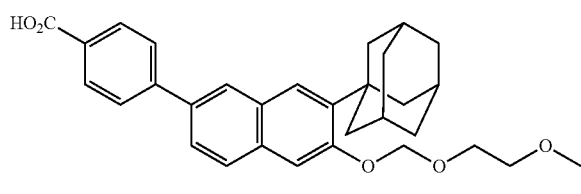

CD2665

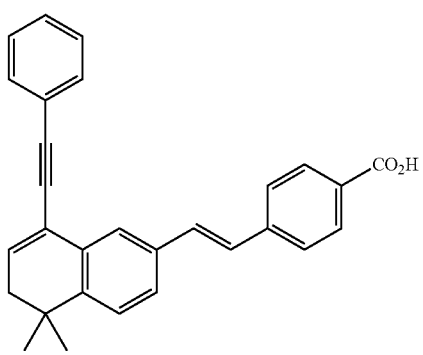

BMS493

Compounds that act as the retinoic acid receptor antagonist other than the above-mentioned compounds can be obtained by known methods in the art, for example, by screening of a library of compounds having similar structures to retinoic acid, LE540 and the like.

In the present invention, a dominant negative mutant protein of the retinoic acid receptor can be also used as the inhibitor of the retinoic acid signaling system. The dominant negative mutant protein can be obtained, for example, by preparing mutant proteins of the retinoic acid receptor and selecting the mutant protein that has binding ability to retinoic acid and does not produce a signal. In addition, the preparation and selection steps of the desired mutant protein can be made more efficient by analysis of a functional site of the receptor.

In another aspect of the present invention, an RNA molecule that suppresses expression of a gene encoding the retinoic acid receptor (RAR gene) can be also used as the inhibitor of the retinoic acid signaling system. The RNA molecule that suppresses expression of the RAR gene usually targets mRNA encoding RAR, and suppresses production of RAR by inducing degradation of the mRNA, or inhibiting translation of the mRNA, or the like. Examples of the RNA molecule include siRNA, shRNA, miRNA, stRNA, and antisense RNA. Preferred examples of the RNA molecule include siRNA and shRNA.

For example, in human, three subtypes of RARα, RARβ and RARγ are known as the retinoic acid receptor, and they are reported to have plural isoforms (variants). For example, RARα is known to have isoforms consisting of amino acid sequences of NP_000955, NP_001019980 and NP_001138774 (shown as accession numbers of National Center for Biotechnology Information (NCBI)), RARβ is known to have isoforms consisting of amino acid sequences of NP_000956 and NP_057236 (shown as accession numbers of NCBI), and RARγ is known to have isoforms consisting of amino acid sequences of NP_00957, NP_001036193, NP_001230661, NP_001230659 and NP_001230660 (shown as accession numbers of NCBI). As used herein, DNA sequences encoding these isoforms are set forth by SEQ ID NO:5-14. Thus, in a preferred aspect, the RNA molecule that suppresses expression of the RAR gene targets mRNA transcribed form DNA consisting of any nucleotide sequence of SEQ ID NOs:5-14 or a nucleotide sequence having at least 80%, at least 85%, at least 90%, at least 95%, or at least 98% sequence identity with any nucleotide sequence of SEQ ID NOs:5-14, and suppresses production of one or more of RARα, RARβ and RARγ.

The definition and examples of the "nucleic acid molecule" that (directly or indirectly) produces the RNA molecule that suppresses expression of the RAR gene, and the "vector" comprising the nucleic acid molecule are the same as described above for the nucleic acid molecule that produces the "RNA molecule that suppresses expression of a gene encoding the retinoid metabolic enzyme" and the vector comprising the nucleic acid molecule.

Enhancer of Retinoic Acid Signaling System

In one aspect, the memory T cell proportion-increasing method of the present invention increases the proportion of memory T cells in a T cell population by enhancing the retinoic acid signaling system. For example, naive T cells are treated with an enhancer of the retinoic acid signaling system to allow the T cells to differentiate efficiently, and thereby memory T cells can be increased. Thus, in one aspect, the memory T cell proportion-increasing method of the present invention increases the proportion of memory T cells in at T cell population by adding an enhancer of the retinoic acid signaling system to the T cell population comprising naive T cells. In such an aspect, the proportion of naive T cells in the T cell population to which the enhancer of the retinoic acid signaling system is added is preferably at least 20%, for example at least 30%, at least 40%, at least 50%, at least 60%, at least 70%, at least 80%, at least 90%, or at least 95%. The T cell population to which the enhancer of the retinoic acid signaling system is added may or may not consist of only naive T cells.

Examples of the enhancer of the retinoic acid signaling system include a retinoic acid receptor agonist, and a nucleic acid molecule having a nucleotide sequence encoding a retinoic acid receptor, preferably a retinoic acid receptor agonist. In a preferred aspect, the retinoic acid receptor agonist is retinoic acid, in particular all-trans retinoic acid (ATRA). In another preferred aspect, the retinoic acid receptor agonist is one or more compounds selected from the group consisting of all-trans retinoic acid (ATRA), LE511, AM580, AC55649, and CD437, and their analogs and derivatives. All-trans retinoic acid (ATRA), LE511, AM580, AC55649, and CD437 are represented by the following formulae.

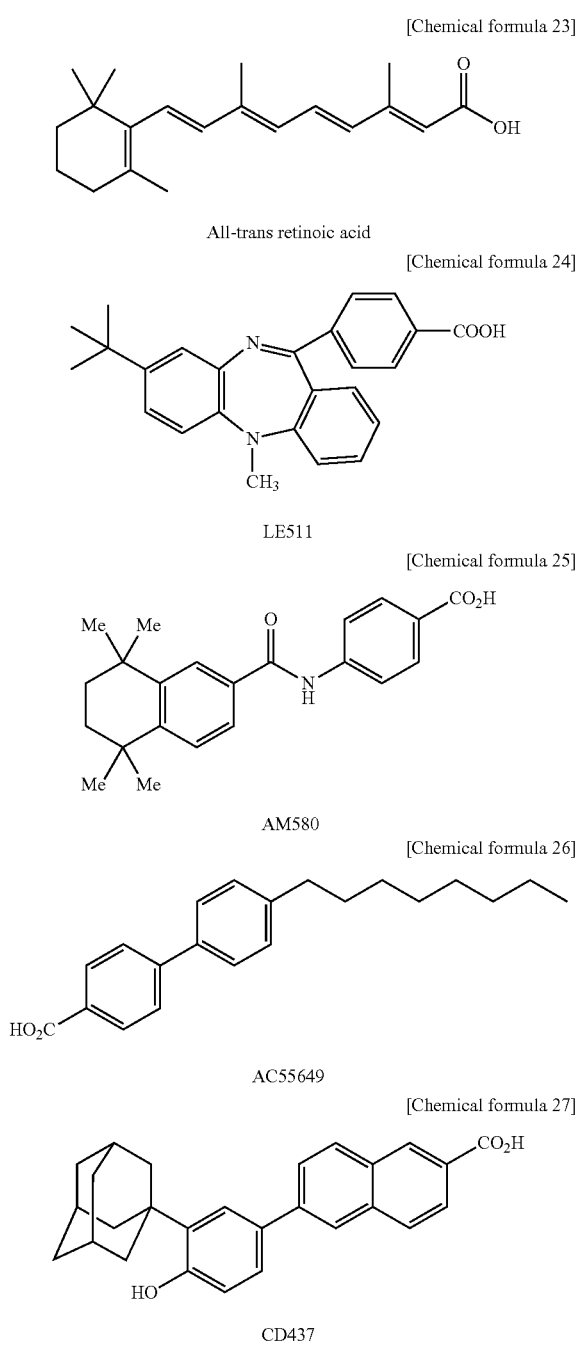

[Chemical formula 23] All-trans retinoic acid
[Chemical formula 24] LE511
[Chemical formula 25] AM580
[Chemical formula 26] AC55649
[Chemical formula 27] CD437

The nucleic acid molecule having a nucleotide sequence encoding a retinoic acid receptor can foe introduced into T cells by known methods in the art such as an expression vector, for example, to enhance the retinoic acid signaling system by overexpression of the retinoic acid receptor, Prevention/Therapy Adjuvant for Cancer/Infection The prevention/therapy adjuvant for cancer/infection of the present invention contains a modulator of a retinoid metabolic pathway and/or a modulator of a retinoic acid signaling system as an effective ingredient. The modulation (inhibition or enhancement) of the metabolic pathway or the signaling system results in an increase of the proportion of memory T cells in a T cell population. In a preferred aspect, the prevention/therapy adjuvant for cancer/infection of the present invention increases the therapeutic effect against cancer of immunotherapy, in particular immunotherapy using a cancer-antigen peptide. Examples of the cancer-antigen peptide used in cancer immunotherapy include, but limited to, various WT1 peptides, for example, human $WT1_{332}$ (SEQ ID NO:15, as described in WO2042/046730), $MAGE-A4_{278-299}$ (SEQ ID NO:16), $Survivin_{97-111}$ (SEQ ID NO:17), and variant peptides having equivalent activity to that of the above-mentioned WT1 peptides.

The modulation (inhibition or enhancement) of the retinoid metabolic pathway or the retinoic acid signaling system results in not only an increase of the proportion of memory T cells but also an increase of the number of T cells. Thus the modulator or the retinoid metabolic pathway or the retinoic acid signaling system is also effective as an adjuvant for prevention (for example, vaccine) and therapy (for example, immunotherapy) of infection.

The inhibitor of the retinoic acid signaling system (for example, RAR antagonists) may enhance the cytotoxic activity of $CD4^+$ T cells. Thus the inhibitor of the retinoic acid signaling system is effective as an adjuvant for therapy of cancer or infection, in particular immunotherapy of cancer or infection.

Examples of cancer to be treated with the prevention/ therapy adjuvant for cancer/infection of the present invention include, but not limited to, carcinomas, sarcomas, and hematopoietic organ tumors. In a preferred aspect, examples of cancer to be treated with the adjuvant include various cancers and tumors expressing a WT1 gene, for example, hematopoietic organ tumors such as leukemia, myelodysplastic syndrome, multiple myeloma, and malignant lymphoma, and solid cancers and solid tumors such as stomach cancer, bowel cancer, lung cancer, breast cancer, germ-cell cancer, liver cancer, skin cancer, bladder cancer, prostate cancer, uterus cancer, uterine cervical cancer, ovary cancer, and brain tumor.

Infections to be treated with the prevention/therapy adjuvant for cancer/infection of the present invention, are not particularly limited. This is because strong immunity is obtained, regardless of the type of infection, via an increase in the number of T cells and an increase in the proportion of memory T cells by the modulator of the retinoid metabolic pathway or the retinoic acid signaling system. In one aspect, examples of infection to be treated with the adjuvant may include infections caused by bacteria, viruses, and protozoan organisms.

Immunopotentiating Agent

As above described, the modulator of the retinoid metabolic pathway or the retinoic acid signaling system increases the proportion of memory T cells and the number of T cells. Thus the modulator can be used as an effective ingredient of an immunopotentiating agent that non-specifically increases the immunity of a subject.

The prevention/therapy adjuvant for cancer/infection, the cancer immunotherapy adjuvant, and the immunopotentiating agent of the present invention may contain, for example, a carrier, an excipient, and the like, other than the modulator of the retinoid metabolic pathway and/or the modulator of the retinoic acid signaling system as the effective ingredient. A method of administration of the prevention/therapy adjuvant for cancer/infection, the cancer immunotherapy adjuvant, and the immunopotentiating agent of the present invention can be appropriately selected according to conditions such as the type of disease, the condition of a subject, the target site and the like. Examples of the administration method include, but not limited to, intradermal administration, subcutaneous administration, intramuscular administration, intravenous administration, transnasal administration, and oral administration. The amount of the above-mentioned effective ingredient contained in the prevention/therapy adjuvant for cancer/infection, the cancer immunotherapy adjuvant, and the immune-potentiating agent of the present invention, the dosage form and the frequency of administration of the adjuvant and immunopotentiating agent, and the like can be appropriately selected according to conditions such as the type of disease, the condition of a subject, the target site and the like.

Production Method of T Cell Population

The T cell population production method of the present invention comprises adding a modulator of a retinoid metabolic pathway and/or a modulator of a retinoic acid signaling system to a T cell population, and thereby a T cell population containing an increased proportion of memory T cells is obtained as compared with conventionally used T cell culture methods. In the method, the addition of a modulator of a retinoid metabolic pathway and/or a modulator of a retinoic acid signaling system to a T cell population may be performed in vitro or in vivo, preferably in vitro. An example of the in vitro addition is addition of the modulator to a medium in which the T cell population is cultured. An example of the in vivo addition is administration of the modulator into the body of a subject.

The T cell population produced by the T cell population production method of the present invention can be used for increasing the preventive and/or therapeutic effect in prevention and/or therapy of various diseases, preferably cancer or infection, in particular immunotherapy of carter or infection.

Therapeutic Method and Kit

The prophylactic/therapeutic method of cancer/infection of the present invention, and the kit for prevention/therapy of cancer/infection of the present invention comprises use of a modulator of a retinoid metabolic pathway and/or a modulator of a retinoic acid signaling system, in combination with other effective ingredients for prevention and/or therapy of cancer or infection, in particular immunotherapy of cancer or infection. Examples of the other effective ingredients include a cancer antigen, a pathogen of infection or an antigen of the pathogen, and an immune cell stimulated or activated by the antigen or the pathogen.

The cancer antigen means a surface antigen specifically expressed on a cancer cell or a tumor cell (so-called tumor-specific antigen) and a partial peptide of the antigen. Examples of the cancer antigen include WT1 protein which is a product of cancer gene and a WT1 peptide which is a partial peptide of the protein, such as $WT1_{332}$ or the like. Examples of the pathogen of infection include bacteria, fungi, viruses, and protozoan organisms. Examples of the antigen of the pathogen include proteins, glycoproteins, and sugar chains expressed on the surface of bacteria, fungi, viruses and the like, and cell walls of bacteria and fungi, and the cell wall components (lipopolysaccharide etc.). Examples of the immune cell stimulated or activated by the antigen or the pathogen include antigen-presenting cells (for example, dendritic cells, macrophages, and B cells), and T cells activated by the antigen-presenting cells.

The prevention/therapy adjuvant for cancer/infection, the cancer immunotherapy adjuvant, and the immunopotentiating agent of the present invention may be used in combination with an effective ingredient for prevention and/or therapy of various diseases, preferably cancer or infection, in particular immunotherapy of cancer or infection. Examples of the effective ingredient include the cancer antigen, the pathogen of infection or the antigen of the pathogen, and the immune cell stimulated or activated by the antigen or the pathogen as described above.

A subject to be treated with the memory T cell, proportion-increasing method, the prevention/therapy adjuvant for cancer/infection, the cancer immunotherapy adjuvant, the immunopotentiating agent, the kit for prevention/therapy of cancer/infection, the prophylactic/therapeutic method of cancer/infection, the prophylactic/therapeutic method of infection, and the immunopotentiating method of the present invention is not particularly limited as long as it is an animal having an immunity system, in particular an acquired immunity system, that is a vertebrate animal. Examples of the subject include human, mouse, rat, dog, cat, rabbit, horse, bovine, sheep, pig, goat, monkey, and chimpanzee. In a preferred aspect, the subject is a human.

In the prophylactic/therapeutic method of cancer/infection, the prophylactic/therapeutic method of infection, and the immunopotentiating method of the present invention, the effective amount of the modulator of a retinoid metabolic pathway and/or the modulator of a retinoic acid signaling system which is administered to the subject, and the effective amount of the cancer antigen, the pathogen of infection or the antigen of the pathogen, or the immune cell stimulated or activated by the antigen or the pathogen can be appropriately determined according to conditions such as the type of disease, the condition of the subject, the target site and the like, or by using methods well-known to a person skilled in the art (including various non-clinical and/or clinical trials). Examples of the cancer antigen, the pathogen of infection or the antigen of the pathogen, and the immune cell stimulated or activated by the antigen or the pathogen which may be used in the prophylactic/therapeutic method of cancer/infection, the prophylactic/therapeutic method of infection, and the immunopotentiating method of the present invention are as described above.

The inhibitors of the retinoid metabolic pathway, the inhibitors of the retinoic acid signaling system, and the enhancers of the retinoic acid signaling system as described for "the memory T cell proportion-increasing method" can be also used for the prevention/therapy adjuvant for cancer/infection, the cancer immunotherapy adjuvant, and the immunopotentiating agent, the T cell population production method, the kit for prevention/therapy of cancer/infection, the prophylactic/therapeutic method of cancer/infection, the prophylactic/therapeutic method of infection, and the immunopotentiating method of the present invention of the present invention.

Hereinafter, the present invention is explained specifically and in detail by way of Examples to which the present invention should not be limited.

EXAMPLES

Example 1

Suppression of Expression of Retinol Dehydrogenase 10 by shRNA

A construct to express an shRNA targeting retinol dehydrogenase 10 and consisting of a sequence set forth in SEQ ID NO:18 (RDH10-targeting shRNA) was introduced into human $CD4^+CD45RO^+$ T cells. Specifically, using a lentivirus vector system, packaging cells (293T cell line) were co-transfected with a vector in which a DNA consisting of a nucleotide sequence of SEQ ID NO:19 was incorporated into a cloning site and a packaging vector to produce a recombinant virus, and the human $CD4^+CD45RO^+$ T cells were infected with the recombinant virus. Integration of the shRNA expression construct into a chromosome was confirmed based on the expression of GFP as a reporter which was located downstream of the shRNA expression construct. In the T cell population in which the RDH10-targeting shRNA was expressed by such a method, the proportion of terminal effector cells (CD127$^+$, CD62L$^+$) was decreased and the proportion of central memory cells (CD127$^+$, CD62L$^+$) was increased, as compared with a T cell population in which a control shRNA (SEQ ID NO:20) was expressed by the same method (FIG. 2).

The RDH10-targeting shRNA (sh #10-2, SEQ ID NO:18), or an shRNA targeting luciferase (sh-luc, SEQ ID NO:20) as a control was introduced into human CD4$^+$CD45RO$^+$ T cells using a lentivirus vector. In the same way, a lentivirus vector in which an RDH10 gene was incorporated was introduced into human CD4$^+$CD45RO$^+$ T cells to produce RDH10 high-expression T cells.

These cells were cultured in the presence of an anti-CD3 antibody, an anti-CD28 antibody and IL-2 together with various concentrations of retinol (all-trans type) for a week. Then, the number of cells was measured and at the same time, the frequency of cells producing IFN-γ was determined by an intracellular cytokine assay. Results are shown in FIG. 3.

The presence of retinol increased the number of cells and the IFN-γ producing cells in a retinol concentration-dependent manner. On the other hand, the suppression of RDH10 expression suppressed their increase rates and the overexpression of RDH10 enhanced their increase rates.

In a 10 cm culture dish, 5×10$^7$ cells of the RDH10 high-expression T cell (indicated as #10 in FIG. 4) or the control vector-introduced T cell (indicated as mock in FIG. 4) were put together with a culture medium, and 1 μM $^3$H-labelled all-trans retinol was added. After culturing at 37° C. for 4 hours, the cells were collected, and retinoid within the cells was extracted using hexane. The hexane used for the extraction was removed by dry centrifugation. Then, the concentrated retinoid was dissolved in acetonitrile, and fractionalized by HPLC, and $^3$H contained in each fraction was measured by a liquid scintillation counter. Standard samples (all-trans retinol and all-trans retinal) were previously separated by HPLC, and fractions containing each standard sample were determined. A solution of acetonitrile: 50 mM ammonium acetate=75:25 was used as a solvent for HPLC, and Syhergi 4u Hydro-RP 80A (manufactured by Phenomenex Inc.) was used as a separation column. HPLC was performed at a flow rate of 1.5 ml/minute, and fractions were collected every one minute. Results are shown in FIG. 4.

In the RDH10 high-expression T cell, the conversion from all-trans retinol to all-trans retinal was promoted.

Example 2

T Cell Population in Retinol Dehydrogenase 10-Knockout Mouse (1) Production or Conditional Knockout Mouse A mouse in which a gene of retinol dehydrogenase 10 (hereinafter, also referred to as RDH10) on a chromosome was replaced by construct A shown in FIG. 5 was produced using a targeting vector. The mouse was crossed with a transgenic mouse expressing Flp recombinase to produce a mouse having a gene structure in which a LacZ gene and a neo gene were removed (as shown in FIG. 5-B: hereinafter, the structure is referred to as "flox allele"). The mouse having the flox allele thus obtained and a transgenic mouse expressing Cre recombinase were crossed to obtain a knockout mouse having a gene structure in which the exon 2 of RDH10 was removed (as shown in FIG. 5-C).

(2) Retinoid Metabolism in Knockout Mouse

From spleen cells of the RDH10 conditional knockout mouse (flox/flox cre) produced as described above and a control mouse (flox/flox), CD4$^+$ T cells were separated using a cell sorter. The separated CD4$^+$ T cells were activated and proliferated by using an anti-CD3 antibody, an anti-CD28 antibody and IL-2. Then, 3×10$^7$ cells of the CD4$^+$ T cell from each mouse were put in a 10 cm culture dish together with a culture medium, and 1 μM $^3$H-labelled all-trans retinol was added. After nurturing at 37° C. for 4 hours, the cells were collected, and retinoid within the cells was extracted using hexane. The hexane used for the extraction was removed by dry centrifugation. Then, the concentrated retinoid was dissolved in acetonitrile, and fractionalized by HPLC, and $^3$H contained in each fraction was measured by a liquid scintillation counter. Standard samples (all-trans retinol and all-trans retinal) were previously separated by HPLC, and fractions containing each standard sample were determined. A solution of acetonitrile: 50 mM ammonium acetate=75:25 was used as a solvent for HPLC, and Syhergi 4u Hydro-RP 80A (manufactured by Phenomenex Inc.) was used as a separation column. HPLC was performed at a flow rate of 1.5 ml/minute, and fractions were collected every one minute. Results are shown in FIG. 6.

In the RDH10 knockout mouse, the conversion from all-trans retinol to all-trans retinal was suppressed as compared with the control mouse.

(3) Identification of T Cell Subset in Knockout Mouse

A knockout mouse having a genotype of wild-type homo (wt/wt), flox allele/wild-type hetero (flox/wt), or flox allele homo (flox/flox) with respect to a locus of RDH10 gene was crossed with a transgenic mouse expressing Cre recombinase to obtain a mouse (hereinafter, also referred to as the test mouse). In the test mouse, a T cell subset was identified based on the expression of CD44 and CD62L. As a result, in the RDH10 flox/flox mouse and the RDH10 flox/wt mouse, the proportion of memory-type T cells highly expressing CD62L in both a CD4$^+$ T cell population and a CD8$^+$ T cell population was increased, as compared with the RDH10 wt/wt mouse (FIG. 7).

(4) Increase of Memory T Cells in Knockout Mouse

The expression of CD62L and CD127 on CD4$^+$ T cells and CD8$^+$ T cells present in the peripheral lymph nodes of a 6 to 8 week-old RDH10 conditional knockout mouse (f/f cre) and a control mouse (f/f) was analyzed by flow cytometry. Results are shown in FIG. 8. In the RDH10 conditional knockout mouse, CD62L and CD127 were highly expressed, and thereby it was found that the proportion of memory-type T cells was increased.

(5) Expression of T Cell Surface Molecule and its Transcriptional Factor

In the test mouse, the expression of a T cell surface molecule and its transcriptional factor was examined. In the RDH10 flox/flox mouse, cell surface molecules (CD62L (Sell), S1p1 (Edg1) Ccr7, IL7ra) that were characteristic of memory-type T cells and transcriptional factors (Klf2, Foxo1, Foxo3, Ets1, Sp1, Irf1) relating to the expression of the cell surface molecules were highly expressed, as compared with the RDH10 wt/wt mouse and the RDH10 flox/wt mouse (FIG. 9).

(6) Number of Cells in Lymphoid Organ and Number of T Cells in the Lymphoid Organ In the test mouse, the number of cells in lymphoid organs and the number of T cells in the lymphoid organs were examined. In the RDH10 flox/flox mouse and the RDH10 flox/wt mouse, the numbers of cells in a primary lymphoid organ (thymus gland) and a secondary lymphoid organ (lymph node and spleen) were increased as compared with the RDH10 wt/wt mouse, suggesting that proliferation of lymphocytes was promoted (FIG. 10). Further, in the RDH10 flox/flox mouse and the RDH10 flox/wt mouse, both the number of $CD4^+$ T cells and the number of $CD8^+$ T cells were increased in the lymph node and spleen as compared with the RDH10 wt/wt mouse (FIG. 11).

(7) Function Analysis of RDH10-Defective T Cells and Evaluation of Memory T Cell Formation Using *Listeria* Infection Model

[Method]

From a mouse in which an OT-I TCR gene was introduced (transgenic) and a Rag1 gene was knocked out, an RDH10 conditional knockout mouse (flox/flox cre) and a control mouse (flox/flox) were produced. To distinguish T cells from the RDH10 conditional knockout mouse and T cells from the control mouse, the RDH10 conditional knockout moose was designed to have two marker molecules CD45.1 and CD45.2. On the other hand, the control mouse had only CD45.1. T cells ($CD8^+$ T cells expressing only OT-I TCR) were obtained from these mice. The T cells from both mice were mixed in an amount of each $1 \times 10^4$ cells at a ratio of 1:1, and then the mixture was administered to a wild-type mouse having only CD45.2 (C57BL/6J) via a tail vein.

On the next day, the mouse was infected with $1 \times 10^4$ CPU of recombinant *Listeria monocytogenes* expressing an OVA peptide recognized by OT-I TCR (LM-OVA). The spleen and lymph node were removed from the mouse and changes in the proportion of and the phenotypes of the T cells transferred into the spleen and lymph node were analyzed over time.

Further, to evaluate the function of memory T cells, the transferred RDH10 conditional knockout mouse-derived. T cells (CD45.1+CD45.2+) and the transferred control mouse-derived T cells (CD45.1+CD45.2−) were isolated from the spleen and lymph node obtained from the mouse 30 days or more after the Infection which was at the memory phase by using an FACS sorter, and the RDH10 conditional knockout mouse-derived T cells and the control mouse-derived T cells were transferred into separate wild-type mice in an amount of each $1 \times 10^4$ cells. On the next day, the mice were infected with $1 \times 10^6$ CFU of LM-OVA (secondary infection). After 5 days, the bacterial, number of *Listeria* present in the spleen and liver of the mice and the number of T cells transferred into the spleen and liver were analyzed.

An outline of the above-described experiment is shown in FIG. 12.

[Results]

Changes in the proportions and the phenotypes of the transferred T cells after the LM-OVA infection are shown in FIGS. 13 to 15. In both the spleen and the lymph node, the proportion of the RDH10 conditional knockout mouse-derived T cells was higher than that in the control mouse-derived T cells (FIG. 13). Further, in the RDH10 conditional knockout mouse-derived T cells, the proportion of memory T cells ($CD62L^+CD127^+$ cells) and the proportion of memory precursor effector cells (MPEC) ($KLRG1^-CD127^+$ cells) were higher than those in the control mouse-derived T cells (FIGS. 14 and 15).

After the secondary infection, the RDH10 conditional knockout mouse-derived T cells had strong proliferation ability and strong *Listeria*-clearance ability as compared with the control mouse-derived cells (FIG. 16).

From the above-described results, it was found that the RDH10 knockout mouse-derived T cells produce more memory T cells and have qualitatively high memory function (FIG. 17).

(8) Effect of RDH10 Defect in Vitamin A Deficiency State

To determine whether the increased expression of CD62L on RDH10-defective T cells was caused by a defect in metabolism of vitamin A (retinol) by RDH10, the RDH10 conditional knockout mouse (flox/flox cre) and the control mouse (flox/flox) were fed with vitamin A-deficient diet for 4 weeks. Then, the expression of CD62L and CD127 on T cells in lymph nodes (axillar and inguinal), a mesenteric lymph node, and a spleen was analyzed by flow cytometry. Results are shown in FIG. 18. In the vitamin A deficiency state, as increase in the expression of CD62L and CD127 on the RDH10-defective T cells was not observed. Thus it was found that RDH10 regulates the expression of these molecules via metabolism of vitamin A.

Example 3

Enhanced Differentiation and Suppressed Differentiation of T Cells (1) Enhancement of Differentiation by Retinoic Acid Human $CD4^+CD45RO^+$ T cells were stimulated by various methods (IL-2, anti-CD3/CD28 antibody, and anti-CD3/CD28 antibody and IL2), and cultured in the presence of DMSO (control) or all-trans retinoic acid (hereinafter retinoic acid used in all Examples described below is all-trans retinoic acid). As a result, in the cell population cultured in the presence of retinoic acid, the proportion of central memory cells (upper right in a graph) was decreased, and the proportion of terminal effector cells (left lower in a graph) was increased (FIG. 19). Such results show that the differentiation from central memory cells to effector memory cells, effector cells, and terminal effector cells is enhanced by retinoic acid.

(2) Resistance to Apoptosis

Human $CD4^+CD45RO^+$ T cells were cultured in the presence of DMSO (control), retinoic acid or an RAR antagonist (LE540) for 8 days, and then stimulated with an anti-Fas antibody (7C11). The proportion of apoptotic cells and the proportion of living cells were determined and analyzed. As a result, the apoptotic cells were increased and the living cells were decreased by enhancing the differentiation of cells by retinoic acid. In contrast, when the differentiation was suppressed by the RAR antagonist, the apoptotic cells were decreased and the living cells were increased (FIG. 20).

(3) Division Ability and Proliferation Ability of Memory T Cells

Human $CD4^+CD45RO^+$ T cells were stimulated with an anti-CD3/CD28 antibody, cultured in the presence of DMSO (control), retinoic acid or an RAR antagonist (LE540) for 8 days, re-stimulated with an anti-CD3/CD28 antibody and IL-2, or IL-7, and cultured. The division ability and proliferation ability of the T cells were evaluated. For evaluation of the division ability, Cell Trace (trade name) Violet Cell Proliferation Kit (manufactured by Life Technologies) was used. As a result, when the differentiation of T cells was enhanced by retinoic acid, both the division ability and the proliferation ability were decreased, whereas when the differentiation was suppressed by the RAR antagonist, both the division ability and the proliferation ability were increased (FIG. 21).

(4) Ability to Form Memory T Cell Population

Human CD4+CD45RO+ T cells were stimulated with an anti-CD3/CD28 antibody, cultured in the presence of DMSO (control), retinoic acid or an RAR antagonist (LE540) for 8 days, and re-stimulated and cultured with an anti-CD3/CD28 antibody and IL-2, or IL-7 for 7 days. The subsets of the T cells were identified. As a result, memory T cells appeared again with a high frequency from the T cell population cultured in the presence of the EAR antagonist. In contrast, when the T cells were cultured in the presence of DMSO or retinoic acid, the appearance frequency of memory T cells was low (FIG. 22).

Memory T cells have a multipotent ability and a capacity for self-renewal. By virtue of the capacity for self-renewal, a cell population comprising a high proportion of memory T cells can maintain the memory T cells with a high frequency even after repeating division and proliferation. Thus, the T cell population cultured in the presence of the BAR antagonist comprises a high proportion of memory T cells.

(5) Reformation Ability in Body of Mouse

Human CD4+CD45RO+ T cells were stimulated with an anti-CD3/CD28 antibody, cultured in the presence of DMSO (control), retinoic acid or an RAR antagonist (LE540) for 8 days, and then transferred together with human PBMC from which T cells were removed into the body of an immunodeficient mouse lacking T cells, B cells and NK cells (NOG mouse). After 4 weeks, T cells in the spleen of the mouse were analyzed. As a result, the human CD4+ T cells cultured in the presence of the RAR antagonist had a high ability to proliferate in the body of the immunodeficient mouse and were undifferentiated (FIG. 23).

Example 4

Increase in Proportion of Memory T Cells by RAR Antagonist

CD4+ T cells into which a human WT1$_{332}$-specific TCR gene was introduced were stimulated with human WT1$_{332}$, and cultured in the presence of DMSO (control), retinoic acid or an RAR antagonist (LE540). As a result, when the T cells were cultured in the presence of the RAR antagonist, the proportion of memory-type CD4+ T cells was increased (FIG. 24). Further, when the T cell population cultured in the presence of the RAR antagonist was re-stimulated with PBMC which had been pulsed with human WT1$_{332}$, and cultured (T cell: 30,000 cells/well; PBMC: 100,000 cells/well; IL-2: none), a high proliferation ability was shown as compared with the cells cultured in the presence of DMSO or retinoic acid (FIG. 24).

Example 5

Induction of Memory T Cells by RAR Antagonist
Method:

A terminal effector fraction contained in a human WT1$_{332}$-specific CD4+ T cell clone derived from a single cell was stimulated with dendritic cells which had been pulsed with human WT1$_{332}$, and cultured in the presence of DMSO (control), retinoic acid or an RAR antagonist (LE540) for 7 days. Then, the cells were labelled with CFSE, re-stimulated with dendritic cells which had been pulsed with human WT1$_{33}$, and further cultured in the presence of DMSO (control), retinoic acid or an RAR antagonist (LE540). After culturing for 4 or 6 days, the cells were subjected to an FACS analysis and a $^3$H-thymidine incorporation assay (cell proliferation assay). A flow chart of the experiment is shown in FIG. 25.

Results:

When the terminal effector CD4+ T cells were cultured in the presence of 10 μLE540, central memory CD4+ T cells were induced again (FIG. 26). Evaluation after the re-stimulation also showed that memory T cells having a high division ability and a high proliferation ability are generated by culture in the presence of LE540 (FIG. 27).

Example 6

Effect of RAR Antagonist in Cancer Immunotherapy
Method:

Tumor cells expressing both WT1 protein and luciferase were subcutaneously implanted into a ventral part of NOD/Shi-scid, IL-2Rγnull mice (NOG mice). Three days after the implantation, $10^4$ human WT1$_{332}$-specific CD4+ T cells (GPP positive) were injected intravenously (day 0). Eight hours after the intravenous injection, DMSO (control), retinoic acid or LE540 was administered intraperitoneally. One day after the intravenous injection, CD3+ T cells were removed, and 2×10$^6$ human peripheral blood mononuclear cells which had been pulsed with the human WT1$_{332}$ peptide were injected intravenously (day 1). Then, a survival period was observed. In addition, the amount of tumor was determined every week by administering luciferin which was a substrate for luciferase and measuring the intensity of emission induced by luciferase from outside the body. A flow chart of the experiment is shown in FIG. 28.

Results:

Survival curves and measurement results (day 21) of tumor amounts of the mice are shown in FIG. 29. In the retinoic acid administration group, the survival period was shortened as compared with the control. In contrast, in the LE540 administration group, the survival period was extended as compared with the control. Further, in the LE540 administration group, the tumor size was significantly small as compared with the DMSO group and the retinoic acid group (the tumor size was evaluated as an increase (-fold increase) relative to the tumor size on day 0). The results demonstrate that the antitumor effect caused by administration of a cancer antigen peptide such as a WT1 peptide, a cancer antigen peptide-specific T cell, an antigen-presenting cell pulsed with a cancer antigen peptide, or the like is enhanced by administration of an RAR antagonist.

Example 7

Modulation of Differentiation of T Cell Population by Various RAR Agonists and Antagonists
Method:

Human CD4+CD45RO+ T cells were stimulated with an anti-CD3/CD28 antibody and IL-2, and cultured in the presence of DMSO as a control, or various RAR agonists (FIG. 30) or RAR antagonists (FIG. 31) for 8 days.

Results:

In all of the cell populations cultured in the presence of all-trans retinoic acid (ATRA), and AM580, AC55649 and CD437 which were selective agonists for RARα, RARβ and RARγ respectively, the expression of CD62L which was a cell surface molecule characteristic of memory T cells was decreased and the proportion of memory T cells (CD62L+ CD127+ cells) was decreased (FIG. 30).

In contrast, in all of the cell populations cultured in the presence of LE540 which was an antagonist common to RARα, RARβ and RARγ, and BMS195614, LE135 and MM11253 which were selective antagonists for RARα, RARβ and RARγ respectively, the expression of CD62L was increased and the proportion of memory T cells (CB62L$^+$ CD127$^+$ cells) was increased (FIG. 31).

Example 8

Enhancement of Cytotoxic Activity by RAR Antagonist
Method:

CD4$^+$ T cells engineered to express an HLA-DPB1*05:01 (DP5)-restricted WT1$_{332}$-specific TCR (WT1$_{332}$-specific CD4$^+$ T cells) using a lentivirus vector were stimulated and cultured with human peripheral blood mononuclear cells which had been pulsed with WT1$_{332}$, in the presence of all-trans retinoic acid (ATRA), an RAR antagonist (LE540), or DMSO as a control. Eleven days after the initiation of culture, the cytotoxic activity of the WT1$_{332}$-specific CD4$^+$ T cells cultured under the above-described three conditions was measured using leukemia cell line TF1 expressing WT1 and having no HLA-DPB1*05:01 (TF1 is positive for HLA-DPB1*02:01 and HLA-DPB1*04:01) and TF1 engineered to express HLA-DPB1*05:01 (referred to as TF1-DP5) as targeting cells.

Results:

Regarding both the targeting cells of TF1 and TF1-DP5, the cytotoxic activity of the CD4$^+$ T cells was increased by culturing the CD4$^+$ T cells in the presence of the RAR antagonist (FIG. 32).

Example 9

Low-Molecular Inhibitor of Retinol Dehydrogenase 10

(1) Detection of RDH10 Protein

293 T cells (1×10$^6$), 293 T cells into which an RDH10 gene was introduced (1×10$^6$), and activated human CD4$^+$ T cells (1×10$^7$) were washed well with PBS, and then suspended in 600 µl of a 0.25 M sucrose/0.1 M sodium phosphate buffer (pH 7.4). The cell suspension was homogenized, and centrifuged at 10,000 g and 4° C. for 10 minutes. A supernatant was centrifuged at 10,000 g and 4° C. for an hour to obtain a microsomal fraction. The microsomal fraction was suspended in 20 µl of a 0.1 M sodium phosphate buffer (pH 7.4), and used for western blotting.

An RDH10 protein contained in the microsomal fraction was separated by SDS-PAGE, transferred onto a PVDF membrane, blocked, reacted with an anti-RDH10 antibody (ab87586) as a primary antibody and an anti-rabbit IgG-HRP antibody as a secondary antibody, and then detected using Luminata Forte Western HRP Substrate (manufactured by Millipore).

As a result, it was found that the microsomal fractions of the RDH10 gene-introduced 293 T cells and the activated human CD4$^+$ T cells contained the RDH10 protein (FIG. 33).

(2) Measurement of RDH10 Enzymatic Activity

All-trans retinol, BSA and NAD (nicotinamide adenine dinucleotide) as a co-enzyme were added to a reaction buffer (90 mM potassium phosphate buffer (pH 7.4), 40 mM KCl) so as to be respective final concentrations of 10 µM, 10 µM and 1 mM. This mixture was put in siliconized tubes in an amount of 200 µl/tube. Then, the microsomal fractions separated from the 293 T cells and the RDH10-expressed 293 T cells were added to the separate tubes in an amount of 10 µl/tube, and the tubes was kept at 37° C. for 15 minutes to react the mixture. After 200 µl of methanol was added to stop the reaction, retinoid was extracted with hexane and concentrated. The concentrated retinoid was dissolved in 150 µl of acetonitrile, and separated by HPLC. Ultraviolet absorption at a wavelength of 350 nm was detected to detect the substrate (all-trans retinol) and the product (all-trans retinal). Standard samples (all-trans retinol and all-trans retinal) were previously separated by HPLC and the retention time of each standard sample was determined. A solution of acetonitrile: 50 mM ammonium acetate=75:25 was used as a solvent for HPLC, and Syhergi 4u Hydro-RP 80A (manufactured by Phenomenex inc.) was used as a separation column. HPLC was performed at a flow rate of 2.0 ml/minute.

As a result, in the microsome derived from the 293 T cell line, all-trans retinal was not formed from all-trans retinol. In contrast, in the microsome derived from the RDH10 gene-introduced 293 T cell line, all-trans retinal was formed (FIG. 34).

(3) Inhibition of RDH10 Enzymatic Activity by Low-Molecular Inhibitor

All-trans retinol, BSA and NAD (nicotinamide adenine dinucleotide) as a co-enzyme were added to a reaction buffer (90 mM potassium phosphate buffer (pH 7.4), 40 mM KCl) so as to be respective final concentrations of 10 µM, 10 µM and 1 mM. This mixture was put in siliconized tubes in an amount of 200 µl/tube. Then, the microsomal fraction separated from the RDH10-expressed 293 T cells was added to the tubes in an amount of 10 µl/tube. RDH10 inhibitors (RDHI-001 to 011) dissolved in DMSO were added to the separate tubes so as to be a final concentration of 20 µM, and the same amount of DMSO as a control was added to the tube. The tubes were kept at 37° C. for 15 minutes to react the mixture. After 200 µl of methanol was added to stop the reaction, retinoid was extracted with hexane and concentrated. The concentrated retinoid was dissolved in 150 µl of acetonitrile, and separated by HPLC. Ultraviolet absorption at a wavelength of 350 nm was detected to detect the substrate (all-trans retinol) and the product (all-trans retinal). Standard samples (all-trans retinol and all-trans retinal) were previously separated by HPLC and the retention time of each standard sample was determined. A solution of acetonitrile: 50 mM ammonium acetate=75:25 was used as a solvent for HPLC, and Syhergi 4u Hydro-RP 80A (manufactured by Phenomenex Inc.) was used as a separation column. HPLC was performed at a flow rate of 2.0 ml/minute.

The enzymatic activity was calculated as a ratio of a wave form area of the product (all-trans retinal) to a wave form area of the unreacted substrate (all-trans retinoid). Numerical values relative to the enzymatic activity of the control are expressed as graphs (FIG. 35).

(4) In Vitro Amplification of Memory T Cells by RDH10 Inhibitor

Human CD4$^+$CD45RO$^+$ T cells (1×10$^5$/well) were cultured in the presence of an anti-CD3 antibody (2 µg/ml), an anti-CD28 antibody (2 µg/ml) and IL-2 (20 IU/ml) together with DMSO (control) or an RDH10 inhibitor (10 µM) for 8 days. Then, the frequency of memory T cells was determined by a FACS analysis.

As a result, when the T cells were cultured in the presence of RDH10 inhibitors (RDHI-001 to 004), the frequency of memory T cells (CD62L$^+$CD127$^+$) was increased (FIG. 36). The effects of the concentration of RDH10 inhibitors on the frequency of memory T cells are shown in FIG. 37.

(5) In Vivo Amplification of Memory T Cells by RDH10 Inhibitor

B6 mice in an RDH10 inhibitor administration group and a corn oil administration control group were infected with 1×10$^5$ cfu (colony formation unit) of recombinant *Listeria monocytogenes* expressing an OVA protein (LM-OVA) via a tail vein. An RDH10 inhibitor (200 µg/day) was continuously administered from the day before the infection (−1 day) to 7 days after the infection (day 7). Blood was collected from the tail vein over time (5, 7, 10 and 14 days after the infection), and OVA-specific CD8+ T cells contained in the peripheral blood were analyzed by a tetramer method. An outline of the experiment is shown in FIG. 38.

As a result of she analysis, it was found that the frequency of memory-type (CD62L+CD127+) OvA-specific CD8+ T cells is increased by administration of RDH10 inhibitors (RDHI-001 to 003) (FIGS. 39 and 40).

Example 10

Effect of Retinol Dehydrogenase 10 Inhibit or in Cancer Immunotherapy
Method:
EG7 tumor cells (EL4 cells expressing OVA protein) ($2\times10^6$ cells) were implanted into the abdomen of 86 mice by subcutaneous injection (0 day). Five days after the implantation, the mice were irradiated (3 Gy) to increase a survival rate of the implanted cells, and $2\times10^5$ cells of OT-ICD8+ T cells (OVA-specific CD8+ T cells) were intravenously injected. Then, 6, 8 and 10 days after the implantation, 100 μg/mouse of an RDH10 inhibitor (RDHI-001, RDHI-002, or RDHI-003) was intravenously injected. As a control, DMSO (DMSO 50 μl PBS 150 μl/mouse) which was a solvent for the RDH inhibitor was intravenously injected. A tumor volume was continuously determined by measuring the length of the major axis, the minor axis and the height using a caliper and calculating the formula; [(major axis)×(minor axis)×(height)/2]. A flow chart of the experiment is shown in FIG. 41.

In the tumor-implanted mice, OT-ICD8+ T cells were not transferred, and 5 days before the implantation, 0 day and 7 days after the implantation, 100 μg/mouse of an RDH10 inhibitor (RDHI-001, RDHI-002, or RDHI-003) was only intraperitoneally injected. As a control, corn oil (100 μg/100 μl/mouse) was intraperitoneally injected. In the same way as described above, a tumor volume was determined over time. A flow chart of the experiment is shown in FIG. 42.
Results:

Results of the tumor volume of the mice measured over time are shown in FIG. 43. All of 3 kinds of RDH10 inhibitors: RDHI-001, RDHI-002, and RDHI-003 suppressed the tumor growth. In Example 9 (5), the transferred OT-ICD8+ T cells (OVA-specific CD8+ T cells) were remarkably increased in the peripheral blood of the mice by administration of these inhibitors. In contrast, when the OT-ICD8+ T cells were not transferred and only the inhibitor was administered, the tumor growth-suppressing effect was not observed (FIG. 44). Thus, the tumor growth-suppressing effect by the RDH10 inhibitor is probably brought about via amplification of OT-ICD8+ T cells.

INDUSTRIAL APPLICABILITY

According to the present invention, a method of increasing the proportion of memory T cells in a T cell population using a modulator of a retinoid metabolic pathway and/or a modulator of a retinoic acid signaling system, an adjuvant for therapy and/or prevention of cancer or infection comprising the modulator, an immunopotentiating agent comprising the modulator, etc. are provided. These can be used in development and manufacture of pharmaceuticals for therapy and/or prevention of various diseases including cancer or infection, and in the field of development etc. of a method of treating the diseases, in particular, immunotherapy.

The invention claimed is:

1. A method of increasing proportion of memory T cells in a T cell population, the method comprising:
   inhibiting retinoic acid production in the T cell population by adding an inhibitor of a retinoid metabolic pathway to the T cell population,
   wherein the inhibitor is siRNA, shRNA, miRNA or antisense RNA that is capable of suppressing expression of a gene encoding retinol dehydrogenase 10; a nucleic acid molecule that produces the siRNA, the shRNA, the miRNA or the antisense RNA; a vector comprising the nucleic acid molecule; a compound that inhibits the action of retinol dehydrogenase 10 and has the formula (I) or a salt thereof; or a dominant negative mutant protein of retinol dehydrogenase 10 which is a protein capable of binding to a substrate of retinol dehydrogenase 10 and incapable of catalyzing a conversion of retinol to retinal:

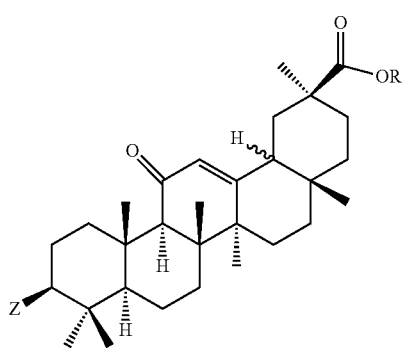

(I)

wherein R is H or $CH_3$,
Z is HO— or HOOC—Y—COO—, and
Y is —$CH_2CH_2$—, —CH=CH—, or a phenylene group,
provided that the compound having the formula (I) is not RDHI-005:

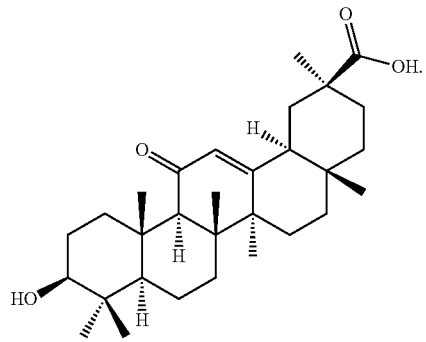

RDHI-005

2. The method of claim 1, wherein the inhibitor is a compound that inhibits the action of retinol dehydrogenase 10.

3. A method of treating cancer or infection, comprising:
   administering to a subject in need thereof an adjuvant comprising an inhibitor of a retinoid metabolic pathway,
   wherein the inhibitor is siRNA, shRNA, miRNA or antisense RNA that is capable of suppressing expression of a gene encoding retinol dehydrogenase 10; a nucleic acid molecule that produces the siRNA, the shRNA, the miRNA or the anti sense RNA; a vector comprising the nucleic acid molecule; a compound that inhibits the action of retinol dehydrogenase 10 and has the formula (I) or a salt thereof; or a dominant negative mutant protein of retinol dehydrogenase 10 which is a protein capable of binding to a substrate of retinol dehydrogenase 10 and incapable of catalyzing a conversion of retinol to retinal:

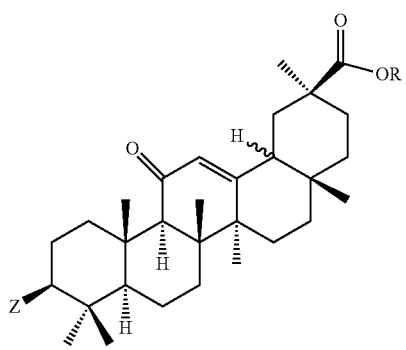

(I)

wherein R is H or CH$_3$,

Z is HO— or HOOC—Y—COO—, and

Y is —CH$_2$CH$_2$—, —CH=CH—, or a phenylene group, provided that the compound having the formula (I) is not RDHI-005:

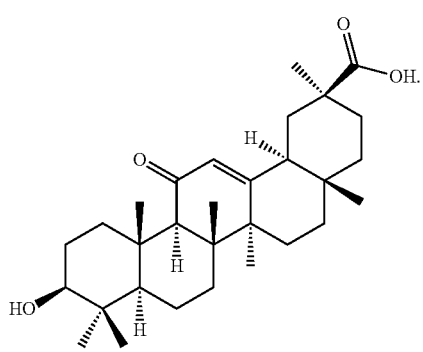

RDHI-005

4. An immunotherapeutic method for treating cancer, comprising:

administering to a subject in need thereof an adjuvant comprising an inhibitor of a retinoid metabolic pathway, wherein the inhibitor is siRNA, shRNA, miRNA or antisense RNA that is capable of suppressing expression of a gene encoding retinol dehydrogenase 10; a nucleic acid molecule that produces the siRNA, the shRNA, the miRNA or the antisense RNA; a vector comprising the nucleic acid molecule; a compound that inhibits the action of retinol dehydrogenase 10 and has the formula (I) or a salt thereof; or a dominant negative mutant protein of retinol dehydrogenase 10 which is a protein capable of binding to a substrate of retinol dehydrogenase 10 and incapable of catalyzing a conversion of retinol to retinal:

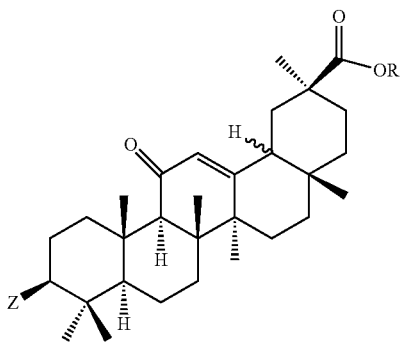

(I)

wherein R is H or CH$_3$,

Z is HO— or HOOC—Y—COO—, and

Y is —CH$_2$CH$_2$—, —CH=CH—, or a phenylene group, provided that the compound having the formula (I) is not RDHI-005:

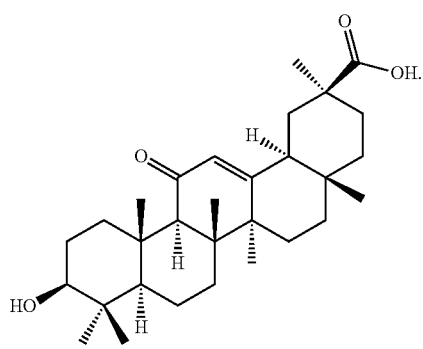

RDHI-005

5. A method of potentiating immunity of a subject, comprising:

administering to the subject an inhibitor of a retinoid metabolic pathway, wherein the inhibitor is siRNA, shRNA, miRNA or antisense RNA that is capable of suppressing expression of a gene encoding retinol dehydrogenase 10; a nucleic acid molecule that produces the siRNA, the shRNA, the miRNA or the anti sense RNA; a vector comprising the nucleic acid molecule; a compound that inhibits the action of retinol dehydrogenase 10 and has the formula (I) or a salt thereof; or a dominant negative mutant protein of retinol dehydrogenase 10 which is a protein capable of binding to a substrate of retinol dehydrogenase 10 and incapable of catalyzing a conversion of retinol to retinal:

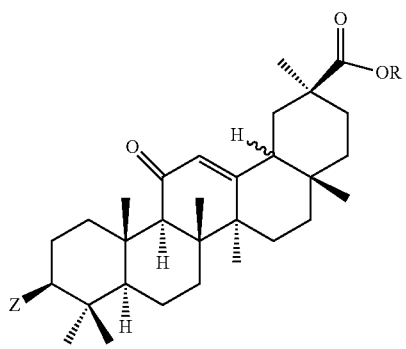

(I)

wherein R is H or CH$_3$,
Z is HO— or HOOC—Y—COO—, and
Y is —CH$_2$CH$_2$—, —CH=CH—, or a phenylene group,
provided that the compound having the formula (I) is not RDHI-005:

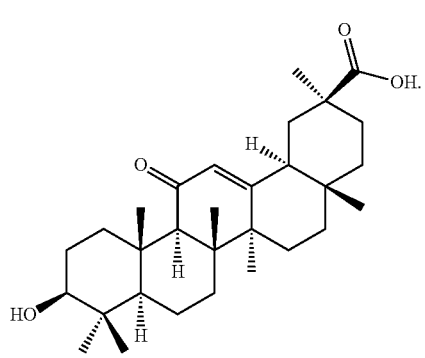

RDHI-005

6. A method of producing a T cell population, the method comprising:

increasing proportion of memory T cells in the T cell population by adding an inhibitor of a retinoid metabolic pathway to the T cell population, wherein the inhibitor is siRNA, shRNA, miRNA or antisense RNA that is capable of suppressing expression of a gene encoding retinol dehydrogenase 10; a nucleic acid molecule that produces the siRNA, the shRNA, the miRNA or the anti sense RNA; a vector comprising the nucleic acid molecule; a compound that inhibits the action of retinol dehydrogenase 10 and has the formula (I) or a salt thereof; or a dominant negative mutant protein of retinol dehydrogenase 10 which is a protein capable of binding to a substrate of retinol dehydrogenase 10 and incapable of catalyzing a conversion of retinol to retinal:

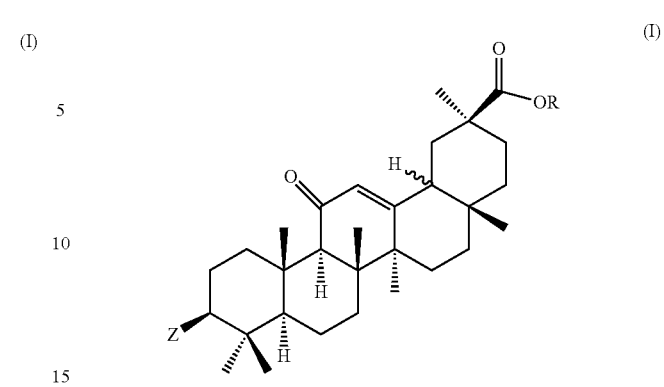

(I)

wherein R is H or CH$_3$,
Z is HO— or HOOC—Y—COO—, and
Y is —CH$_2$CH$_2$—, —CH=CH—, or a phenylene group.

7. The method of claim 1, wherein the inhibitor is siRNA, shRNA, or antisense RNA that is capable of suppressing expression of a gene encoding retinol dehydrogenase 10.

8. The method of claim 1, wherein the inhibitor is siRNA, shRNA, or antisense RNA that is capable of suppressing expression of a gene encoding retinal dehydrogenase 10; or a nucleic acid molecule that produces the siRNA, the shRNA, or the antisense RNA.

9. A method of increasing proportion of memory T cells in a T cell population, the method comprising:

adding an inhibitor of a retinoid metabolic pathway to the T cell population in vitro, wherein the inhibitor is siRNA, shRNA, miRNA or antisense RNA that is capable of suppressing expression of a gene encoding retinol dehydrogenase 10; a nucleic acid molecule that produces the siRNA, the shRNA, the miRNA or the antisense RNA; a vector comprising the nucleic acid molecule; a compound that inhibits the action of retinol dehydrogenase 10 and has the formula (I) or a salt thereof; or a dominant negative mutant protein of retinol dehydrogenase 10 which is a protein capable of binding to a substrate of retinol dehydrogenase 10 and incapable of catalyzing a conversion of retinol to retinal:

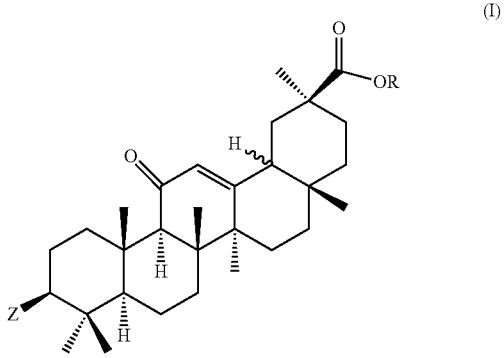

(I)

wherein R is H or CH$_3$,
Z is HO— or HOOC—Y—COO—, and
Y is —CH$_2$CH$_2$—, —CH=CH—, or a phenylene group.

10. The method of claim 1, wherein the inhibitor is siRNA, shRNA, miRNA or antisense RNA that is capable of suppressing expression of a gene encoding retinol dehydrogenase 10; a nucleic acid molecule that produces the siRNA, the shRNA, the miRNA or the antisense RNA; or a vector comprising the nucleic acid molecule.

11. The method of claim 1, wherein the inhibitor is siRNA, shRNA, miRNA or antisense RNA that is capable of suppressing expression of a gene encoding retinol dehydrogenase 10; a nucleic acid molecule that produces the siRNA, the shRNA, the miRNA or the antisense RNA; a vector comprising the nucleic acid molecule; or a compound that inhibits the action of retinol dehydrogenase 10 and has the formula (I) or a salt thereof:

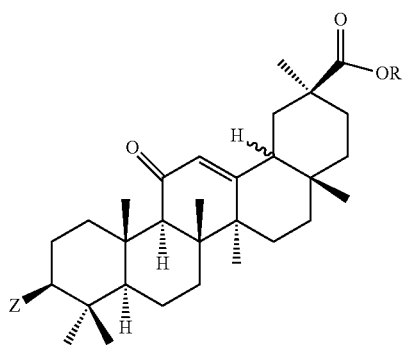
(I)

wherein R is H or CH$_3$,
Z is HO— or HOOC—Y—COO—, and
Y is —CH$_2$CH$_2$—, —CH=CH—, or a phenylene group,
provided that the compound having the formula (I) is not RDHI-005:

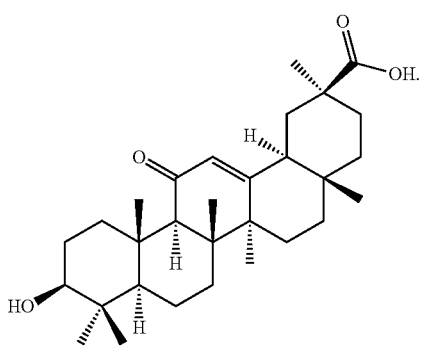
RDHI-005

* * * * *

SEQUENCE LISTING

```
<160> NUMBER OF SEQ ID NOS: 20

<210> SEQ ID NO 1
<211> LENGTH: 341
<212> TYPE: PRT
<213> ORGANISM: Homo sapiens

<400> SEQUENCE: 1

Met Asn Ile Val Val Glu Phe Phe Val Val Thr Phe Lys Val Leu Trp
1               5                   10                  15

Ala Phe Val Leu Ala Ala Ala Arg Trp Leu Val Arg Pro Lys Glu Lys
            20                  25                  30

Ser Val Ala Gly Gln Val Cys Leu Ile Thr Gly Ala Gly Ser Gly Leu
        35                  40                  45

Gly Arg Leu Phe Ala Leu Glu Phe Ala Arg Arg Arg Ala Leu Leu Val
    50                  55                  60

Leu Trp Asp Ile Asn Thr Gln Ser Asn Glu Glu Thr Ala Gly Met Val
65                  70                  75                  80

Arg His Ile Tyr Arg Asp Leu Glu Ala Ala Asp Ala Ala Leu Gln
                85                  90                  95

Ala Gly Asn Gly Glu Glu Glu Ile Leu Pro His Cys Asn Leu Gln Val
            100                 105                 110

Phe Thr Tyr Thr Cys Asp Val Gly Lys Arg Glu Asn Val Tyr Leu Thr
        115                 120                 125

Ala Glu Arg Val Arg Lys Glu Val Gly Glu Val Ser Val Leu Val Asn
    130                 135                 140
```

```
Asn Ala Gly Val Val Ser Gly His His Leu Leu Glu Cys Pro Asp Glu
145                 150                 155                 160

Leu Ile Glu Arg Thr Met Met Val Asn Cys His Ala His Phe Trp Thr
                165                 170                 175

Thr Lys Ala Phe Leu Pro Thr Met Leu Glu Ile Asn His Gly His Ile
            180                 185                 190

Val Thr Val Ala Ser Ser Leu Gly Leu Phe Ser Thr Ala Gly Val Glu
        195                 200                 205

Asp Tyr Cys Ala Ser Lys Phe Gly Val Val Gly Phe His Glu Ser Leu
    210                 215                 220

Ser His Glu Leu Lys Ala Ala Glu Lys Asp Gly Ile Lys Thr Thr Leu
225                 230                 235                 240

Val Cys Pro Tyr Leu Val Asp Thr Gly Met Phe Arg Gly Cys Arg Ile
                245                 250                 255

Arg Lys Glu Ile Glu Pro Phe Leu Pro Pro Leu Lys Pro Asp Tyr Cys
            260                 265                 270

Val Lys Gln Ala Met Lys Ala Ile Leu Thr Asp Gln Pro Met Ile Cys
        275                 280                 285

Thr Pro Arg Leu Met Tyr Ile Val Thr Phe Met Lys Ser Ile Leu Pro
    290                 295                 300

Phe Glu Ala Val Val Cys Met Tyr Arg Phe Leu Gly Ala Asp Lys Cys
305                 310                 315                 320

Met Tyr Pro Phe Ile Ala Gln Arg Lys Gln Ala Thr Asn Asn Asn Glu
                325                 330                 335

Ala Lys Asn Gly Ile
            340

<210> SEQ ID NO 2
<211> LENGTH: 3981
<212> TYPE: DNA
<213> ORGANISM: Homo sapiens
<220> FEATURE:
<221> NAME/KEY: CDS
<222> LOCATION: (689)..(1714)

<400> SEQUENCE: 2
agagccggcc cggagcgctc tgacttgcaa gcgggctgcg ctgcggagcc cagtgcccga      60
gtgacacccg cggagagtgc agggccgggg aacgcgagcc ctcggggggca gctgcaaggc    120 gttgggcagc gcttgcctgc gccgagcgag tctccccttc ccggcgctcc gccgccccgc    180
accccactct cccaccctct cgcaacttgg gtcgagttga caactcccgc ggcagccccgc    240 tggcccgtgc cgcctccgct gcgcaccccct ccccggggt gagagggagc cggcgcgccg    300
gttccgggga cgctcgggcg gcagcagctt ggcatgagg gcagttcgag tagtctaact    360
cgcggctgtc accgccactg cagcggagcc ggccggccgg gcgctgcggg acgggcgggc    420
ggctgccggc aggaggcgcc gagccgggtg actgccgcgg cgggcacagt ccggggccac    480
agcgccgagc ccgggcggga gtggcccccgc gcaggcaggg agcggcgccg cgcactccaa    540
cccggcgggc acctcggggg cgggcgcggg gcgcagcctt ctcgtcccgg cctctgtgac    600
aagcgccccg gagccgggag cccgattgcc gggctcgggg tgggcgcgga cgcaggcact    660
gggctcgtgc ggggcccccgg gcgtcgcg atg aac atc gtg gtg gag ttc ttc      712
                                 Met Asn Ile Val Val Glu Phe Phe
                                   1               5 gtg gtc act ttc aaa gtg ctc tgg gcg ttc gtg ctg gcc gcg gcg cgc      760
Val Val Thr Phe Lys Val Leu Trp Ala Phe Val Leu Ala Ala Ala Arg
```

```
                10                     15                      20
    tgg ctg gtg cgg ccc aag gag aag agc gtg gcg ggc cag gtg tgc ctc         808
    Trp Leu Val Arg Pro Lys Glu Lys Ser Val Ala Gly Gln Val Cys Leu
    25                   30                  35                  40 atc acc ggc gcc ggc agc ggc ctg ggc cgc ctc ttc gcg ctg gag ttc         856
    Ile Thr Gly Ala Gly Ser Gly Leu Gly Arg Leu Phe Ala Leu Glu Phe
                         45                  50                  55 gcc cgg cgt cgg gcg ctg ctg gtg ctg tgg gac atc aac acg caa agc         904
    Ala Arg Arg Arg Ala Leu Leu Val Leu Trp Asp Ile Asn Thr Gln Ser
                60                  65                  70 aac gag gag acg gct ggc atg gtg cgc cac atc tac cgc gac ctg gag         952
    Asn Glu Glu Thr Ala Gly Met Val Arg His Ile Tyr Arg Asp Leu Glu
            75                  80                  85 gcg gcc gac gcc gct gcg ctg caa gct ggg aat ggt gag gaa gaa att        1000
    Ala Ala Asp Ala Ala Ala Leu Gln Ala Gly Asn Gly Glu Glu Glu Ile
    90                  95                  100 ctg ccc cac tgt aac ttg cag gtt ttt acc tac acc tgt gac gtg ggg        1048
    Leu Pro His Cys Asn Leu Gln Val Phe Thr Tyr Thr Cys Asp Val Gly
    105                 110                 115                 120 aag agg gag aac gtc tac ctg acg gct gaa aga gtc cgc aag gag gtt        1096
    Lys Arg Glu Asn Val Tyr Leu Thr Ala Glu Arg Val Arg Lys Glu Val
                        125                 130                 135 ggc gaa gtc tca gtc ctg gtc aat aat gct ggt gtg gtc tct ggg cat        1144
    Gly Glu Val Ser Val Leu Val Asn Asn Ala Gly Val Val Ser Gly His
                140                 145                 150 cac ctt ctg gaa tgt cct gat gag ctc att gag aga acc atg atg gtc        1192
    His Leu Leu Glu Cys Pro Asp Glu Leu Ile Glu Arg Thr Met Met Val
            155                 160                 165 aat tgc cat gca cac ttc tgg acc act aag gct ttt ctt cct acg atg        1240
    Asn Cys His Ala His Phe Trp Thr Thr Lys Ala Phe Leu Pro Thr Met
    170                 175                 180 ctg gag att aat cat ggt cat att gtg aca gtt gca agt tcc ttg gga        1288
    Leu Glu Ile Asn His Gly His Ile Val Thr Val Ala Ser Ser Leu Gly
    185                 190                 195                 200 ttg ttc agt act gcc gga gtt gag gat tac tgt gcc agt aaa ttt gga        1336
    Leu Phe Ser Thr Ala Gly Val Glu Asp Tyr Cys Ala Ser Lys Phe Gly
                        205                 210                 215 gtt gtg ggt ttt cat gaa tcc ctg agc cat gaa cta aag gct gct gaa        1384
    Val Val Gly Phe His Glu Ser Leu Ser His Glu Leu Lys Ala Ala Glu
                220                 225                 230 aag gat gga att aaa aca acc ttg gtt tgc cct tat ctt gta gac act        1432
    Lys Asp Gly Ile Lys Thr Thr Leu Val Cys Pro Tyr Leu Val Asp Thr
            235                 240                 245 ggc atg ttc aga ggc tgc cga atc agg aaa gaa att gag cct ttt ctg        1480
    Gly Met Phe Arg Gly Cys Arg Ile Arg Lys Glu Ile Glu Pro Phe Leu
    250                 255                 260 cca cct ctg aag cct gat tac tgt gtg aag cag gcc atg aag gcc atc        1528
    Pro Pro Leu Lys Pro Asp Tyr Cys Val Lys Gln Ala Met Lys Ala Ile
    265                 270                 275                 280 ctc act gac cag ccc atg atc tgc act ccc cgc ctc atg tac atc gtg        1576
    Leu Thr Asp Gln Pro Met Ile Cys Thr Pro Arg Leu Met Tyr Ile Val
                        285                 290                 295 acc ttc atg aag agc atc cta cca ttt gaa gca gtt gtg tgc atg tat        1624
    Thr Phe Met Lys Ser Ile Leu Pro Phe Glu Ala Val Val Cys Met Tyr
                300                 305                 310 cgg ttc cta gga gcg gac aag tgt atg tac ccc ttt att gct caa aga        1672
    Arg Phe Leu Gly Ala Asp Lys Cys Met Tyr Pro Phe Ile Ala Gln Arg
            315                 320                 325 aag caa gcc aca aac aat aat gaa gca aaa aat gga atc taa               1714
    Lys Gln Ala Thr Asn Asn Asn Glu Ala Lys Asn Gly Ile
```

Lys Gln Ala Thr Asn Asn Asn Glu Ala Lys Asn Gly Ile
    330             335                 340

| | |
|---|---|
| gaatctttt gtatggaata ttacttctat cagaagatga tcaagatgtt tcagtccagt | 1774 |
| gcacatcagc attgctgaca ttttatggat tctaaacttg tgttgtttct tttttaaatc | 1834 |
| aactttttaa aaaataaag tgtaaattaa ccgactagag tacttggaaa atgtgatcag | 1894 |
| tacaagtgaa cttaggttgt tgccaacagg gtccttttag gcagaaccca gaaaccagtc | 1954 |
| aaatctgtag agaagcagtg tgacatcttc aggttaccat tattttttaa tgagcaggaa | 2014 |
| gtctagaaat gataactaga ctgtatgttt catgtgtgtg attttttcaga attcccagag | 2074 |
| tttactcatt cttgttatta aactctagcc agttgacatc ttcgcaattt caaggactga | 2134 |
| tagtgctgta ttttctcacg ttttctaagt ttccgttttg caaggcctag gtgactttt | 2194 |
| catggtgttt gtatgtttag ctcttttgaa aaggaattt gaaatctcca tcaactgaag | 2254 |
| taaatgatgt ctgagtgtta cagtaaaggt gaccaagtct cttttcttaaa gtcacaatga | 2314 |
| ctaaagtatt agttgaattt tttttttttt tttttttgatg gagtctcgct ctgtcaccag | 2374 |
| gctggagtgc agtagcacaa tcacggctca ctgcaatctc tgcctcccag tttcaagtga | 2434 |
| ttctgctgtc tcagcctccc aagtagctgg gactacaggc atgcgccacc acgcccagct | 2494 |
| aattttttgta ttttttagtag agacgggtt tcaccatgtt ggtcaggatg gtctccatct | 2554 |
| cttgacattg tgatccacct gcctcggcct cccaaagtgc tgggattaca ggcatgagcc | 2614 |
| actgcaccca gccttgaatt tttaattta tctctgatat acttcattaa gtgtctggag | 2674 |
| acctaattat cctaaaagat catacatttt ctacctatga attttgctgc atacagaaag | 2734 |
| tgccctttcc tcaggaagtt gctgtgtttc atttctttgg atggactctt atctagaata | 2794 |
| catagcagct ctgcaaagga acagttttta aaaatgggaa cttctacatt gaaaagtccc | 2854 |
| cattttttgtg ccaactatga ttagtgagag gaagaaatct tattctatgg catatgtatg | 2914 |
| gaagggtgta aagattcttt tgaaaggttt attcacattg tagaacagca aatgacattt | 2974 |
| ttacagtatt tttttgtaaa gcaaactatt ttgtgccttg aattttggtat atgtgtatta | 3034 |
| gtgaaacatt gtaaaggtga acttctacct ctgtatctaa atgtatacca tccacttgta | 3094 |
| aatgactata aactattatg tgattgcttt tttttttaga atgtcttgtt taaatagtgg | 3154 |
| ccaatgttta aggctgttaa aataagccaa cttttactaa ttggggagtt ttataaatga | 3214 |
| ctgattaaat ttaagaatt aacttacatg caattgtgtg attattagtt atcagcagtg | 3274 |
| ttgtaaggaa aattattgtg ttttttttta tgatcattat cccactttag gtaaagaaaa | 3334 |
| atattggaat ggaatagtgt tgggaaacag acattaacaa cctagggtgc ctgcactcaa | 3394 |
| atagccgatg ttactgtccc tagattagag acttgattaa gggcttgttt gtaccaaaag | 3454 |
| tggggaaaca atgccatgac ctgtgtttta gtttggctgc accacagatc aaatctgcac | 3514 |
| tgtgtctaca tataggaaag gtcctggtgt gtgctaatgt tcccaatgca ggacttgagg | 3574 |
| aagagctctg ttatatgttt ccatttctct ttatcaaaga taaccaaacc ttatggccct | 3634 |
| tataacaatg gaggcactgg ctgcctctta attttcaatc atggacctaa agaagtactc | 3694 |
| tgaagggtct caacaatgcc aggtggggac agatatactc agagattatc caggtctgcc | 3754 |
| tcccagcgag cctggagtac accagaccct cctagagaaa tctgttataa tttaacaacc | 3814 |
| cacttatcca ccttaaaact gaggaaagtc gtctttacat ctaattttat tcttgtgtgt | 3874 |
| tataacttaa acctattct attttttgttt gttattgccc ttataagggt gtccatctcc | 3934 |
| aagttcaata aactaattca tttaacttta aaaaaaaaaa aaaaaa | 3981 |

```
<210> SEQ ID NO 3
<211> LENGTH: 21
<212> TYPE: RNA
<213> ORGANISM: Artificial sequence
<220> FEATURE:
<223> OTHER INFORMATION: shRNA sense strand 5' to 3'

<400> SEQUENCE: 3
gcacacuucu ggaccacuaa g                                              21

<210> SEQ ID NO 4
<211> LENGTH: 21
<212> TYPE: RNA
<213> ORGANISM: Artificial sequence
<220> FEATURE:
<223> OTHER INFORMATION: shRNA antisense strand 5' to 3'

<400> SEQUENCE: 4
cuuagugguc cagaagugug c                                              21

<210> SEQ ID NO 5
<211> LENGTH: 3301
<212> TYPE: DNA
<213> ORGANISM: Homo sapiens
<220> FEATURE:
<221> NAME/KEY: CDS
<222> LOCATION: (479)..(1867)

<400> SEQUENCE: 5
gtgcctcttg cagcagccta acccagaagc agggggggaat cctgaatcga gctgagaggg     60
cttccccggt tctcctggga accccatcgg cccccctgcca gcacacacct gagcagcatc    120
acaggacatg gccccctcag ccacctagct ggggcccatc taggagtggc atctttttg      180 gtgccctgaa ggccagctct ggaccttccc aggaaaagtg ccagctcaca gaactgcttg    240
accaaaggac cggctcttga gacatccccc aacccacctg gccccagct agggtgggg      300 ctccaggaga ctgagattag cctgccctct ttggacagca gctccaggac agggcgggtg    360
ggctgaccac ccaaacccca tctgggccca ggcccatgc cccgaggagg ggtggtctga     420
agcccaccag agcccctgc cagactgtct gcctcccttc tgactgtggc cgcttggc       478 atg gcc agc aac agc agc tcc tgc ccg aca cct ggg ggc ggg cac ctc      526
Met Ala Ser Asn Ser Ser Ser Cys Pro Thr Pro Gly Gly Gly His Leu
 1               5                  10                  15 aat ggg tac ccg gtg cct ccc tac gcc ttc ttc ttc ccc cct atg ctg      574
Asn Gly Tyr Pro Val Pro Pro Tyr Ala Phe Phe Phe Pro Pro Met Leu
             20                  25                  30 ggt gga ctc tcc ccg cca ggc gct ctg acc act ctc cag cac cag ctt      622
Gly Gly Leu Ser Pro Pro Gly Ala Leu Thr Thr Leu Gln His Gln Leu
         35                  40                  45 cca gtt agt gga tat agc aca cca tcc cca gcc acc att gag acc cag      670
Pro Val Ser Gly Tyr Ser Thr Pro Ser Pro Ala Thr Ile Glu Thr Gln
     50                  55                  60 agc agc agt tct gaa gag ata gtg ccc agc cct ccc tcg cca ccc cct      718
Ser Ser Ser Ser Glu Glu Ile Val Pro Ser Pro Pro Ser Pro Pro Pro
 65                  70                  75                  80 cta ccc cgc atc tac aag cct tgc ttt gtc tgt cag gac aag tcc tca      766
Leu Pro Arg Ile Tyr Lys Pro Cys Phe Val Cys Gln Asp Lys Ser Ser
                 85                  90                  95 ggc tac cac tat ggg gtc agc gcc tgt gag ggc tgc aag ggc ttc ttc      814
Gly Tyr His Tyr Gly Val Ser Ala Cys Glu Gly Cys Lys Gly Phe Phe
            100                 105                 110
```

-continued

| | | |
|---|---|---|
| cgc cgc agc atc cag aag aac atg gtg tac acg tgt cac cgg gac aag<br>Arg Arg Ser Ile Gln Lys Asn Met Val Tyr Thr Cys His Arg Asp Lys<br>       115                       120                       125 | 862 |
| aac tgc atc atc aac aag gtg acc cgg aac cgc tgc cag tac tgc cga<br>Asn Cys Ile Ile Asn Lys Val Thr Arg Asn Arg Cys Gln Tyr Cys Arg<br>130                      135                        140 | 910 |
| ctg cag aag tgc ttt gaa gtg ggc atg tcc aag gag tct gtg aga aac<br>Leu Gln Lys Cys Phe Glu Val Gly Met Ser Lys Glu Ser Val Arg Asn<br>145                      150                        155                    160 | 958 |
| gac cga aac aag aag aag aag gag gtg ccc aag ccc gag tgc tct gag<br>Asp Arg Asn Lys Lys Lys Lys Glu Val Pro Lys Pro Glu Cys Ser Glu<br>                       165                       170                       175 | 1006 |
| agc tac acg ctg acg ccg gag gtg ggg gag ctc att gag aag gtg cgc<br>Ser Tyr Thr Leu Thr Pro Glu Val Gly Glu Leu Ile Glu Lys Val Arg<br>                  180                        185                       190 | 1054 |
| aaa gcg cac cag gaa acc ttc cct gcc ctc tgc cag ctg ggc aaa tac<br>Lys Ala His Gln Glu Thr Phe Pro Ala Leu Cys Gln Leu Gly Lys Tyr<br>                       195                        200                       205 | 1102 |
| act acg aac aac agc tca gaa caa cgt gtc tct ctg gac att gac ctc<br>Thr Thr Asn Asn Ser Ser Glu Gln Arg Val Ser Leu Asp Ile Asp Leu<br>210                      215                        220 | 1150 |
| tgg gac aag ttc agt gaa ctc tcc acc aag tgc atc att aag act gtg<br>Trp Asp Lys Phe Ser Glu Leu Ser Thr Lys Cys Ile Ile Lys Thr Val<br>225                      230                        235                    240 | 1198 |
| gag ttc gcc aag cag ctg ccc ggc ttc acc acc ctc acc atc gcc gac<br>Glu Phe Ala Lys Gln Leu Pro Gly Phe Thr Thr Leu Thr Ile Ala Asp<br>                                    245                       250                       255 | 1246 |
| cag atc acc ctc ctc aag gct gcc tgc ctg gac atc ctg atc ctg cgg<br>Gln Ile Thr Leu Leu Lys Ala Ala Cys Leu Asp Ile Leu Ile Leu Arg<br>                             260                       265                       270 | 1294 |
| atc tgc acg cgg tac acg ccc gag cag gac acc atg acc ttc tcg gac<br>Ile Cys Thr Arg Tyr Thr Pro Glu Gln Asp Thr Met Thr Phe Ser Asp<br>                         275                       280                       285 | 1342 |
| ggg ctg acc ctg aac cgg acc cag atg cac aac gct ggc ttc ggc ccc<br>Gly Leu Thr Leu Asn Arg Thr Gln Met His Asn Ala Gly Phe Gly Pro<br>                  290                       295                       300 | 1390 |
| ctc acc gac ctg gtc ttt gcc ttc gcc aac cag ctg ctg ccc ctg gag<br>Leu Thr Asp Leu Val Phe Ala Phe Ala Asn Gln Leu Leu Pro Leu Glu<br>305                      310                        315                    320 | 1438 |
| atg gat gat gcg gag acg ggg ctg ctc agc gcc atc tgc ctc atc tgc<br>Met Asp Asp Ala Glu Thr Gly Leu Leu Ser Ala Ile Cys Leu Ile Cys<br>                             325                       330                       335 | 1486 |
| gga gac cgc cag gac ctg gag cag ccg gac cgg gtg gac atg ctg cag<br>Gly Asp Arg Gln Asp Leu Glu Gln Pro Asp Arg Val Asp Met Leu Gln<br>                       340                       345                       350 | 1534 |
| gag ccg ctg ctg gag gcg cta aag gtc tac gtg cgg aag cgg agg ccc<br>Glu Pro Leu Leu Glu Ala Leu Lys Val Tyr Val Arg Lys Arg Arg Pro<br>                   355                       360                      365 | 1582 |
| agc cgc ccc cac atg ttc ccc aag atg cta atg aag att act gac ctg<br>Ser Arg Pro His Met Phe Pro Lys Met Leu Met Lys Ile Thr Asp Leu<br>370                      375                       380 | 1630 |
| cga agc atc agc gcc aag ggg gct gag cgg gtg atc acg ctg aag atg<br>Arg Ser Ile Ser Ala Lys Gly Ala Glu Arg Val Ile Thr Leu Lys Met<br>385                      390                        395                    400 | 1678 |
| gag atc ccg ggc tcc atg ccg cct ctc atc cag gaa atg ttg gag aac<br>Glu Ile Pro Gly Ser Met Pro Pro Leu Ile Gln Glu Met Leu Glu Asn<br>                       405                       410                    415 | 1726 |
| tca gag ggc ctg gac act ctg agc gga cag ccg ggg ggt ggg ggg cgg<br>Ser Glu Gly Leu Asp Thr Leu Ser Gly Gln Pro Gly Gly Gly Gly Arg<br>                     420                       425                       430 | 1774 |

-continued

| gac ggg ggt ggc ctg gcc ccc ccg cca ggc agc tgt agc ccc agc ctc | 1822 |
| Asp Gly Gly Gly Leu Ala Pro Pro Pro Gly Ser Cys Ser Pro Ser Leu | |
| 435 440 445 | |

| agc ccc agc tcc aac aga agc agc ccg gcc acc cac tcc ccg tga | 1867 |
| Ser Pro Ser Ser Asn Arg Ser Ser Pro Ala Thr His Ser Pro | |
| 450 455 460 | |

| ccgcccacgc cacatggaca cagccctcgc cctccgcccc ggcttttctc tgcctttcta | 1927 |
| ccgaccatgt gaccccgcac cagccctgcc cccacctgcc ctcccgggca gtactgggga | 1987 |
| ccttccctgg gggacgggga gggaggaggc agcgactcct ggacagagg cctgggccct | 2047 |
| cagtggactg cctgctccca cagcctgggc tgacgtcaga ggccgaggcc aggaactgag | 2107 |
| tgaggcccct ggtcctgggt ctcaggatgg gtcctggggg cctcgtgttc atcaagacac | 2167 |
| ccctctgccc agctcaccac atcttcatca ccagcaaacg ccaggacttg ctcccccat | 2227 |
| cctcagaact cacaagccat tgctccccag ctggggaacc tcaacctccc cctgcctcg | 2287 |
| gttggtgaca gaggggtgg gacagggcg ggggttccc cctgtacata ccctgccata | 2347 |
| ccaaccccag gtattaattc tcgctggttt tgttttatt ttaatttttt tgttttgatt | 2407 |
| ttttaataa gaattttcat tttaagcaca tttatactga aggaatttgt gctgtgtatt | 2467 |
| gggggagct ggatccagag ctggagggg tgggtccggg ggagggagtg gctcggaagg | 2527 |
| ggcccccact ctcctttcat gtccctgtgc ccccagttc tcctcctcag ccttttcctc | 2587 |
| ctcagttttc tctttaaaac tgtgaagtac taactttcca aggcctgcct tccctccct | 2647 |
| cccactggag aagccgccag ccctttctc cctctgcctg accactgggt gtggacggtg | 2707 |
| tggggcagcc ctgaaaggac aggctcctgg ccttggcact tgcctgcacc caccatgagg | 2767 |
| catggagcag ggcagagcaa ggccccggg acagagtttt cccagacctg gctcctcggc | 2827 |
| agagctgcct cccgtcaggg cccacatcat ctaggctccc cagcccccac tgtgaagggg | 2887 |
| ctggccaggg gccgagctg ccccaccc cggcctcagc caccagcacc cccatagggc | 2947 |
| ccccagacac cacacacatg cgcgtgcgca cacacacaaa cacacacaca ctggacagta | 3007 |
| gatgggccga cacacacttg gcccgagttc ctccatttcc ctggcctgcc cccaccccc | 3067 |
| aacctgtccc accccgtgc cccctcctta ccccgcagga cgggcctaca gggggtctc | 3127 |
| ccctcacccc tgcacccca gctgggggag ctggctctgc cccgacctcc ttcaccaggg | 3187 |
| gttgggccc cttcccctgg agcccgtggg tgcacctgtt actgttgggc tttccactga | 3247 |
| gatctactgg ataaagaata aagttctatt tattctaaaa aaaaaaaaa aaaa | 3301 |

<210> SEQ ID NO 6
<211> LENGTH: 3494
<212> TYPE: DNA
<213> ORGANISM: Homo sapiens
<220> FEATURE:
<221> NAME/KEY: CDS
<222> LOCATION: (687)..(2060)

<400> SEQUENCE: 6

| ctcggttccc tgcgtttctc ccgctgcagc cggacgcgcc gggaatgggt taagccaggg | 60 |
| gcggtgcctg gacggggcgg ggcggtggaa aggggtggt gccggaggg gaggggcgc | 120 |
| gcagagctgg ggtggggggg ccgtggcgcg taccaccaga gaccgagcga gtcgccagct | 180 |
| gcccctggcc tggcggggc ggaaccgcgc gggatcccca cccccacccg gaatcctcgc | 240 |
| cacggagaat ccctgagaa gcccggatc cccggctggg aggaggaagt gctcgttgac | 300 |
| ccccagcccc gcgctgatcc cgcccccggc ctgcggactt ggggagccgc tgtactctgc | 360 |

```
ctcggacgcc acgagactct agacgggagt cccctcgagg tgaagccgct gagttcccgg     420
gccccgccag gcttccctgg gagagccgac ggaccccccc tcccagcaca cacaacttcc     480
ctgcttttca ccgggactgg cggagcggcc ggcggactta gacgcgggga cttcagggca     540
gggggcgccc cctgcccggg tcaccagtcg gggcgagggg acgtctcctc tcccccagct     600
gctctgctcg gatggcgccg ccggctgagt gacggggggcg gcgcgcagga cttcccagct     660
cggacctctt gccttcgagg ggaaag atg tac gag agt gta gaa gtg ggg ggt     713
                             Met Tyr Glu Ser Val Glu Val Gly Gly
                              1               5 ccc acc cct aat ccc ttc cta gtg gtg gat ttt tat aac cag aac cgg     761
Pro Thr Pro Asn Pro Phe Leu Val Val Asp Phe Tyr Asn Gln Asn Arg
 10              15                  20                  25 gcc tgt ttg ctc cca gag aag ggg ctc ccc gcc ccg ggt ccg tac tcc     809
Ala Cys Leu Leu Pro Glu Lys Gly Leu Pro Ala Pro Gly Pro Tyr Ser
             30                  35                  40 acc ccg ctc cgg act ccg ctt tgg aat ggc tca aac cac tcc att gag     857
Thr Pro Leu Arg Thr Pro Leu Trp Asn Gly Ser Asn His Ser Ile Glu
         45                  50                  55 acc cag agc agc agt tct gaa gag ata gtg ccc agc cct ccc tcg cca     905
Thr Gln Ser Ser Ser Ser Glu Glu Ile Val Pro Ser Pro Pro Ser Pro
     60                  65                  70 ccc cct cta ccc cgc atc tac aag cct tgc ttt gtc tgt cag gac aag     953
Pro Pro Leu Pro Arg Ile Tyr Lys Pro Cys Phe Val Cys Gln Asp Lys
 75                  80                  85 tcc tca ggc tac cac tat ggg gtc agc gcc tgt gag ggc tgc aag ggc    1001
Ser Ser Gly Tyr His Tyr Gly Val Ser Ala Cys Glu Gly Cys Lys Gly
 90                  95                 100                 105 ttc ttc cgc cgc agc atc cag aag aac atg gtg tac acg tgt cac cgg    1049
Phe Phe Arg Arg Ser Ile Gln Lys Asn Met Val Tyr Thr Cys His Arg
                110                 115                 120 gac aag aac tgc atc atc aac aag gtg acc cgg aac cgc tgc cag tac    1097
Asp Lys Asn Cys Ile Ile Asn Lys Val Thr Arg Asn Arg Cys Gln Tyr
            125                 130                 135 tgc cga ctg cag aag tgc ttt gaa gtg ggc atg tcc aag gag tct gtg    1145
Cys Arg Leu Gln Lys Cys Phe Glu Val Gly Met Ser Lys Glu Ser Val
        140                 145                 150 aga aac gac cga aac aag aag aag aag gag gtg ccc aag ccc gag tgc    1193
Arg Asn Asp Arg Asn Lys Lys Lys Lys Glu Val Pro Lys Pro Glu Cys
155                 160                 165 tct gag agc tac acg ctg acg ccg gag gtg ggg gag ctc att gag aag    1241
Ser Glu Ser Tyr Thr Leu Thr Pro Glu Val Gly Glu Leu Ile Glu Lys
170                 175                 180                 185 gtg cgc aaa gcg cac cag gaa acc ttc cct gcc ctc tgc cag ctg ggc    1289
Val Arg Lys Ala His Gln Glu Thr Phe Pro Ala Leu Cys Gln Leu Gly
                190                 195                 200 aaa tac act acg aac aac agc tca gaa caa cgt gtc tct ctg gac att    1337
Lys Tyr Thr Thr Asn Asn Ser Ser Glu Gln Arg Val Ser Leu Asp Ile
            205                 210                 215 gac ctc tgg gac aag ttc agt gaa ctc tcc acc aag tgc atc att aag    1385
Asp Leu Trp Asp Lys Phe Ser Glu Leu Ser Thr Lys Cys Ile Ile Lys
        220                 225                 230 act gtg gag ttc gcc aag cag ctg ccc ggc ttc acc acc ctc acc atc    1433
Thr Val Glu Phe Ala Lys Gln Leu Pro Gly Phe Thr Thr Leu Thr Ile
235                 240                 245 gcc gac cag atc acc ctc ctc aag gct gcc tgc ctg gac atc ctg atc    1481
Ala Asp Gln Ile Thr Leu Leu Lys Ala Ala Cys Leu Asp Ile Leu Ile
250                 255                 260                 265
```

-continued

| | | |
|---|---|---|
| ctg cgg atc tgc acg cgg tac acg ccc gag cag gac acc atg acc ttc<br>Leu Arg Ile Cys Thr Arg Tyr Thr Pro Glu Gln Asp Thr Met Thr Phe<br>270                     275                       280 | 1529 |
| tcg gac ggg ctg acc ctg aac cgg acc cag atg cac aac gct ggc ttc<br>Ser Asp Gly Leu Thr Leu Asn Arg Thr Gln Met His Asn Ala Gly Phe<br>285                     290                       295 | 1577 |
| ggc ccc ctc acc gac ctg gtc ttt gcc ttc gcc aac cag ctg ctg ccc<br>Gly Pro Leu Thr Asp Leu Val Phe Ala Phe Ala Asn Gln Leu Leu Pro<br>300                     305                      310 | 1625 |
| ctg gag atg gat gat gcg gag acg ggg ctg ctc agc gcc atc tgc ctc<br>Leu Glu Met Asp Asp Ala Glu Thr Gly Leu Leu Ser Ala Ile Cys Leu<br>315                     320                       325 | 1673 |
| atc tgc gga gac cgc cag gac ctg gag cag ccg gac cgg gtg gac atg<br>Ile Cys Gly Asp Arg Gln Asp Leu Glu Gln Pro Asp Arg Val Asp Met<br>330                335                   340                  345 | 1721 |
| ctg cag gag ccg ctg ctg gag gcg cta aag gtc tac gtg cgg aag cgg<br>Leu Gln Glu Pro Leu Leu Glu Ala Leu Lys Val Tyr Val Arg Lys Arg<br>350                     355                       360 | 1769 |
| agg ccc agc cgc ccc cac atg ttc ccc aag atg cta atg aag att act<br>Arg Pro Ser Arg Pro His Met Phe Pro Lys Met Leu Met Lys Ile Thr<br>365                     370                       375 | 1817 |
| gac ctg cga agc atc agc gcc aag ggg gct gag cgg gtg atc acg ctg<br>Asp Leu Arg Ser Ile Ser Ala Lys Gly Ala Glu Arg Val Ile Thr Leu<br>380                     385                       390 | 1865 |
| aag atg gag atc ccg ggc tcc atg ccg cct ctc atc cag gaa atg ttg<br>Lys Met Glu Ile Pro Gly Ser Met Pro Pro Leu Ile Gln Glu Met Leu<br>395                     400                       405 | 1913 |
| gag aac tca gag ggc ctg gac act ctg agc gga cag ccg ggg ggt ggg<br>Glu Asn Ser Glu Gly Leu Asp Thr Leu Ser Gly Gln Pro Gly Gly Gly<br>410                     415                       420                  425 | 1961 |
| ggg cgg gac ggg ggt ggc ctg gcc ccc ccg cca ggc agc tgt agc ccc<br>Gly Arg Asp Gly Gly Gly Leu Ala Pro Pro Gly Ser Cys Ser Pro<br>430                     435                       440 | 2009 |
| agc ctc agc ccc agc tcc aac aga agc agc ccg gcc acc cac tcc ccg<br>Ser Leu Ser Pro Ser Ser Asn Arg Ser Ser Pro Ala Thr His Ser Pro<br>445                     450                       455 | 2057 |
| tga ccgcccacgc cacatggaca cagccctcgc cctccgcccc ggcttttctc | 2110 |
| tgcctttcta ccgaccatgt gaccccgcac cagccctgcc cccacctgcc ctcccgggca | 2170 |
| gtactgggga ccttccctgg gggacgggga gggaggaggc agcgactcct tggacagagg | 2230 |
| cctgggccct cagtggactg cctgctccca cagcctgggc tgacgtcaga ggccgaggcc | 2290 |
| aggaactgag tgaggcccct ggtcctgggt tcaggatgg gtcctggggg cctcgtgttc | 2350 |
| atcaagacac ccctctgccc agctcaccac atcttcatca ccagcaaacg ccaggacttg | 2410 |
| gctcccccat cctcagaact cacaagccat tgctccccag ctggggaacc tcaacctccc | 2470 |
| ccctgcctcg gttggtgaca gagggggtgg gacaggggcg gggggttccc cctgtacata | 2530 |
| ccctgccata ccaaccccag gtattaattc tcgctggttt tgtttttatt ttaattttt | 2590 |
| tgttttgatt tttttaataa gaattttcat tttaagcaca tttatactga aggaatttgt | 2650 |
| gctgtgtatt gggggagct ggatccagag ctggagggg tgggtccggg ggagggagtg | 2710 |
| gctcggaagg ggccccact ctcctttcat gtccctgtgc cccccagttc tcctcctcag | 2770 |
| ccttttcctc ctcagttttc tctttaaaac tgtgaagtac taactttcca aggcctgcct | 2830 |
| tcccctccct cccactggag aagccgccac cccctttctc cctctgcctg accactgggt | 2890 |
| gtggacggtg tggggcagcc ctgaaaggac aggctcctgg ccttggcact tgcctgcacc | 2950 |
| caccatgagg catggagcag ggcagagcaa gggcccgggg acagagtttt cccagacctg | 3010 |

-continued

```
gctcctcggc agagctgcct cccgtcaggg cccacatcat ctaggctccc cagccccac       3070 tgtgaagggg ctggccaggg gcccgagctg ccccacccc cggcctcagc caccagcacc       3130
cccatagggc ccccagacac cacacacatg cgcgtgcgca cacacacaaa cacacacaca      3190
ctggacagta gatgggccga cacacacttg gcccgagttc ctccatttcc ctggcctgcc      3250
ccccaccccc aacctgtccc accccgtgc ccctccttaa ccccgcagga cgggcctaca      3310
ggggggtctc ccctcacccc tgcaccccca gctgggggag ctggctctgc cccgacctcc     3370
ttcaccaggg gttggggccc cttcccctgg agcccgtggg tgcacctgtt actgttgggc     3430
tttccactga gatctactgg ataaagaata aagttctatt tattctaaaa aaaaaaaaaa     3490
aaaa                                                                  3494
```

<210> SEQ ID NO 7
<211> LENGTH: 3122
<212> TYPE: DNA
<213> ORGANISM: Homo sapiens
<220> FEATURE:
<221> NAME/KEY: CDS
<222> LOCATION: (591)..(1688)

<400> SEQUENCE: 7

```
ctgctccgta ccctccgccc cttcagtctg gggctccggg taaagtttca gcctccgcac       60
gtgactcgct atggccgctg ccatcgcccc gcgcccctga gccgcggccc cctggacggc      120
tcctctcccg ggaccccgca ccctgatgcc gagcagcacc agggcgccgg gttagggcag      180
acgctgtgct cgctggcacc ccgaacgggt tgcttccccc gctgcgagca tcacaggaca      240 tggcccctc agccacctag ctggggccca tctaggagtg gcatcttttt tggtgccctg       300
aaggccagct ctggaccttc ccaggaaaag tgccagctca cagaactgct tgaccaaagg      360
accggctctt gagacatccc ccaacccacc tggcccccag ctagggtggg ggctccagga      420
gactgagatt agcctgccct cttggacag cagctccagg acagggcggg tgggctgacc       480
acccaaaccc catctgggcc caggccccat gccccgagga ggggtggtct gaagcccacc      540 agagcccct gccagactgt ctgcctccct tctgactgtg ccgcttggc atg gcc           596
                                                           Met Ala
                                                             1
```

```
agc aac agc agc tcc tgc ccg aca cct ggg ggc ggg cac ctc aat ggg        644
Ser Asn Ser Ser Ser Cys Pro Thr Pro Gly Gly Gly His Leu Asn Gly
        5                  10                  15
```

```
tac ccg gtg cct ccc tac gcc ttc ttc ttc ccc cct atg ctg ggt gga        692
Tyr Pro Val Pro Pro Tyr Ala Phe Phe Phe Pro Pro Met Leu Gly Gly
 20                  25                  30
```

```
ctc tcc ccg cca ggc gct ctg acc act ctc cag cac cag ctt cca gtt        740
Leu Ser Pro Pro Gly Ala Leu Thr Thr Leu Gln His Gln Leu Pro Val
 35                  40                  45                  50
```

```
agt gga tat agc aca cca tcc cca gcc act gtg aga aac gac cga aac        788
Ser Gly Tyr Ser Thr Pro Ser Pro Ala Thr Val Arg Asn Asp Arg Asn
                55                  60                  65
```

```
aag aag aag aag gag gtg ccc aag ccc gag tgc tct gag agc tac acg        836
Lys Lys Lys Lys Glu Val Pro Lys Pro Glu Cys Ser Glu Ser Tyr Thr
         70                  75                  80
```

```
ctg acg ccg gag gtg ggg gag ctc att gag aag gtg cgc aaa gcg cac        884
Leu Thr Pro Glu Val Gly Glu Leu Ile Glu Lys Val Arg Lys Ala His
     85                  90                  95
```

```
cag gaa acc ttc cct gcc ctc tgc cag ctg ggc aaa tac act acg aac        932
Gln Glu Thr Phe Pro Ala Leu Cys Gln Leu Gly Lys Tyr Thr Thr Asn
100                 105                 110
```

-continued

```
aac agc tca gaa caa cgt gtc tct ctg gac att gac ctc tgg gac aag      980
Asn Ser Ser Glu Gln Arg Val Ser Leu Asp Ile Asp Leu Trp Asp Lys
115                 120                 125                 130 ttc agt gaa ctc tcc acc aag tgc atc att aag act gtg gag ttc gcc    1028
Phe Ser Glu Leu Ser Thr Lys Cys Ile Ile Lys Thr Val Glu Phe Ala
                135                 140                 145 aag cag ctg ccc ggc ttc acc acc ctc acc atc gcc gac cag atc acc    1076
Lys Gln Leu Pro Gly Phe Thr Thr Leu Thr Ile Ala Asp Gln Ile Thr
            150                 155                 160 ctc ctc aag gct gcc tgc ctg gac atc ctg atc ctg cgg atc tgc acg    1124
Leu Leu Lys Ala Ala Cys Leu Asp Ile Leu Ile Leu Arg Ile Cys Thr
        165                 170                 175 cgg tac acg ccc gag cag gac acc atg acc ttc tcg gac ggg ctg acc    1172
Arg Tyr Thr Pro Glu Gln Asp Thr Met Thr Phe Ser Asp Gly Leu Thr
    180                 185                 190 ctg aac cgg acc cag atg cac aac gct ggc ttc ggc ccc ctc acc gac    1220
Leu Asn Arg Thr Gln Met His Asn Ala Gly Phe Gly Pro Leu Thr Asp
195                 200                 205                 210 ctg gtc ttt gcc ttc gcc aac cag ctg ctg ccc ctg gag atg gat gat    1268
Leu Val Phe Ala Phe Ala Asn Gln Leu Leu Pro Leu Glu Met Asp Asp
                215                 220                 225 gcg gag acg ggg ctg ctc agc gcc atc tgc ctc atc tgc gga gac cgc    1316
Ala Glu Thr Gly Leu Leu Ser Ala Ile Cys Leu Ile Cys Gly Asp Arg
                230                 235                 240 cag gac ctg gag cag ccg gac cgg gtg gac atg ctg cag gag ccg ctg    1364
Gln Asp Leu Glu Gln Pro Asp Arg Val Asp Met Leu Gln Glu Pro Leu
            245                 250                 255 ctg gag gcg cta aag gtc tac gtg cgg aag cgg agg ccc agc cgc ccc    1412
Leu Glu Ala Leu Lys Val Tyr Val Arg Lys Arg Arg Pro Ser Arg Pro
        260                 265                 270 cac atg ttc ccc aag atg cta atg aag att act gac ctg cga agc atc    1460
His Met Phe Pro Lys Met Leu Met Lys Ile Thr Asp Leu Arg Ser Ile
275                 280                 285                 290 agc gcc aag ggg gct gag cgg gtg atc acg ctg aag atg gag atc ccg    1508
Ser Ala Lys Gly Ala Glu Arg Val Ile Thr Leu Lys Met Glu Ile Pro
                295                 300                 305 ggc tcc atg ccg cct ctc atc cag gaa atg ttg gag aac tca gag ggc    1556
Gly Ser Met Pro Pro Leu Ile Gln Glu Met Leu Glu Asn Ser Glu Gly
                310                 315                 320 ctg gac act ctg agc gga cag ccg ggg ggt ggg ggg cgg gac ggg ggt    1604
Leu Asp Thr Leu Ser Gly Gln Pro Gly Gly Gly Gly Arg Asp Gly Gly
            325                 330                 335 ggc ctg gcc ccc ccg cca ggc agc tgt agc ccc agc ctc agc ccc agc    1652
Gly Leu Ala Pro Pro Pro Gly Ser Cys Ser Pro Ser Leu Ser Pro Ser
        340                 345                 350 tcc aac aga agc agc ccg gcc acc cac tcc ccg tga ccgcccacgc         1698
Ser Asn Arg Ser Ser Pro Ala Thr His Ser Pro
355                 360                 365 cacatggaca cagccctcgc cctccgcccc ggcttttctc tgcctttcta ccgaccatgt   1758
gaccccgcac cagccctgcc cccacctgcc ctcccgggca gtactgggga ccttccctgg   1818
gggacgggga gggaggaggc agcgactcct tggacagagg cctgggccct cagtggactg   1878
cctgctccca cagcctgggc tgacgtcaga ggccgaggcc aggaactgag tgaggccctc   1938
ggtcctgggt ctcaggatgg gtcctggggg cctcgtgttc atcaagacac ccctctgccc   1998
agctcaccac atcttcatca ccagcaaacg ccaggacttg ctcccccat cctcagaact    2058 cacaagccat tgctccccag ctggggaacc tcaacctccc cctgcctcg gttggtgaca   2118
```

```
gaggggtgg  acaggggcg  ggggttccc  cctgtacata  ccctgccata  ccaaccccag    2178
gtattaattc  tcgctggttt  tgttttatt   ttaattttt   tgttttgatt  ttttaataa    2238 gaatttcat   tttaagcaca  tttatactga  aggaatttgt  gctgtgtatt  gggggagct   2298 ggatccagag  ctggagggg   tgggtccggg  ggagggagtg  gctcggaagg  gcccccact   2358 ctcctttcat  gtccctgtgc  ccccagttc   tcctcctcag  cctttcctc   ctcagttttc  2418 tctttaaaac  tgtgaagtac  taactttcca  aggcctgcct  tccctccct   cccactggag  2478 aagccgccag  ccctttctc   cctctgcctg  accactgggt  gtggacggtg  tggggcagcc  2538
ctgaaaggac  aggctcctgg  ccttggcact  tgcctgcacc  caccatgagg  catggagcag  2598
ggcagagcaa  gggccccggg  acagagtttt  cccagacctg  gctcctcggc  agagctgcct  2658
cccgtcaggg  cccacatcat  ctaggctccc  cagcccccac  tgtgaagggg  ctggccaggg  2718
gcccgagctg  ccccaccc    cggcctcagc  caccagcacc  cccatagggc  ccccagacac  2778
cacacacatg  cgcgtgcgca  cacacacaaa  cacacacaca  ctggacagta  gatgggccga  2838
cacacacttg  gcccgagttc  ctccattcc   ctggcctgcc  ccccacccc   aacctgtccc  2898 accccgtgc   cccctcctta  ccccgcagga  cgggcctaca  gggggtctc   ccctcacccc  2958 tgcaccccca  gctgggggag  ctggctctgc  cccgacctcc  ttcaccaggg  gttgggcc    3018 cttcccctgg  agcccgtggg  tgcacctgtt  actgttgggc  tttccactga  gatctactgg  3078
ataaagaata  aagttctatt  tattctaaaa  aaaaaaaaa   aaaa                    3122
```

<210> SEQ ID NO 8
<211> LENGTH: 3142
<212> TYPE: DNA
<213> ORGANISM: Homo sapiens
<220> FEATURE:
<221> NAME/KEY: CDS
<222> LOCATION: (390)..(1736)

<400> SEQUENCE: 8

```
tgcgagctgt  ttgaggactg  ggatgccgag  aacgcgagcg  atccgagcag  ggtttgtctg    60
ggcaccgtcg  gggtaggatc  cggaacgcat  tcggaaggct  ttttgcaagc  atttacttgg   120
aaggagaact  tgggatcttt  ctgggaaccc  ccgccccgg   ctggattggc  cgagcaagcc   180
tggaaaatgg  taaatgatca  tttggatcaa  ttacaggctt  ttagctggct  tgtctgtcat   240
aattcatgat  tcgggctgg   gaaaaagacc  aacagcctac  gtgccaaaaa  aggggcagag   300
tttgatggag  ttgggtggac  ttttctatgc  catttgcctc  cacacctaga  ggataagcac   360
ttttgcagac  attcagtgca  agggagatc  atg ttt gac tgt atg gat gtt ctg       413
                                  Met Phe Asp Cys Met Asp Val Leu
                                   1               5 tca gtg agt cct ggg caa atc ctg gat ttc tac act gcg agt ccg tct          461
Ser Val Ser Pro Gly Gln Ile Leu Asp Phe Tyr Thr Ala Ser Pro Ser
 10                  15                  20 tcc tgc atg ctc cag gag aaa gct ctc aaa gca tgc ttc agt gga ttg          509
Ser Cys Met Leu Gln Glu Lys Ala Leu Lys Ala Cys Phe Ser Gly Leu
 25                  30                  35                  40 acc caa acc gaa tgg cag cat cgg cac act gct caa tca att gaa aca          557
Thr Gln Thr Glu Trp Gln His Arg His Thr Ala Gln Ser Ile Glu Thr
                 45                  50                  55 cag agc acc agc tct gag gaa ctc gtc cca agc ccc cca tct cca ctt          605
Gln Ser Thr Ser Ser Glu Glu Leu Val Pro Ser Pro Pro Ser Pro Leu
             60                  65                  70 cct ccc cct cga gtg tac aaa ccc tgc ttc gtc tgc cag gac aaa tca          653
Pro Pro Pro Arg Val Tyr Lys Pro Cys Phe Val Cys Gln Asp Lys Ser
```

-continued

|  |  |  | 75 |  |  |  | 80 |  |  |  | 85 |  |  |  |  |
|---|---|---|---|---|---|---|---|---|---|---|---|---|---|---|---|

```
tca ggg tac cac tat ggg gtc agc gcc tgt gag gga tgt aag ggc ttt      701
Ser Gly Tyr His Tyr Gly Val Ser Ala Cys Glu Gly Cys Lys Gly Phe
         90                  95                 100 ttc cgc aga agt att cag aag aat atg att tac act tgt cac cga gat      749
Phe Arg Arg Ser Ile Gln Lys Asn Met Ile Tyr Thr Cys His Arg Asp
105                 110                 115                 120 aag aac tgt gtt att aat aaa gtc acc agg aat cga tgc caa tac tgt      797
Lys Asn Cys Val Ile Asn Lys Val Thr Arg Asn Arg Cys Gln Tyr Cys
                    125                 130                 135 cga ctc cag aag tgc ttt gaa gtg gga atg tcc aaa gaa tct gtc agg      845
Arg Leu Gln Lys Cys Phe Glu Val Gly Met Ser Lys Glu Ser Val Arg
                140                 145                 150 aat gac agg aac aag aaa aag aag gag act tcg aag caa gaa tgc aca      893
Asn Asp Arg Asn Lys Lys Lys Lys Glu Thr Ser Lys Gln Glu Cys Thr
            155                 160                 165 gag agc tat gaa atg aca gct gag ttg gac gat ctc aca gag aag atc      941
Glu Ser Tyr Glu Met Thr Ala Glu Leu Asp Asp Leu Thr Glu Lys Ile
        170                 175                 180 cga aaa gct cac cag gaa act ttc cct tca ctc tgc cag ctg ggt aaa      989
Arg Lys Ala His Gln Glu Thr Phe Pro Ser Leu Cys Gln Leu Gly Lys
185                 190                 195                 200 tac acc acg aat tcc agt gct gac cat cga gtc cga ctg gac ctg ggc     1037
Tyr Thr Thr Asn Ser Ser Ala Asp His Arg Val Arg Leu Asp Leu Gly
                    205                 210                 215 ctc tgg gac aaa ttc agt gaa ctg gcc acc aag tgc att att aag atc     1085
Leu Trp Asp Lys Phe Ser Glu Leu Ala Thr Lys Cys Ile Ile Lys Ile
                220                 225                 230 gtg gag ttt gct aaa cgt ctg cct ggt ttc act ggc ttg acc atc gca     1133
Val Glu Phe Ala Lys Arg Leu Pro Gly Phe Thr Gly Leu Thr Ile Ala
            235                 240                 245 gac caa att acc ctg ctg aag gcc gcc tgc ctg gac atc ctg att ctt     1181
Asp Gln Ile Thr Leu Leu Lys Ala Ala Cys Leu Asp Ile Leu Ile Leu
        250                 255                 260 aga att tgc acc agg tat acc cca gaa caa gac acc atg act ttc tca     1229
Arg Ile Cys Thr Arg Tyr Thr Pro Glu Gln Asp Thr Met Thr Phe Ser
265                 270                 275                 280 gac ggc ctt acc cta aat cga act cag atg cac aat gct gga ttt ggt     1277
Asp Gly Leu Thr Leu Asn Arg Thr Gln Met His Asn Ala Gly Phe Gly
                    285                 290                 295 cct ctg act gac ctt gtg ttc acc ttt gcc aac cag ctc ctg cct ttg     1325
Pro Leu Thr Asp Leu Val Phe Thr Phe Ala Asn Gln Leu Leu Pro Leu
                300                 305                 310 gaa atg gat gac aca gaa aca ggc ctt ctc agt gcc atc tgc tta atc     1373
Glu Met Asp Asp Thr Glu Thr Gly Leu Leu Ser Ala Ile Cys Leu Ile
            315                 320                 325 tgt gga gac cgc cag gac ctt gag gaa ccg aca aaa gta gat aag cta     1421
Cys Gly Asp Arg Gln Asp Leu Glu Glu Pro Thr Lys Val Asp Lys Leu
        330                 335                 340 caa gaa cca ttg ctg gaa gca cta aaa att tat atc aga aaa aga cga     1469
Gln Glu Pro Leu Leu Glu Ala Leu Lys Ile Tyr Ile Arg Lys Arg Arg
345                 350                 355                 360 ccc agc aag cct cac atg ttt cca aag atc tta atg aaa atc aca gat     1517
Pro Ser Lys Pro His Met Phe Pro Lys Ile Leu Met Lys Ile Thr Asp
                    365                 370                 375 ctc cgt agc atc agt gct aaa ggt gca gag cgt gta att acc ttg aaa     1565
Leu Arg Ser Ile Ser Ala Lys Gly Ala Glu Arg Val Ile Thr Leu Lys
                380                 385                 390 atg gaa att cct gga tca atg cca cct ctc att caa gaa atg ctg gag     1613
Met Glu Ile Pro Gly Ser Met Pro Pro Leu Ile Gln Glu Met Leu Glu
```

| | | | | | | | | | | | | |
|---|---|---|---|---|---|---|---|---|---|---|---|---|
| Met | Glu | Ile | Pro | Gly | Ser | Met | Pro | Pro | Leu | Ile | Gln | Glu | Met | Leu | Glu |
| | | | 395 | | | | 400 | | | | 405 | | | | |

| aat | tct | gaa | gga | cat | gaa | ccc | ttg | acc | cca | agt | tca | agt | ggg | aac | aca | 1661 |
|---|---|---|---|---|---|---|---|---|---|---|---|---|---|---|---|---|
| Asn | Ser | Glu | Gly | His | Glu | Pro | Leu | Thr | Pro | Ser | Ser | Ser | Gly | Asn | Thr | |
| | 410 | | | | | 415 | | | | | 420 | | | | | |

| gca | gag | cac | agt | cct | agc | atc | tca | ccc | agc | tca | gtg | gaa | aac | agt | ggg | 1709 |
|---|---|---|---|---|---|---|---|---|---|---|---|---|---|---|---|---|
| Ala | Glu | His | Ser | Pro | Ser | Ile | Ser | Pro | Ser | Ser | Val | Glu | Asn | Ser | Gly | |
| 425 | | | | | 430 | | | | | 435 | | | | | 440 | |

| gtc | agt | cag | tca | cca | ctc | gtg | caa | taa | gacattttct | agctacttca | 1756 |
|---|---|---|---|---|---|---|---|---|---|---|---|
| Val | Ser | Gln | Ser | Pro | Leu | Val | Gln | | | | |
| | | | | 445 | | | | | | | |

| | |
|---|---|
| aacattcccc agtaccttca gttccaggat ttaaatgca agaaaaaaca tttttactgc | 1816 |
| tgcttagttt ttggactgaa agatattaa aactcaagaa ggaccaagaa gttttcatat | 1876 |
| gtatcaatat atatactcct cactgtgtaa cttacctaga aatacaaact tttccaattt | 1936 |
| taaaaaatca gccatttcat gcaaccagaa actagttaaa agcttctatt ttcctctttg | 1996 |
| aacactcaag attgcatggc aaagacccag tcaaatgat ttacccctgg ttaagtttct | 2056 |
| gaagactttg tacatacaga agtatggctc tgttctttct atactgtatg tttggtgctt | 2116 |
| tccttttgtc ttgcatactc aaaataacca tgacaccaag gttatgaaat agactactgt | 2176 |
| acacgtctac ctaggttcaa aaagataact gtcttgcttt catggaatag tcaagacatc | 2236 |
| aaggtaagga acaggacta ttgacaggac tattgtacag tatgacaaga taaggctgaa | 2296 |
| gatattctac tttagttagt atggaagctt gtctttgctc tttctgatgc tctcaaactg | 2356 |
| catctttttat ttcatgttgc ccagtaaaag tatacaaatt ccctgcacta gcagaagaga | 2416 |
| attctgtatc agtgtaactg ccagttcagt taatcaaatg tcatttgttc aattgttaat | 2476 |
| gtcactttaa attaaaagtg gtttattact tgtttaatga cataactaca cagttagtta | 2536 |
| aaaaaaattt ttttacagta atgatagcct ccaaggcaga aacactttc agtgttaagt | 2596 |
| ttttgtttac ttgttcacaa gccattaggg aaatttcatg ggataattag caggctggtc | 2656 |
| taccacctgg accatgtaac tctagtgtcc ttcctgattc atgcctgata ttgggatttt | 2716 |
| tttttccagc cttcttgatg ccaaggggct aattaatatt aacaactccc aaagaaacag | 2776 |
| gcatagaatc tgcctccttt gaccttgttc aatcactatg aagcagagtg aaagctgtgg | 2836 |
| tagagtggtt aacagataca agtgtcagtt tcttagttct catttaagca ctagtggaat | 2896 |
| ttttttttttt tgatatatta gcaagtctgt gatgtacttt cactggctct gtttgtacat | 2956 |
| tgagattgtt tgtttaacaa tgctttctat gttcatatac tgtttaccttt tttccatgga | 3016 |
| gtctcctggc aaagaataaa atatatttat tttaaaaaaa aaaaaaaaaa aaaaaaaaa | 3076 |
| aaaaaaaaaa aaaaaaaaaa aaaaaaaaaa aaaaaaaaaa aaaaaaaaaa aaaaaaaaaa | 3136 |
| aaaaaa | 3142 |

<210> SEQ ID NO 9
<211> LENGTH: 2865
<212> TYPE: DNA
<213> ORGANISM: Homo sapiens
<220> FEATURE:
<221> NAME/KEY: CDS
<222> LOCATION: (449)..(1459)

<400> SEQUENCE: 9

| | |
|---|---|
| gtgacagaag tagtaggaag tgagctgttc agaggcagga gggtctattc tttgccaaag | 60 |
| gggggaccag aattccccca tgcgagctgt ttgaggactg ggatgccgag aacgcgagcg | 120 |
| atccgagcag ggtttgtctg gcaccgtcg gggtaggatc cggaacgcat tcggaaggct | 180 |

```
ttttgcaagc atttacttgg aaggagaact tgggatcttt ctgggaaccc cccgccccgg      240
ctggattggc cgagcaagcc tggaaaatgc aattgaaaca cagagcacca gctctgagga      300
actcgtccca agccccccat ctccacttcc tcccctcga gtgtacaaac cctgcttcgt       360
ctgccaggac aaatcatcag ggtaccacta tggggtcagc gcctgtgagg gatgtaaggg      420 cttttccgc agaagtattc agaagaat atg att tac act tgt cac cga gat          472
                              Met Ile Tyr Thr Cys His Arg Asp
                               1               5 aag aac tgt gtt att aat aaa gtc acc agg aat cga tgc caa tac tgt        520
Lys Asn Cys Val Ile Asn Lys Val Thr Arg Asn Arg Cys Gln Tyr Cys
 10              15                  20 cga ctc cag aag tgc ttt gaa gtg gga atg tcc aaa gaa tct gtc agg        568
Arg Leu Gln Lys Cys Phe Glu Val Gly Met Ser Lys Glu Ser Val Arg
 25              30                  35                  40 aat gac agg aac aag aaa aag gag act tcg aag caa gaa tgc aca            616
Asn Asp Arg Asn Lys Lys Lys Glu Thr Ser Lys Gln Glu Cys Thr
                 45                  50                  55 gag agc tat gaa atg aca gct gag ttg gac gat ctc aca gag aag atc        664
Glu Ser Tyr Glu Met Thr Ala Glu Leu Asp Asp Leu Thr Glu Lys Ile
                 60                  65                  70 cga aaa gct cac cag gaa act ttc cct tca ctc tgc cag ctg ggt aaa        712
Arg Lys Ala His Gln Glu Thr Phe Pro Ser Leu Cys Gln Leu Gly Lys
             75                  80                  85 tac acc acg aat tcc agt gct gac cat cga gtc cga ctg gac ctg ggc        760
Tyr Thr Thr Asn Ser Ser Ala Asp His Arg Val Arg Leu Asp Leu Gly
         90                  95                 100 ctc tgg gac aaa ttc agt gaa ctg gcc acc aag tgc att att aag atc        808
Leu Trp Asp Lys Phe Ser Glu Leu Ala Thr Lys Cys Ile Ile Lys Ile
105                 110                 115                 120 gtg gag ttt gct aaa cgt ctg cct ggt ttc act ggc ttg acc atc gca        856
Val Glu Phe Ala Lys Arg Leu Pro Gly Phe Thr Gly Leu Thr Ile Ala
                125                 130                 135 gac caa att acc ctg ctg aag gcc gcc tgc ctg gac atc ctg att ctt        904
Asp Gln Ile Thr Leu Leu Lys Ala Ala Cys Leu Asp Ile Leu Ile Leu
            140                 145                 150 aga att tgc acc agg tat acc cca gaa caa gac acc atg act ttc tca        952
Arg Ile Cys Thr Arg Tyr Thr Pro Glu Gln Asp Thr Met Thr Phe Ser
            155                 160                 165 gac ggc ctt acc cta aat cga act cag atg cac aat gct gga ttt ggt       1000
Asp Gly Leu Thr Leu Asn Arg Thr Gln Met His Asn Ala Gly Phe Gly
            170                 175                 180 cct ctg act gac ctt gtg ttc acc ttt gcc aac cag ctc ctg cct ttg       1048
Pro Leu Thr Asp Leu Val Phe Thr Phe Ala Asn Gln Leu Leu Pro Leu
185                 190                 195                 200 gaa atg gat gac aca gaa aca ggc ctt ctc agt gcc atc tgc tta atc       1096
Glu Met Asp Asp Thr Glu Thr Gly Leu Leu Ser Ala Ile Cys Leu Ile
                205                 210                 215 tgt gga gac cgc cag gac ctt gag gaa ccg aca aaa gta gat aag cta       1144
Cys Gly Asp Arg Gln Asp Leu Glu Glu Pro Thr Lys Val Asp Lys Leu
            220                 225                 230 caa gaa cca ttg ctg gaa gca cta aaa att tat atc aga aaa aga cga       1192
Gln Glu Pro Leu Leu Glu Ala Leu Lys Ile Tyr Ile Arg Lys Arg Arg
            235                 240                 245 ccc agc aag cct cac atg ttt cca aag atc tta atg aaa atc aca gat       1240
Pro Ser Lys Pro His Met Phe Pro Lys Ile Leu Met Lys Ile Thr Asp
250                 255                 260 ctc cgt agc atc agt gct aaa ggt gca gag cgt gta att acc ttg aaa       1288
Leu Arg Ser Ile Ser Ala Lys Gly Ala Glu Arg Val Ile Thr Leu Lys
```

| | | | | | | | | | | | | | | | | |
|---|---|---|---|---|---|---|---|---|---|---|---|---|---|---|---|---|
| | | 265 | | | | 270 | | | | 275 | | | | 280 | | |
| atg | gaa | att | cct | gga | tca | atg | cca | cct | ctc | att | caa | gaa | atg | ctg | gag | 1336 |
| Met | Glu | Ile | Pro | Gly | Ser | Met | Pro | Pro | Leu | Ile | Gln | Glu | Met | Leu | Glu | |
| | | 285 | | | | | | 290 | | | | | | 295 | | |
| aat | tct | gaa | gga | cat | gaa | ccc | ttg | acc | cca | agt | tca | agt | ggg | aac | aca | 1384 |
| Asn | Ser | Glu | Gly | His | Glu | Pro | Leu | Thr | Pro | Ser | Ser | Ser | Gly | Asn | Thr | |
| | | 300 | | | | | 305 | | | | | 310 | | | | |
| gca | gag | cac | agt | cct | agc | atc | tca | ccc | agc | tca | gtg | gaa | aac | agt | ggg | 1432 |
| Ala | Glu | His | Ser | Pro | Ser | Ile | Ser | Pro | Ser | Ser | Val | Glu | Asn | Ser | Gly | |
| | 315 | | | | | 320 | | | | | 325 | | | | | |
| gtc | agt | cag | tca | cca | ctc | gtg | caa | taa | gacattttct | agctacttca | | | | | | 1479 |
| Val | Ser | Gln | Ser | Pro | Leu | Val | Gln | | | | | | | | | |
| 330 | | | | | 335 | | | | | | | | | | | |

| | |
|---|---|
| aacattcccc agtaccttca gttccaggat ttaaaatgca agaaaaaaca ttttactgc | 1539 |
| tgcttagttt ttggactgaa aagatattaa aactcaagaa ggaccaagaa gttttcatat | 1599 |
| gtatcaatat atatactcct cactgtgtaa cttacctaga aatacaaact tttccaattt | 1659 |
| taaaaaatca gccatttcat gcaaccagaa actagttaaa agcttctatt ttcctctttg | 1719 |
| aacactcaag attgcatggc aaagacccag tcaaaatgat ttaccctgg ttaagtttct | 1779 |
| gaagactttg tacatacaga agtatggctc tgttctttct atactgtatg tttggtgctt | 1839 |
| tcctttttgtc ttgcatactc aaaataacca tgacaccaag gttatgaaat agactactgt | 1899 |
| acacgtctac ctaggttcaa aaagataact gtcttgcttt catggaatag tcaagacatc | 1959 |
| aaggtaagga acaggacta ttgacaggac tattgtacag tatgacaaga taaggctgaa | 2019 |
| gatattctac tttagttagt atggaagctt gtctttgctc tttctgatgc tctcaaactg | 2079 |
| catcttttat ttcatgttgc ccagtaaaag tatacaaatt ccctgcacta gcagaagaga | 2139 |
| attctgtatc agtgtaactg ccagttcagt taatcaaatg tcatttgttc aattgttaat | 2199 |
| gtcactttaa attaaaagtg gtttattact tgtttaatga cataactaca cagttagtta | 2259 |
| aaaaaaattt ttacagta atgatagcct ccaaggcaga aacacttttc agtgttaagt | 2319 |
| ttttgtttac ttgttcacaa gccattaggg aaatttcatg ggataattag caggctggtc | 2379 |
| taccacctgg accatgtaac tctagtgtcc ttcctgattc atgcctgata ttgggatttt | 2439 |
| ttttccagc cttcttgatg ccaaggggct aattaatatt aacaactccc aaagaaacag | 2499 |
| gcatagaatc tgcctccttt gaccttgttc aatcactatg aagcagagtg aaagctgtgg | 2559 |
| tagagtggtt aacagataca agtgtcagtt tcttagttct catttaagca ctagtggaat | 2619 |
| ttttttttt tgatatatta gcaagtctgt gatgtacttt cactggctct gtttgtacat | 2679 |
| tgagattgtt tgtttaacaa tgctttctat gttcatatac tgtttaccttt ttccatgga | 2739 |
| gtctcctggc aaagaataaa atatatttat tttaaaaaaa aaaaaaaaaa aaaaaaaaa | 2799 |
| aaaaaaaaaa aaaaaaaaaa aaaaaaaaaa aaaaaaaaaa aaaaaaaaaa aaaaaaaaaa | 2859 |
| aaaaaa | 2865 |

<210> SEQ ID NO 10
<211> LENGTH: 2992
<212> TYPE: DNA
<213> ORGANISM: Homo sapiens
<220> FEATURE:
<221> NAME/KEY: CDS
<222> LOCATION: (493)..(1857)

<400> SEQUENCE: 10
aggttggggg gggggtgggg agggagaaaa agaaagaaaa tattttccgt gtccccgcct    60

-continued

```
gcagagtcag tgtgcggttt gggagaaaat gtgtcggata ttttggggcg gtcacgtggg      120
cgggcgggct ccgagaggcc ccgggacagt cccagcctag agccgtgccc cccaggagc       180 cccccagtac ggcgagcccc ggacattgcg acgctccatc aagagactg cccgacgccg       240 ggacctcggg gctccgccgc ctcccttccc cctcccactc cagcagctac ggcccagttc      300
cctcaacctg acccagtatg tagaagccag tctctgcagg cggccagcgg gacttttgga      360 ggccagtgg gcaggccagg cagggcgggt acggagcctc ccaggctggg gcagtgggca       420
tgggcagggg ctgtggctga agacctcgcc cgcccactgc agaccccagg ggactctcac      480
accgcagctg cc atg gcc acc aat aag gag cga ctc ttt gcg gct ggt gcc     531
              Met Ala Thr Asn Lys Glu Arg Leu Phe Ala Ala Gly Ala
              1               5                  10 ctg ggg cct gga tct ggc tac cca ggg gca ggt ttc ccc ttc gcc ttc        579
Leu Gly Pro Gly Ser Gly Tyr Pro Gly Ala Gly Phe Pro Phe Ala Phe
 15                  20                  25 cca ggg gca ctc agg ggg tct ccg cct ttc gag atg ctg agc cct agc        627
Pro Gly Ala Leu Arg Gly Ser Pro Pro Phe Glu Met Leu Ser Pro Ser
 30                  35                  40                  45 ttc cgg ggc ctg ggc cag cct gac ctc ccc aag gag atg gcc tct ctg        675
Phe Arg Gly Leu Gly Gln Pro Asp Leu Pro Lys Glu Met Ala Ser Leu
                 50                  55                  60 tcg gtg gag aca cag agc acc agc tca gag gag atg gtg ccc agc tcg        723
Ser Val Glu Thr Gln Ser Thr Ser Ser Glu Glu Met Val Pro Ser Ser
             65                  70                  75 ccc tcg ccc cct ccg cct cct cgg gtc tac aag cca tgc ttc gtg tgc        771
Pro Ser Pro Pro Pro Pro Pro Arg Val Tyr Lys Pro Cys Phe Val Cys
         80                  85                  90 aat gac aag tcc tct ggc tac cac tat ggg gtc agc tct tgt gaa ggc        819
Asn Asp Lys Ser Ser Gly Tyr His Tyr Gly Val Ser Ser Cys Glu Gly
         95                 100                 105 tgc aag ggc ttc ttt cgc cga agc atc cag aag aac atg gtg tac acg        867
Cys Lys Gly Phe Phe Arg Arg Ser Ile Gln Lys Asn Met Val Tyr Thr
110                 115                 120                 125 tgt cac cgc gac aaa aac tgt atc atc aac aag gtg acc agg aat cgc        915
Cys His Arg Asp Lys Asn Cys Ile Ile Asn Lys Val Thr Arg Asn Arg
                130                 135                 140 tgc cag tac tgc cgg cta cag aag tgc ttc gaa gtg ggc atg tcc aag        963
Cys Gln Tyr Cys Arg Leu Gln Lys Cys Phe Glu Val Gly Met Ser Lys
            145                 150                 155 gaa gct gtg cga aat gac cgg aac aag aag aag aaa gag gtg aag gaa       1011
Glu Ala Val Arg Asn Asp Arg Asn Lys Lys Lys Lys Glu Val Lys Glu
        160                 165                 170 gaa ggg tca cct gac agc tat gag ctg agc cct cag tta gaa gag ctc       1059
Glu Gly Ser Pro Asp Ser Tyr Glu Leu Ser Pro Gln Leu Glu Glu Leu
    175                 180                 185 atc acc aag gtc agc aaa gcc cat cag gag act ttc ccc tcg ctc tgc       1107
Ile Thr Lys Val Ser Lys Ala His Gln Glu Thr Phe Pro Ser Leu Cys
190                 195                 200                 205 cag ctg ggc aag tat acc acg aac tcc agt gca gac cac cgc gtg cag       1155
Gln Leu Gly Lys Tyr Thr Thr Asn Ser Ser Ala Asp His Arg Val Gln
                210                 215                 220 ctg gat ctg ggg ctg tgg gac aag ttc agt gag ctg gct acc aag tgc       1203
Leu Asp Leu Gly Leu Trp Asp Lys Phe Ser Glu Leu Ala Thr Lys Cys
            225                 230                 235 atc atc aag atc gtg gag ttt gcc aag cgg ttg cct ggc ttt aca ggg       1251
Ile Ile Lys Ile Val Glu Phe Ala Lys Arg Leu Pro Gly Phe Thr Gly
        240                 245                 250 ctc agc att gct gac cag atc act ctg ctc aaa gct gcc tgc cta gat       1299
Leu Ser Ile Ala Asp Gln Ile Thr Leu Leu Lys Ala Ala Cys Leu Asp
```

```
Leu Ser Ile Ala Asp Gln Ile Thr Leu Leu Lys Ala Ala Cys Leu Asp
    255                 260                 265 atc ctg atg ctg cgt atc tgc aca agg tac acc cca gag cag gac acc    1347
Ile Leu Met Leu Arg Ile Cys Thr Arg Tyr Thr Pro Glu Gln Asp Thr
270                 275                 280                 285 atg acc ttc tcc gac ggg ctg acc ctg aac cgg acc cag atg cac aat    1395
Met Thr Phe Ser Asp Gly Leu Thr Leu Asn Arg Thr Gln Met His Asn
                    290                 295                 300 gcc ggc ttc ggg ccc ctc aca gac ctt gtc ttt gcc ttt gct ggg cag    1443
Ala Gly Phe Gly Pro Leu Thr Asp Leu Val Phe Ala Phe Ala Gly Gln
                305                 310                 315 ctc ctg ccc ctg gag atg gat gac acc gag aca ggg ctg ctc agc gcc    1491
Leu Leu Pro Leu Glu Met Asp Asp Thr Glu Thr Gly Leu Leu Ser Ala
            320                 325                 330 atc tgc ctc atc tgc gga gac cgc atg gac ctg gag gag ccc gaa aaa    1539
Ile Cys Leu Ile Cys Gly Asp Arg Met Asp Leu Glu Glu Pro Glu Lys
        335                 340                 345 gtg gac aag ctg cag gag cca ctg ctg gaa gcc ctg agg ctg tac gcc    1587
Val Asp Lys Leu Gln Glu Pro Leu Leu Glu Ala Leu Arg Leu Tyr Ala
350                 355                 360                 365 cgg cgc cgg cgg ccc agc cag ccc tac atg ttc cca agg atg cta atg    1635
Arg Arg Arg Arg Pro Ser Gln Pro Tyr Met Phe Pro Arg Met Leu Met
                    370                 375                 380 aaa atc acc gac ctc cgg ggc atc agc act aag gga gct gaa agg gcc    1683
Lys Ile Thr Asp Leu Arg Gly Ile Ser Thr Lys Gly Ala Glu Arg Ala
                385                 390                 395 att act ctg aag atg gag att cca ggc ccg atg cct ccc tta atc cga    1731
Ile Thr Leu Lys Met Glu Ile Pro Gly Pro Met Pro Pro Leu Ile Arg
            400                 405                 410 gag atg ctg gag aac cct gaa atg ttt gag gat gac tcc tcg cag cct    1779
Glu Met Leu Glu Asn Pro Glu Met Phe Glu Asp Asp Ser Ser Gln Pro
        415                 420                 425 ggt ccc cac ccc aat gcc tct agc gag gat gag gtt cct ggg ggc cag    1827
Gly Pro His Pro Asn Ala Ser Ser Glu Asp Glu Val Pro Gly Gly Gln
430                 435                 440                 445 ggc aaa ggg ggc ctg aag tcc cca gcc tga ccagggcccc tgacctcccc     1877
Gly Lys Gly Gly Leu Lys Ser Pro Ala
                    450 gctgtggggg ttggggcttc aggcagcaga ctgaccatct cccagaccgc cagtgactgg    1937 gggaggacct gctctgccct ctccccaccc cttccaatga gctccttgtt tttgccaaag    1997 tttctagggg tgcctctgtg ttcatcccct tcctgatcta accggctccc tcgccagtcc    2057 cgggggcctg ccctgctccc accaggagag agggcaaagg gatgagcctg gtttggact    2117 ctaaaatctc agcactgccc catgggtcct agacttccca gggcaagagg aagaccctgc    2177 cattccacag ccccttcctc tgccaggtgc ttggctctct gagagcaaac aggaacacta    2237 gagaccaaaa aggggacaaa ggagaagggc tgagcccacc ttcttgctcc tacccttggt    2297 gcctaatgct gtgtgatgca cctgcagggt gtgtgctagc ctctgtgccc cgtccttgtg    2357 ccaggtcaag gtgggggcag gctgggccct gcatttctgg ggcaggaaca gagggtgaaa    2417 gggacagata gatgcaggtc cattctgcac ctcttggctc gggtgcagag ttcaccctgt    2477 gccctccgtt ataagtccct ccccagccc tgtcatgtgc cttgggctcc tcctgccctc    2537 catctcagcc attggggcag ggaccctcct acactacaga ggggccaggg gatccctctc    2597 tccctagtgc cttccaccct ttactcccca gagcagcttg gcccagggag ggggatgct    2657 gcttagctga tcccgccctg acccagagga agcctctatt tatttattag cttttgttta    2717
```

```
caccgtggaa ttgacccctt cctccagggg tcttgggtgg gggagcccag ggcccctgtg      2777
acccctcctt tcttcctcca atccccagtt tgtatttagc tgccaaataa gattcccatt      2837
ggctccctgt gttctcttgg ggggtcaggg tgctgtcccc tccctctgt ttacatctcc       2897 cctctacccc gctgtatcgc atattgctga gttttctatt tttgcaaaat aaagtgatgg      2957
aaactcatga aaaaaaaaaa aaaaaaaaaa aaaaa                                 2992

<210> SEQ ID NO 11
<211> LENGTH: 2780
<212> TYPE: DNA
<213> ORGANISM: Homo sapiens
<220> FEATURE:
<221> NAME/KEY: CDS
<222> LOCATION: (314)..(1645)

<400> SEQUENCE: 11
caagccccac cccccacccc tccaggcttc gcttttaaaa aaggtctccc cagtgctagc      60
tgccgaagca cccagataag agctggacgg aggctaaagc ggcagcccca gcttcgcgcc     120
ccgcccagtc cctttcccct gctggggatc ccccctcttc cccgcccacc ccttacccgc     180
atgcagccca gcgccctatg ctagccctcc ccctcccccc ctgctggagc ggggcgccgc     240
cgggggagga gggggaatcg gctgcgggtc cttggtgttt ccagcaccca gtttcccttc     300
aagccgggtc gcg atg tac gac tgt atg gaa acg ttt gcc ccg ggt ccg        349
            Met Tyr Asp Cys Met Glu Thr Phe Ala Pro Gly Pro
              1               5                  10 cga cgg ctg tac ggg gcg gcc ggg ccc ggg gcc ggc ttg ctg cgc aga       397
Arg Arg Leu Tyr Gly Ala Ala Gly Pro Gly Ala Gly Leu Leu Arg Arg
        15                  20                  25 gcc acc ggc ggc tcc tgt ttc gcc gga ctt gaa tct ttt gcc tgg ccg       445
Ala Thr Gly Gly Ser Cys Phe Ala Gly Leu Glu Ser Phe Ala Trp Pro
    30                  35                  40 caa ccc gcc agc ctg caa tcg gtg gag aca cag agc acc agc tca gag       493
Gln Pro Ala Ser Leu Gln Ser Val Glu Thr Gln Ser Thr Ser Ser Glu
45                  50                  55                  60 gag atg gtg ccc agc tcg ccc tcg ccc cct ccg cct cct cgg gtc tac       541
Glu Met Val Pro Ser Ser Pro Ser Pro Pro Pro Pro Pro Arg Val Tyr
                65                  70                  75 aag cca tgc ttc gtg tgc aat gac aag tcc tct ggc tac cac tat ggg       589
Lys Pro Cys Phe Val Cys Asn Asp Lys Ser Ser Gly Tyr His Tyr Gly
            80                  85                  90 gtc agc tct tgt gaa ggc tgc aag ggc ttc ttt cgc cga agc atc cag       637
Val Ser Ser Cys Glu Gly Cys Lys Gly Phe Phe Arg Arg Ser Ile Gln
        95                 100                 105 aag aac atg gtg tac acg tgt cac cgc gac aaa aac tgt atc atc aac       685
Lys Asn Met Val Tyr Thr Cys His Arg Asp Lys Asn Cys Ile Ile Asn
    110                 115                 120 aag gtg acc agg aat cgc tgc cag tac tgc cgg cta cag aag tgc ttc       733
Lys Val Thr Arg Asn Arg Cys Gln Tyr Cys Arg Leu Gln Lys Cys Phe
125                 130                 135                 140 gaa gtg ggc atg tcc aag gaa gct gtg cga aat gac cgg aac aag aag       781
Glu Val Gly Met Ser Lys Glu Ala Val Arg Asn Asp Arg Asn Lys Lys
                145                 150                 155 aag aaa gag gtg aag gaa gaa ggg tca cct gac agc tat gag ctg agc       829
Lys Lys Glu Val Lys Glu Glu Gly Ser Pro Asp Ser Tyr Glu Leu Ser
            160                 165                 170 cct cag tta gaa gag ctc atc acc aag gtc agc aaa gcc cat cag gag       877
Pro Gln Leu Glu Glu Leu Ile Thr Lys Val Ser Lys Ala His Gln Glu
        175                 180                 185
```

| | | |
|---|---|---|
| act ttc ccc tcg ctc tgc cag ctg ggc aag tat acc acg aac tcc agt<br>Thr Phe Pro Ser Leu Cys Gln Leu Gly Lys Tyr Thr Thr Asn Ser Ser<br>190                              195                              200 | 925 |
| gca gac cac cgc gtg cag ctg gat ctg ggg ctg tgg gac aag ttc agt<br>Ala Asp His Arg Val Gln Leu Asp Leu Gly Leu Trp Asp Lys Phe Ser<br>205                              210                           215                 220 | 973 |
| gag ctg gct acc aag tgc atc atc aag atc gtg gag ttt gcc aag cgg<br>Glu Leu Ala Thr Lys Cys Ile Ile Lys Ile Val Glu Phe Ala Lys Arg<br>225                            230                           235 | 1021 |
| ttg cct ggc ttt aca ggg ctc agc att gct gac cag atc act ctg ctc<br>Leu Pro Gly Phe Thr Gly Leu Ser Ile Ala Asp Gln Ile Thr Leu Leu<br>                240                          245                           250 | 1069 |
| aaa gct gcc tgc cta gat atc ctg atg ctg cgt atc tgc aca agg tac<br>Lys Ala Ala Cys Leu Asp Ile Leu Met Leu Arg Ile Cys Thr Arg Tyr<br>255                              260                           265 | 1117 |
| acc cca gag cag gac acc atg acc ttc tcc gac ggg ctg acc ctg aac<br>Thr Pro Glu Gln Asp Thr Met Thr Phe Ser Asp Gly Leu Thr Leu Asn<br>270                              275                           280 | 1165 |
| cgg acc cag atg cac aat gcc ggc ttc ggg ccc ctc aca gac ctt gtc<br>Arg Thr Gln Met His Asn Ala Gly Phe Gly Pro Leu Thr Asp Leu Val<br>285                              290                           295                 300 | 1213 |
| ttt gcc ttt gct ggg cag ctc ctg ccc ctg gag atg gat gac acc gag<br>Phe Ala Phe Ala Gly Gln Leu Leu Pro Leu Glu Met Asp Asp Thr Glu<br>                305                          310                           315 | 1261 |
| aca ggg ctg ctc agc gcc atc tgc ctc atc tgc gga gac cgc atg gac<br>Thr Gly Leu Leu Ser Ala Ile Cys Leu Ile Cys Gly Asp Arg Met Asp<br>                320                          325                           330 | 1309 |
| ctg gag gag ccc gaa aaa gtg gac aag ctg cag gag cca ctg ctg gaa<br>Leu Glu Glu Pro Glu Lys Val Asp Lys Leu Gln Glu Pro Leu Leu Glu<br>                335                          340                           345 | 1357 |
| gcc ctg agg ctg tac gcc cgg cgc cgg ccc agc cag ccc tac atg<br>Ala Leu Arg Leu Tyr Ala Arg Arg Arg Pro Ser Gln Pro Tyr Met<br>350                              355                           360 | 1405 |
| ttc cca agg atg cta atg aaa atc acc gac ctc cgg ggc atc agc act<br>Phe Pro Arg Met Leu Met Lys Ile Thr Asp Leu Arg Gly Ile Ser Thr<br>365                              370                           375                 380 | 1453 |
| aag gga gct gaa agg gcc att act ctg aag atg gag att cca ggc ccg<br>Lys Gly Ala Glu Arg Ala Ile Thr Leu Lys Met Glu Ile Pro Gly Pro<br>                385                          390                           395 | 1501 |
| atg cct ccc tta atc cga gag atg ctg gag aac cct gaa atg ttt gag<br>Met Pro Pro Leu Ile Arg Glu Met Leu Glu Asn Pro Glu Met Phe Glu<br>                       400                           405                           410 | 1549 |
| gat gac tcc tcg cag cct ggt ccc cac ccc aat gcc tct agc gag gat<br>Asp Asp Ser Ser Gln Pro Gly Pro His Pro Asn Ala Ser Ser Glu Asp<br>                415                          420                           425 | 1597 |
| gag gtt cct ggg ggc cag ggc aaa ggg ggc ctg aag tcc cca gcc tga<br>Glu Val Pro Gly Gly Gln Gly Lys Gly Gly Leu Lys Ser Pro Ala<br>430                              435                           440 | 1645 |
| ccagggcccc tgacctcccc gctgtggggg ttggggcttc aggcagcaga ctgaccatct | 1705 |
| cccagaccgc cagtgactgg gggaggacct gctctgccct ctccccaccc cttccaatga | 1765 |
| gctccttgtt tttgccaaag tttctagggg tgcctctgtg ttcatcccct tcctgatcta | 1825 |
| accggctccc tcgccagtcc cgggggcctg ccctgctccc accaggagag agggcaaagg | 1885 |
| gatgagcctg ggtttggact ctaaaatctc agcactgccc catgggtcct agacttccca | 1945 |
| gggcaagagg aagaccctgc cattccacag cccttcctc tgccaggtgc ttggctctct | 2005 |
| gagagcaaac aggaacacta gagaccaaaa aggggacaaa ggagaagggc tgagcccacc | 2065 |
| ttcttgctcc tacccttggt gcctaatgct gtgtgatgca cctgcagggt gtgtgctagc | 2125 |

```
ctctgtgccc cgtccttgtg ccaggtcaag gtggggcag gctgggccct gcatttctgg    2185
ggcaggaaca gagggtgaaa gggacagata gatgcaggtc cattctgcac ctcttggctc    2245
gggtgcagag ttcaccctgt gccctccgtt ataagtccct ccccagccc tgtcatgtgc    2305 cttgggctcc tcctgccctc catctcagcc attggggcag ggaccctcct acactacaga    2365
ggggccaggg gatccctctc tccctagtgc cttccaccct ttactcccca gagcagcttg    2425
gcccagggag gggggatgct gcttagctga tcccgccctg acccagagga agcctctatt    2485
tatttattag cttttgttta caccgtggaa ttgaccccct cctccagggg tcttgggtgg    2545
gggagcccag ggccctgtg accctcctt tcttcctcca atcccagtt tgtatttagc    2605 tgccaaataa gattcccatt ggctccctgt gttctcttgg ggggtcaggg tgctgtcccc    2665
tcccctctgt ttacatctcc cctctacccc gctgtatcgc atattgctga gttttctatt    2725
tttgcaaaat aaagtgatgg aaactcatga aaaaaaaaa aaaaaaaaa aaaaa          2780
```

<210> SEQ ID NO 12
<211> LENGTH: 2631
<212> TYPE: DNA
<213> ORGANISM: Homo sapiens
<220> FEATURE:
<221> NAME/KEY: CDS
<222> LOCATION: (198)..(1496)

<400> SEQUENCE: 12

```
caagccccac cccccacccc tccaggcttc gctttttaaaa aaggtctccc cagtgctagc    60
tgccgaagca cccagataag agctggacgg aggctaaagc ggcagcccca gcttcgcgcc   120
ccgcccagtc cctttcccct gctggggatc cccctcttc ccgcccacc ccttacccgc     180 atgcagccca gcgccct atg cta gcc ctc ccc ctc ccc ccc tgc tgg agc      230
                    Met Leu Ala Leu Pro Leu Pro Pro Cys Trp Ser
                     1               5                  10 ggg gcg ccg ccg ggg gag gag ggg gaa tcg gct gcg ggt cct tgg tgt    278
Gly Ala Pro Pro Gly Glu Glu Gly Glu Ser Ala Ala Gly Pro Trp Cys
        15                  20                  25 ttc cag cac cca gtt tcc ctt caa gcc ggg tcg cga tgt acg act gta    326
Phe Gln His Pro Val Ser Leu Gln Ala Gly Ser Arg Cys Thr Thr Val
    30                  35                  40 tgg aaa cgt ttg ccc cgg gtc cgc gac ggc tgt acg ggg cgg ccg ggc    374
Trp Lys Arg Leu Pro Arg Val Arg Asp Gly Cys Thr Gly Arg Pro Gly
45                  50                  55 ccg ggg ccg gct tgc tgc gca gag cca ccg gcg gct cct gtt tcg ccg    422
Pro Gly Pro Ala Cys Cys Ala Glu Pro Pro Ala Ala Pro Val Ser Pro
60                  65                  70                  75 gac ttg aat ctt ttg cct ggc cgc aac ccg cca gcc tgc aat ggc ttc    470
Asp Leu Asn Leu Leu Pro Gly Arg Asn Pro Pro Ala Cys Asn Gly Phe
                80                  85                  90 ttt cgc cga agc atc cag aag aac atg gtg tac acg tgt cac cgc gac    518
Phe Arg Arg Ser Ile Gln Lys Asn Met Val Tyr Thr Cys His Arg Asp
            95                 100                 105 aaa aac tgt atc atc aac aag gtg acc agg aat cgc tgc cag tac tgc    566
Lys Asn Cys Ile Ile Asn Lys Val Thr Arg Asn Arg Cys Gln Tyr Cys
        110                 115                 120 cgg cta cag aag tgc ttc gaa gtg ggc atg tcc aag gaa gct gtg cga    614
Arg Leu Gln Lys Cys Phe Glu Val Gly Met Ser Lys Glu Ala Val Arg
    125                 130                 135 aat gac cgg aac aag aag aag aaa gag gtg aag gaa gaa ggg tca cct    662
Asn Asp Arg Asn Lys Lys Lys Lys Glu Val Lys Glu Glu Gly Ser Pro
140                 145                 150                 155
```

```
gac agc tat gag ctg agc cct cag tta gaa gag ctc atc acc aag gtc      710
Asp Ser Tyr Glu Leu Ser Pro Gln Leu Glu Glu Leu Ile Thr Lys Val
            160                 165                 170 agc aaa gcc cat cag gag act ttc ccc tcg ctc tgc cag ctg ggc aag      758
Ser Lys Ala His Gln Glu Thr Phe Pro Ser Leu Cys Gln Leu Gly Lys
                175                 180                 185 tat acc acg aac tcc agt gca gac cac cgc gtg cag ctg gat ctg ggg      806
Tyr Thr Thr Asn Ser Ser Ala Asp His Arg Val Gln Leu Asp Leu Gly
            190                 195                 200 ctg tgg gac aag ttc agt gag ctg gct acc aag tgc atc atc aag atc      854
Leu Trp Asp Lys Phe Ser Glu Leu Ala Thr Lys Cys Ile Ile Lys Ile
        205                 210                 215 gtg gag ttt gcc aag cgg ttg cct ggc ttt aca ggg ctc agc att gct      902
Val Glu Phe Ala Lys Arg Leu Pro Gly Phe Thr Gly Leu Ser Ile Ala
220                 225                 230                 235 gac cag atc act ctg ctc aaa gct gcc tgc cta gat atc ctg atg ctg      950
Asp Gln Ile Thr Leu Leu Lys Ala Ala Cys Leu Asp Ile Leu Met Leu
            240                 245                 250 cgt atc tgc aca agg tac acc cca gag cag gac acc atg acc ttc tcc      998
Arg Ile Cys Thr Arg Tyr Thr Pro Glu Gln Asp Thr Met Thr Phe Ser
            255                 260                 265 gac ggg ctg acc ctg aac cgg acc cag atg cac aat gcc ggc ttc ggg     1046
Asp Gly Leu Thr Leu Asn Arg Thr Gln Met His Asn Ala Gly Phe Gly
            270                 275                 280 ccc ctc aca gac ctt gtc ttt gcc ttt gct ggg cag ctc ctg ccc ctg     1094
Pro Leu Thr Asp Leu Val Phe Ala Phe Ala Gly Gln Leu Leu Pro Leu
            285                 290                 295 gag atg gat gac acc gag aca ggg ctg ctc agc gcc atc tgc ctc atc     1142
Glu Met Asp Asp Thr Glu Thr Gly Leu Leu Ser Ala Ile Cys Leu Ile
300                 305                 310                 315 tgc gga gac cgc atg gac ctg gag gag ccc gaa aaa gtg gac aag ctg     1190
Cys Gly Asp Arg Met Asp Leu Glu Glu Pro Glu Lys Val Asp Lys Leu
            320                 325                 330 cag gag cca ctg ctg gaa gcc ctg agg ctg tac gcc cgg cgc cgg cgg     1238
Gln Glu Pro Leu Leu Glu Ala Leu Arg Leu Tyr Ala Arg Arg Arg Arg
            335                 340                 345 ccc agc cag ccc tac atg ttc cca agg atg cta atg aaa atc acc gac     1286
Pro Ser Gln Pro Tyr Met Phe Pro Arg Met Leu Met Lys Ile Thr Asp
            350                 355                 360 ctc cgg ggc atc agc act aag gga gct gaa agg gcc att act ctg aag     1334
Leu Arg Gly Ile Ser Thr Lys Gly Ala Glu Arg Ala Ile Thr Leu Lys
        365                 370                 375 atg gag att cca ggc ccg atg cct ccc tta atc cga gag atg ctg gag     1382
Met Glu Ile Pro Gly Pro Met Pro Pro Leu Ile Arg Glu Met Leu Glu
380                 385                 390                 395 aac cct gaa atg ttt gag gat gac tcc tcg cag cct ggt ccc cac ccc     1430
Asn Pro Glu Met Phe Glu Asp Asp Ser Ser Gln Pro Gly Pro His Pro
                400                 405                 410 aat gcc tct agc gag gat gag gtt cct ggg ggc cag ggc aaa ggg ggc     1478
Asn Ala Ser Ser Glu Asp Glu Val Pro Gly Gly Gln Gly Lys Gly Gly
            415                 420                 425 ctg aag tcc cca gcc tga ccagggcccc tgacctcccc gctgtggggg            1526
Leu Lys Ser Pro Ala
            430 ttggggcttc aggcagcaga ctgaccatct cccagaccgc cagtgactgg gggaggacct   1586 gctctgccct ctccccaccc cttccaatga gctccttgtt tttgccaaag tttctagggg   1646 tgcctctgtg ttcatcccct tcctgatcta accggctccc tcgccagtcc cggggggcctg  1706
```

```
cctgctccc accaggagag agggcaaagg gatgagcctg ggtttggact ctaaaatctc      1766
agcactgccc catgggtcct agacttccca gggcaagagg aagaccctgc cattccacag      1826
ccccttcctc tgccaggtgc ttggctctct gagagcaaac aggaacacta gagaccaaaa      1886
aggggacaaa ggagaagggc tgagcccacc ttcttgctcc tacccttggt gcctaatgct      1946
gtgtgatgca cctgcagggt gtgtgctagc ctctgtgccc cgtccttgtg ccaggtcaag      2006
gtgggggcag gctgggccct gcatttctgg ggcaggaaca gagggtgaaa gggacagata      2066
gatgcaggtc cattctgcac ctcttggctc gggtgcagag ttcaccctgt gccctccgtt      2126
ataagtccct cccccagccc tgtcatgtgc cttgggctcc tcctgccctc catctcagcc      2186
attggggcag ggaccctcct acactacaga ggggccaggg gatccctctc tccctagtgc      2246
cttccaccct ttactcccca gagcagcttg gcccagggag gggggatgct gcttagctga      2306
tcccgccctg acccagagga agcctctatt tatttattag cttttgttta caccgtggaa      2366
ttgacccctt cctccagggg tcttgggtgg gggagcccag ggccctgtg accctcctt      2426 tcttcctcca atccccagtt tgtatttagc tgccaaataa gattcccatt ggctccctgt      2486
gttctcttgg ggggtcaggg tgctgtcccc tccctctgt ttacatctcc cctctacccc      2546
gctgtatcgc atattgctga gttttctatt tttgcaaaat aaagtgatgg aaactcatga      2606
aaaaaaaaaa aaaaaaaaaa aaaaa                                           2631

<210> SEQ ID NO 13
<211> LENGTH: 2666
<212> TYPE: DNA
<213> ORGANISM: Homo sapiens
<220> FEATURE:
<221> NAME/KEY: CDS
<222> LOCATION: (383)..(1531)

<400> SEQUENCE: 13
aggttggggg gggggtgggg agggagaaaa agaaagaaaa tattttccgt gtccccgcct       60
gcagagtcag tgtgcggttt gggagaaaat gtgtcggata ttttggggcg gtcacgtggg      120
cgggcgggct ccgagaggcc ccgggacagt cccagcctag agccgtgccc cccaggagc      180 cccccagtac ggcgagcccc ggacattgcg acgctccatc caagagactg cccgacgccg      240
ggacctcggg gctccgccgc ctcccttccc cctcccactc cagcagctac ggcccagttc      300
cctcaacctg acccagtatg tagaagccag tctctgcagg cggccagcgg cggtggagac      360
acagagcacc agctcagagg ag atg gtg ccc agc tcg ccc tcg ccc cct ccg      412
                          Met Val Pro Ser Ser Pro Ser Pro Pro Pro
                            1               5                  10 cct cct cgg gtc tac aag cca tgc ttc gtg tgc aat gac aag tcc tct      460
Pro Pro Arg Val Tyr Lys Pro Cys Phe Val Cys Asn Asp Lys Ser Ser
             15                  20                  25 ggc tac cac tat ggg gtc agc tct tgt gaa ggc tgc aag ggc ttc ttt      508
Gly Tyr His Tyr Gly Val Ser Ser Cys Glu Gly Cys Lys Gly Phe Phe
         30                  35                  40 cgc cga agc atc cag aag aac atg gtg tac acg tgt cac cgc gac aaa      556
Arg Arg Ser Ile Gln Lys Asn Met Val Tyr Thr Cys His Arg Asp Lys
     45                  50                  55 aac tgt atc atc aac aag gtg acc agg aat cgc tgc cag tac tgc cgg      604
Asn Cys Ile Ile Asn Lys Val Thr Arg Asn Arg Cys Gln Tyr Cys Arg
 60                  65                  70 cta cag aag tgc ttc gaa gtg ggc atg tcc aag gaa gct gtg cga aat      652
Leu Gln Lys Cys Phe Glu Val Gly Met Ser Lys Glu Ala Val Arg Asn
 75                  80                  85                  90
```

```
gac cgg aac aag aag aag aaa gag gtg aag gaa gaa ggg tca cct gac      700
Asp Arg Asn Lys Lys Lys Lys Glu Val Lys Glu Glu Gly Ser Pro Asp
             95                 100                 105 agc tat gag ctg agc cct cag tta gaa gag ctc atc acc aag gtc agc      748
Ser Tyr Glu Leu Ser Pro Gln Leu Glu Glu Leu Ile Thr Lys Val Ser
            110                 115                 120 aaa gcc cat cag gag act ttc ccc tcg ctc tgc cag ctg ggc aag tat      796
Lys Ala His Gln Glu Thr Phe Pro Ser Leu Cys Gln Leu Gly Lys Tyr
            125                 130                 135 acc acg aac tcc agt gca gac cac cgc gtg cag ctg gat ctg ggg ctg      844
Thr Thr Asn Ser Ser Ala Asp His Arg Val Gln Leu Asp Leu Gly Leu
        140                 145                 150 tgg gac aag ttc agt gag ctg gct acc aag tgc atc atc aag atc gtg      892
Trp Asp Lys Phe Ser Glu Leu Ala Thr Lys Cys Ile Ile Lys Ile Val
155                 160                 165                 170 gag ttt gcc aag cgg ttg cct ggc ttt aca ggg ctc agc att gct gac      940
Glu Phe Ala Lys Arg Leu Pro Gly Phe Thr Gly Leu Ser Ile Ala Asp
                175                 180                 185 cag atc act ctg ctc aaa gct gcc tgc cta gat atc ctg atg ctg cgt      988
Gln Ile Thr Leu Leu Lys Ala Ala Cys Leu Asp Ile Leu Met Leu Arg
            190                 195                 200 atc tgc aca agg tac acc cca gag cag gac acc atg acc ttc tcc gac     1036
Ile Cys Thr Arg Tyr Thr Pro Glu Gln Asp Thr Met Thr Phe Ser Asp
        205                 210                 215 ggg ctg acc ctg aac cgg acc cag atg cac aat gcc ggc ttc ggg ccc     1084
Gly Leu Thr Leu Asn Arg Thr Gln Met His Asn Ala Gly Phe Gly Pro
    220                 225                 230 ctc aca gac ctt gtc ttt gcc ttt gct ggg cag ctc ctg ccc ctg gag     1132
Leu Thr Asp Leu Val Phe Ala Phe Ala Gly Gln Leu Leu Pro Leu Glu
235                 240                 245                 250 atg gat gac acc gag aca ggg ctg ctc agc gcc atc tgc ctc atc tgc     1180
Met Asp Asp Thr Glu Thr Gly Leu Leu Ser Ala Ile Cys Leu Ile Cys
                255                 260                 265 gga gac cgc atg gac ctg gag gag ccc gaa aaa gtg gac aag ctg cag     1228
Gly Asp Arg Met Asp Leu Glu Glu Pro Glu Lys Val Asp Lys Leu Gln
            270                 275                 280 gag cca ctg ctg gaa gcc ctg agg ctg tac gcc cgg cgc cgg cgg ccc     1276
Glu Pro Leu Leu Glu Ala Leu Arg Leu Tyr Ala Arg Arg Arg Arg Pro
        285                 290                 295 agc cag ccc tac atg ttc cca agg atg cta atg aaa atc acc gac ctc     1324
Ser Gln Pro Tyr Met Phe Pro Arg Met Leu Met Lys Ile Thr Asp Leu
    300                 305                 310 cgg ggc atc agc act aag gga gct gaa agg gcc att act ctg aag atg     1372
Arg Gly Ile Ser Thr Lys Gly Ala Glu Arg Ala Ile Thr Leu Lys Met
315                 320                 325                 330 gag att cca ggc ccg atg cct ccc tta atc cga gag atg ctg gag aac     1420
Glu Ile Pro Gly Pro Met Pro Pro Leu Ile Arg Glu Met Leu Glu Asn
                335                 340                 345 cct gaa atg ttt gag gat gac tcc tcg cag cct ggt ccc cac ccc aat     1468
Pro Glu Met Phe Glu Asp Asp Ser Ser Gln Pro Gly Pro His Pro Asn
            350                 355                 360 gcc tct agc gag gat gag gtt cct ggg ggc cag ggc aaa ggg ggc ctg     1516
Ala Ser Ser Glu Asp Glu Val Pro Gly Gly Gln Gly Lys Gly Gly Leu
        365                 370                 375 aag tcc cca gcc tga ccagggcccc tgacctcccc gctgtggggg ttgggcttc      1571
Lys Ser Pro Ala
    380 aggcagcaga ctgaccatct cccagaccgc cagtgactgg gggaggacct gctctgccct      1631 ctccccaccc cttccaatga gctccttgtt tttgccaaag tttctagggg tgcctctgtg      1691
```

```
ttcatcccct tcctgatcta accggctccc tcgccagtcc cggggggcctg ccctgctccc    1751 accaggagag agggcaaagg gatgagcctg ggtttggact ctaaaatctc agcactgccc    1811
catgggtcct agacttccca gggcaagagg aagaccctgc cattccacag cccctccctc    1871
tgccaggtgc ttggctctct gagagcaaac aggaacacta gagaccaaaa agggacaaa     1931 ggagaagggc tgagcccacc ttcttgctcc tacccttggt gcctaatgct gtgtgatgca    1991
cctgcagggt gtgtgctagc ctctgtgccc cgtccttgtg ccaggtcaag gtgggggcag    2051
gctgggccct gcatttctgg ggcaggaaca gagggtgaaa gggacagata gatgcaggtc    2111
cattctgcac ctcttggctc gggtgcagag ttcaccctgt gccctccgtt ataagtccct    2171
cccccagccc tgtcatgtgc cttgggctcc tcctgccctc catctcagcc attggggcag    2231
ggaccctcct acactacaga ggggccaggg gatccctctc tccctagtgc cttccaccct    2291
ttactcccca gagcagcttg gcccagggag gggggatgct gcttagctga tcccgccctg    2351
acccagagga agcctctatt tatttattag cttttgttta caccgtggaa ttgacccctt    2411
cctccagggg tcttgggtgg gggagcccag ggcccctgtg accctccctt tcttcctcca    2471
atccccagtt tgtatttagc tgccaaataa gattcccatt ggctccctgt gttctcttgg    2531
ggggtcaggg tgctgtcccc tcccctctgt ttacatctcc cctctacccc gctgtatcgc    2591
atattgctga gttttctatt tttgcaaaat aaagtgatgg aaactcatga aaaaaaaaa     2651 aaaaaaaaaa aaaaa                                                     2666

<210> SEQ ID NO 14
<211> LENGTH: 2517
<212> TYPE: DNA
<213> ORGANISM: Homo sapiens
<220> FEATURE:
<221> NAME/KEY: CDS
<222> LOCATION: (381)..(1382)

<400> SEQUENCE: 14
aggttggggg gggggtgggg agggagaaaa agaaagaaaa tattttccgt gtccccgcct    60
gcagagtcag tgtgcggttt gggagaaaat gtgtcggata ttttgggcg gtcacgtggg     120 cgggcgggct ccgagaggcc ccgggacagt cccagcctag agccgtgccc ccccaggagc    180
cccccagtac ggcgagcccc ggacattgcg acgctccatc caagactg cccgacgccg       240 ggacctcggg gctccgccgc ctcccttccc cctcccactc cagcagctac ggcccagttc    300
cctcaacctg acccagtatg tagaagccag tctctgcagg cggccagcgg ggcttctttc    360
gccgaagcat ccagaagaac atg gtg tac acg tgt cac cgc gac aaa aac tgt    413
                       Met Val Tyr Thr Cys His Arg Asp Lys Asn Cys
                         1               5                  10 atc atc aac aag gtg acc agg aat cgc tgc cag tac tgc cgg cta cag       461
Ile Ile Asn Lys Val Thr Arg Asn Arg Cys Gln Tyr Cys Arg Leu Gln
             15                  20                  25 aag tgc ttc gaa gtg ggc atg tcc aag gaa gct gtg cga aat gac cgg       509
Lys Cys Phe Glu Val Gly Met Ser Lys Glu Ala Val Arg Asn Asp Arg
         30                  35                  40 aac aag aag aag aaa gag gtg aag gaa gaa ggg tca cct gac agc tat       557
Asn Lys Lys Lys Lys Glu Val Lys Glu Glu Gly Ser Pro Asp Ser Tyr
     45                  50                  55 gag ctg agc cct cag tta gaa gag ctc atc acc aag gtc agc aaa gcc       605
Glu Leu Ser Pro Gln Leu Glu Glu Leu Ile Thr Lys Val Ser Lys Ala
 60                  65                  70                  75 cat cag gag act ttc ccc tcg ctc tgc cag ctg ggc aag tat acc acg       653
```

|  |  |
|---|---:|
| His Gln Glu Thr Phe Pro Ser Leu Cys Gln Leu Gly Lys Tyr Thr Thr<br>                      80                        85                        90 |  |
| aac tcc agt gca gac cac cgc gtg cag ctg gat ctg ggg ctg tgg gac<br>Asn Ser Ser Ala Asp His Arg Val Gln Leu Asp Leu Gly Leu Trp Asp<br>                95                        100                      105 | 701 |
| aag ttc agt gag ctg gct acc aag tgc atc atc aag atc gtg gag ttt<br>Lys Phe Ser Glu Leu Ala Thr Lys Cys Ile Ile Lys Ile Val Glu Phe<br>        110                        115                        120 | 749 |
| gcc aag cgg ttg cct ggc ttt aca ggg ctc agc att gct gac cag atc<br>Ala Lys Arg Leu Pro Gly Phe Thr Gly Leu Ser Ile Ala Asp Gln Ile<br>      125                        130                        135 | 797 |
| act ctg ctc aaa gct gcc tgc cta gat atc ctg atg ctg cgt atc tgc<br>Thr Leu Leu Lys Ala Ala Cys Leu Asp Ile Leu Met Leu Arg Ile Cys<br>140                        145                        150                        155 | 845 |
| aca agg tac acc cca gag cag gac acc atg acc ttc tcc gac ggg ctg<br>Thr Arg Tyr Thr Pro Glu Gln Asp Thr Met Thr Phe Ser Asp Gly Leu<br>                      160                        165                      170 | 893 |
| acc ctg aac cgg acc cag atg cac aat gcc ggc ttc ggg ccc ctc aca<br>Thr Leu Asn Arg Thr Gln Met His Asn Ala Gly Phe Gly Pro Leu Thr<br>                175                        180                        185 | 941 |
| gac ctt gtc ttt gcc ttt gct ggg cag ctc ctg ccc ctg gag atg gat<br>Asp Leu Val Phe Ala Phe Ala Gly Gln Leu Leu Pro Leu Glu Met Asp<br>            190                        195                        200 | 989 |
| gac acc gag aca ggg ctg ctc agc gcc atc tgc ctc atc tgc gga gac<br>Asp Thr Glu Thr Gly Leu Leu Ser Ala Ile Cys Leu Ile Cys Gly Asp<br>      205                        210                        215 | 1037 |
| cgc atg gac ctg gag gag ccc gaa aaa gtg gac aag ctg cag gag cca<br>Arg Met Asp Leu Glu Glu Pro Glu Lys Val Asp Lys Leu Gln Glu Pro<br>220                        225                        230                        235 | 1085 |
| ctg ctg gaa gcc ctg agg ctg tac gcc cgg cgc cgg cgg ccc agc cag<br>Leu Leu Glu Ala Leu Arg Leu Tyr Ala Arg Arg Arg Arg Pro Ser Gln<br>                240                        245                      250 | 1133 |
| ccc tac atg ttc cca agg atg cta atg aaa atc acc gac ctc cgg ggc<br>Pro Tyr Met Phe Pro Arg Met Leu Met Lys Ile Thr Asp Leu Arg Gly<br>            255                        260                        265 | 1181 |
| atc agc act aag gga gct gaa agg gcc att act ctg aag atg gag att<br>Ile Ser Thr Lys Gly Ala Glu Arg Ala Ile Thr Leu Lys Met Glu Ile<br>          270                        275                        280 | 1229 |
| cca ggc ccg atg cct ccc tta atc cga gag atg ctg gag aac cct gaa<br>Pro Gly Pro Met Pro Pro Leu Ile Arg Glu Met Leu Glu Asn Pro Glu<br>285                        290                        295 | 1277 |
| atg ttt gag gat gac tcc tcg cag cct ggt ccc cac ccc aat gcc tct<br>Met Phe Glu Asp Asp Ser Ser Gln Pro Gly Pro His Pro Asn Ala Ser<br>300                        305                        310                        315 | 1325 |
| agc gag gat gag gtt cct ggg ggc cag ggc aaa ggg ggc ctg aag tcc<br>Ser Glu Asp Glu Val Pro Gly Gly Gln Gly Lys Gly Gly Leu Lys Ser<br>                320                        325                      330 | 1373 |
| cca gcc tga ccagggcccc tgacctcccc gctgtggggg ttggggcttc<br>Pro Ala | 1422 |
| aggcagcaga ctgaccatct cccagaccgc cagtgactgg gggaggacct gctctgccct | 1482 |
| ctccccaccc cttccaatga gctccttgtt tttgccaaag tttctagggg tgcctctgtg | 1542 |
| ttcatcccct tcctgatcta accggctccc tcgccagtcc cggggggcctg ccctgctccc | 1602 |
| accaggagag agggcaaagg gatgagcctg ggtttggact ctaaaatctc agcactgccc | 1662 |
| catgggtcct agacttccca gggcaagagg aagaccctgc cattccacag ccccttcctc | 1722 |
| tgccaggtgc ttggctctct gagagcaaac aggaacacta gagaccaaaa agggggacaaa | 1782 |

```
ggagaagggc tgagcccacc ttcttgctcc tacccttggt gcctaatgct gtgtgatgca    1842
cctgcagggt gtgtgctagc ctctgtgccc cgtccttgtg ccaggtcaag gtggggcag     1902 gctgggccct gcatttctgg ggcaggaaca gagggtgaaa gggacagata gatgcaggtc    1962
cattctgcac ctcttggctc gggtgcagag ttcaccctgt gccctccgtt ataagtccct    2022
cccccagccc tgtcatgtgc ctttgggctcc tcctgccctc catctcagcc attggggcag   2082
ggaccctcct acactacaga ggggccaggg gatccctctc tccctagtgc cttccaccct    2142
ttactcccca gagcagcttg gcccagggag ggggatgct gcttagctga tcccgccctg     2202
acccagagga agcctctatt tatttattag cttttgttta caccgtggaa ttgacccctt    2262
cctccagggg tcttgggtgg gggagcccag ggcccctgtg accctcctt tcttcctcca     2322 atccccagtt tgtatttagc tgccaaataa gattcccatt ggctccctgt gttctcttgg    2382
ggggtcaggg tgctgtcccc tcccctctgt ttacatctcc cctctacccc gctgtatcgc    2442
atattgctga gttttctatt tttgcaaaat aaagtgatgg aaactcatga aaaaaaaaa     2502 aaaaaaaaaa aaaaa                                                     2517
```

<210> SEQ ID NO 15
<211> LENGTH: 16
<212> TYPE: PRT
<213> ORGANISM: Homo sapiens

<400> SEQUENCE: 15

Lys Arg Tyr Phe Lys Leu Ser His Leu Gln Met His Ser Arg Lys His
1               5                   10                  15

<210> SEQ ID NO 16
<211> LENGTH: 22
<212> TYPE: PRT
<213> ORGANISM: Homo sapiens

<400> SEQUENCE: 16

Ala Leu Ala Glu Thr Ser Tyr Val Lys Val Leu Glu His Val Val Arg
1               5                   10                  15

Val Asn Ala Arg Val Arg
            20

<210> SEQ ID NO 17
<211> LENGTH: 15
<212> TYPE: PRT
<213> ORGANISM: Homo sapiens

<400> SEQUENCE: 17

Thr Leu Gly Glu Phe Leu Lys Leu Asp Arg Glu Arg Ala Lys Asn
1               5                   10                  15

<210> SEQ ID NO 18
<211> LENGTH: 52
<212> TYPE: RNA
<213> ORGANISM: Artificial sequence
<220> FEATURE:
<223> OTHER INFORMATION: shRNA 5' to 3'
<220> FEATURE:
<221> NAME/KEY: misc_feature
<222> LOCATION: (22)..(31)
<223> OTHER INFORMATION: loop

<400> SEQUENCE: 18
guacacuucu gggccacuga acuuccuguc auuuaguggu ccagaagugu gc            52

```
<210> SEQ ID NO 19
<211> LENGTH: 52
<212> TYPE: DNA
<213> ORGANISM: Artificial sequence
<220> FEATURE:
<223> OTHER INFORMATION: coding sequence for shRNA

<400> SEQUENCE: 19
gtacacttct gggccactga acttcctgtc atttagtggt ccagaagtgt gc          52

<210> SEQ ID NO 20
<211> LENGTH: 52
<212> TYPE: RNA
<213> ORGANISM: Artificial sequence
<220> FEATURE:
<223> OTHER INFORMATION: shRNA 5' to 3'
<220> FEATURE:
<221> NAME/KEY: misc_feature
<222> LOCATION: (22)..(31)
<223> OTHER INFORMATION: loop

<400> SEQUENCE: 20
gguuguggca gcauugcaug acuuccuguc auuaugcagu gcugccauaa cc          52
```